US012778115B2

(12) United States Patent
Vrselja

(10) Patent No.: US 12,778,115 B2
(45) Date of Patent: Nov. 3, 2026

(54) PERFUSION AND METABOLIC RESTORATION OF ORGANS

(71) Applicant: Bexorg, Inc., New Haven, CT (US)

(72) Inventor: Zvonimir Vrselja, New Haven, CT (US)

(73) Assignee: Bexorg, Inc., New Haven, CT (US)

( * ) Notice: Subject to any disclaimer, the term of this patent is extended or adjusted under 35 U.S.C. 154(b) by 0 days.

(21) Appl. No.: 19/070,309

(22) Filed: Mar. 4, 2025

(65) Prior Publication Data

US 2025/0280821 A1 Sep. 11, 2025

Related U.S. Application Data

(60) Provisional application No. 63/562,094, filed on Mar. 6, 2024.

(51) Int. Cl.
*A01N 1/143* (2025.01)
*G01N 21/65* (2006.01)
*G01N 33/50* (2006.01)

(52) U.S. Cl.
CPC ............ *A01N 1/143* (2025.01); *G01N 21/65* (2013.01); *G01N 33/5082* (2013.01)

(58) Field of Classification Search
None
See application file for complete search history.

(56) References Cited

U.S. PATENT DOCUMENTS 6,699,231 B1 3/2004 Sterman et al.
7,004,109 B2 2/2006 Olive et al.
7,568,446 B2 8/2009 Olive et al.
7,776,526 B2 8/2010 Zal et al.
8,837,800 B1 9/2014 Bammer et al.
8,846,306 B2 9/2014 Zal et al.
9,320,269 B2 4/2016 Brassil
9,663,761 B2 5/2017 Zal
9,861,095 B2 1/2018 Dutheil et al.
(Continued)

FOREIGN PATENT DOCUMENTS

AU 2022345865 3/2024
CA 3231611 3/2023
(Continued)

OTHER PUBLICATIONS

Gunston, Bill, (2009), Cambridge Aerospace Dictionary (2nd Edition), Cambridge University Press, retrieved from knovel.com. (Year: 2009).*

(Continued)

*Primary Examiner* — Michael A Marcheschi
*Assistant Examiner* — Ashley Lopezlira
(74) *Attorney, Agent, or Firm* — Fish & Richardson P.C.

(57) ABSTRACT

An ex-vivo brain perfusion system for perfusion of a brain includes a reservoir configured to receive perfusate, a housing configured to contain the brain, an arterial circuit configured to fluidly couple the reservoir to the brain, a venous circuit fluidly coupling the housing to the reservoir, and a syringe pump fluidly coupled to the reservoir and configured to introduce a therapeutic agent to the perfusate in the reservoir. The ex-vivo brain perfusion system is configured to perfuse the brain with the therapeutic agent to test at least one property of the therapeutic agent.

20 Claims, 23 Drawing Sheets

(56) References Cited

U.S. PATENT DOCUMENTS

| | | | |
|---|---|---|---|
| 10,988,730 B2 | 4/2021 | Zal | |
| 11,103,615 B2 | 8/2021 | Zal et al. | |
| 11,295,448 B1 | 4/2022 | Bammer et al. | |
| 11,998,001 B2 | 6/2024 | Daniele et al. | |
| 2004/0259769 A1 | 12/2004 | Looker et al. | |
| 2005/0272148 A1 | 12/2005 | Hariri | |
| 2006/0174356 A1 | 8/2006 | Pallanck et al. | |
| 2007/0100358 A2 | 5/2007 | Romero-Ortega et al. | |
| 2008/0187901 A1 | 8/2008 | Doorschodt et al. | |
| 2008/0305178 A1 | 12/2008 | Zal et al. | |
| 2009/0087328 A1* | 4/2009 | Faulkner | A61M 60/113 417/479 |
| 2010/0028979 A1 | 2/2010 | Faulkner et al. | |
| 2010/0151435 A1 | 6/2010 | Thatte et al. | |
| 2011/0183310 A1 | 7/2011 | Kravitz et al. | |
| 2012/0100540 A1 | 4/2012 | Wu et al. | |
| 2012/0238998 A1 | 9/2012 | Kiessling et al. | |
| 2014/0272920 A1* | 9/2014 | Potenziano | A61M 1/3623 435/1.1 |
| 2015/0342177 A1* | 12/2015 | Hassanein | A01N 1/143 435/284.1 |
| 2015/0374796 A1 | 12/2015 | Zal | |
| 2016/0160176 A1 | 6/2016 | Brasile | |
| 2017/0007616 A1 | 1/2017 | Gardner | |
| 2017/0252701 A1 | 9/2017 | Nosrati | |
| 2018/0187901 A1 | 7/2018 | Tian et al. | |
| 2019/0084931 A1 | 3/2019 | Chen et al. | |
| 2020/0209118 A1 | 7/2020 | Erturk | |
| 2020/0375178 A1 | 12/2020 | Becker et al. | |
| 2021/0007697 A1 | 1/2021 | Matthews et al. | |
| 2021/0060136 A1 | 3/2021 | Zal | |
| 2021/0113471 A1 | 4/2021 | Zal et al. | |
| 2021/0172900 A1 | 6/2021 | Zal | |
| 2021/0260226 A1 | 8/2021 | Sener et al. | |
| 2021/0360913 A1 | 11/2021 | Daniele et al. | |
| 2022/0160309 A1 | 5/2022 | Poltorak | |
| 2022/0287295 A1 | 9/2022 | Zal | |
| 2023/0099024 A1 | 3/2023 | Freeman et al. | |
| 2023/0127721 A1 | 4/2023 | Zal | |
| 2024/0156918 A1 | 5/2024 | Zal et al. | |
| 2024/0292830 A1 | 9/2024 | Daniele et al. | |
| 2024/0373840 A1 | 11/2024 | Sestan et al. | |
| 2025/0225409 A1 | 7/2025 | Vrselja et al. | |
| 2025/0367353 A1 | 12/2025 | Vrselja | |
| 2026/0200972 A1 | 7/2026 | Vrselja | |

FOREIGN PATENT DOCUMENTS

| | | |
|---|---|---|
| EP | 1679959 | 7/2006 |
| EP | 2427483 | 3/2012 |
| EP | 3749091 | 12/2020 |
| EP | 4125997 | 2/2023 |
| EP | 4402242 | 7/2024 |
| JP | 2024-535843 | 10/2024 |
| WO | WO 2001043797 | 6/2001 |
| WO | WO 2001092320 | 12/2001 |
| WO | WO 2002047744 | 6/2002 |
| WO | WO 2005037392 | 4/2005 |
| WO | WO 2006042138 | 4/2006 |
| WO | WO 2009007532 | 1/2009 |
| WO | WO 2009050343 | 4/2009 |
| WO | WO 2010122080 | 10/2010 |
| WO | WO 2010128159 | 11/2010 |
| WO | WO 2011149602 | 12/2011 |
| WO | WO 2013001196 | 1/2013 |
| WO | WO 2013030496 | 3/2013 |
| WO | WO 2013182806 | 12/2013 |
| WO | WO 2014059316 | 4/2014 |
| WO | WO 2014125225 | 8/2014 |
| WO | WO 2014184492 | 11/2014 |
| WO | WO 2017105237 | 6/2017 |
| WO | WO 2019141744 | 7/2019 |
| WO | WO 2019157277 | 8/2019 |
| WO | WO 2019201863 | 10/2019 |
| WO | WO 2021032763 | 2/2021 |
| WO | WO 2021198336 | 10/2021 |
| WO | WO 2023044014 | 3/2023 |
| WO | WO 2023250497 | 12/2023 |
| WO | WO 2025147616 | 7/2025 |
| WO | WO 2025188754 | 9/2025 |
| WO | WO 2025254900 | 12/2025 |
| WO | WO 2026060212 | 3/2026 |

OTHER PUBLICATIONS

Invitation to Pay Additional Fees in International Appln. No. PCT/US2025/018342, mailed on Sep. 9, 2025, 26 pages.

Albers et al., "Thrombectomy for stroke with selection by perfusion imaging." The New England journal of medicine 378.19, May 1, 2018, 1849-1850.

Allen et al., "Conditioned blood reperfusion markedly enhances neurologic recovery after prolonged cerebral ischemia" The Journal of Thoracic & Cardiovascular Surgery, vol. 126(6), Dec. 1, 2013, 1851-1858.

Allen et al., "Studies of isolated global brain ischaemia: I. A new large animal model of global brain ischaemia and its baseline perfusion studies" European journal of cardio-thoracic surgery 41.5, May 1, 2012, 1138-1146.

Allen et al., "Studies of isolated global brain ischaemia: II. Controlled reperfusion provides complete neurologic recovery following 30 min of warm ischaemia—the importance of perfusion pressure" European Journal of cardio—Thoracic Surgery, vol. 41 (5), May 1, 2012, 1147-1154.

Allen et al., "Studies of isolated global brain ischaemia: III. Influence of pulsatile flow during cerebral perfusion and its link to consistent full neurological recovery with controlled reperfusion following 30 min of global brain ischaemia" European Journal of Cardio-Thoracic Surgery, vol. 41 (5), May 1, 2012, 1155-1163.

Barksdale et al., "Mitochondrial viability in mouse and human postmortem brain." The FASEB Journal 24.9, Sep. 2010, 3590-3599.

Borjigin et al., "Surge of neurophysiological coherence and connectivity in the dying brain." Proceedings of the National Academy of Sciences 110.35, Aug. 27, 2013, 14432-14437.

Budde et al., "Neurite beading is sufficient to decrease the apparent diffusion coefficient after ischemic stroke." Proceedings of the National Academy of Sciences 107.32, Aug. 10, 2010, 14472-14477.

Chen et al., "Necrostatin-1 attenuates early brain injury after subarachnoid hemorrhage in rats by inhibiting necroptosis." Neuropsychiatric Disease and Treatment, Jul. 7, 2017, 1771-1782.

Drewes et al., "Glycolysis and the permeation of glucose and lactate in the isolated, perfused dog brain during anoxia and postanoxic recovery." Journal of Biological Chemistry 248.7, Apr. 10, 1973, 2489-2496.

Ehrlich et al., "Effect of hypothermia on cerebral blood flow and metabolism in the pig." The Annals of thoracic surgery 73.1, Jan. 1, 2002, 191-197.

Elmer et al., "Purification of hemoglobin by tangential flow filtration with diafiltration." Biotechnology progress 25.5, Sep. 2009, 1402-1410.

Elmer, "Expression, Purification, and Characterization of Mammalian and Earthworm Hemoglobins" Dissertation for the Degree of Doctor of Philosophy, Ohio State University, Chemical and Biomolecular Engineering Graduate Program, 2011, 184 pages.

Farahany et al., "The ethics of experimenting with human brain tissue" Apr. 2018, 429-432.

Greer et al., "Mechanisms of injury in hypoxic-ischemic encephalopathy: implications to therapy" Seminars in neurology, vol. 26. No. 04., Sep. 2006, 373-379.

Hayashi et al., "An enzymic reduction system for metmyoglobin and methemoglobin, and its application to functional studies of oxygen carriers." Biochimica et Biophysica Acta (BBA)—Protein Structure 310.2, Jun. 15, 1973, 309-316.

Horn et al., "Delayed neuronal death and delayed neuronal recovery in the human brain following global ischemia." Acta neuropathologica 85.1, Dec. 1992, 79-87.

(56) References Cited

OTHER PUBLICATIONS

Howells et al., "Different strokes for different folks: the rich diversity of animal models of focal cerebral ischemia." Journal of Cerebral Blood Flow & Metabolism 30.8, Aug. 2010, 1412-1431.
Hughes et al., "Full neurological recovery from profound (18.0 C) acute accidental hypothermia: successful resuscitation using active invasive rewarming techniques." Emergency Medicine Journal 24.7, Jul. 1, 2007, 511-512.
Iverson, "Troubleshooting tangential flow filtration." Chemical engineering progress 99.6, 2003, 54-56.
Jung et al., "Reperfusion and neurovascular dysfunction in stroke: from basic mechanisms to potential strategies for neuroprotection." Molecular neurobiology 41, Jun. 2010, 13 pages.
Keep et al., "Brain water content: a misunderstood measurement?" Translational stroke research 3, Jun. 2012, 5 pages.
Keyrouz et al., "Clinical review: Prevention and therapy of vasospasm in subarachnoid hemorrhage" Critical care 11, Aug. 14, 2007, 10 pages.
Kumar et al., "Mitochondrial dynamics following global cerebral ischemia" Molecular and Cellular Neuroscience 76, Oct. 1, 2016, 68-75.
Lam et al., "Intracellular pH reduction prevents excitotoxic and ischemic neuronal death by inhibiting NADPH oxidase." Proceedings of the National Academy of Sciences 110.46, Oct. 25, 2013, E4362-E4368.
Lee et al., "Brain tissue responses to ischemia." The Journal of clinical investigation 106.6, Sep. 15, 2000, 723-731.
Lee et al., "The changing landscape of ischaemic brain injury mechanisms." Nature 399.6738, Jun. 24, 1999, A7-A14.
Lind et al., "The use of pigs in neuroscience: modeling brain disorders." Neuroscience & Biobehavioral Reviews 31.5, Jan. 1, 2007, 728-751.
Marshall et al., "Regional citrate anticoagulation during simulated treatments of sustained low efficiency diafiltration." Nephrology 8.6, Dec. 2003, 302-310.
Moskowitz et al., "The science of stroke: mechanisms in search of treatments." Neuron 67.2, Jul. 29, 2010, 181-198.
Muzzelo et al., "Prolonging the shelf life of Lumbricus terrestris erythrocruorin for use as a novel blood substitute." Artificial Cells, Nanomedicine, and Biotechnology 46.1, Jan. 2, 2018, 39-46.
Naja et al., "Brain preservation with selective cerebral perfusion, moderate hypothermia and low flow rate." Journal of the Saudi Heart Association 24.4, Oct. 1, 2012, 285.
Offiah et al., "Post-mortem CT and MRI: appropriate post-mortem imaging appearances and changes related to cardiopulmonary resuscitation." The British journal of radiology 89.1058, Feb. 1, 2016, 8 pages.
Park et al., "Interleukin-10 endogenously expressed in microglia prevents lipopolysaccharide-induced neurodegeneration in the rat cerebral cortex in vivo." Experimental & molecular medicine 39.6, Dec. 2007, 812-819.
Ransom et al., "Axons get excited to death." Annals of neurology 65.2, Feb. 2009, 3 pages.
Savla et al., "Purification of lumbricus terrestris mega-hemoglobin for diverse oxygen therapeutic applications." ACS biomaterials science & engineering 6.9, Aug. 12, 2020, 4957-4968.
Sharma et al., "Cardiac arrest-induced regional blood-brain barrier breakdown, edema formation and brain pathology: a light and electron microscopic study on a new model for neurodegeneration and neuroprotection in porcine brain." Journal of neural transmission 118, Jan. 2011, 87-114.
Shin et al., "Microglia expressing interleukin-13 undergo cell death and contribute to neuronal survival in vivo." Glia 46.2, Apr. 15, 2004, 142-152.
Solenski et al., "Ultrastructural changes of neuronal mitochondria after transient and permanent cerebral ischemia." Stroke 33.3, Mar. 1, 2002, 816-824.
Sousa et al., "Molecular and cellular reorganization of neural circuits in the human lineage." Science 358.6366, Nov. 24, 2017, 19 pages.
Stacy et al., "Multimodality imaging approach for serial assessment of regional changes in lower extremity arteriogenesis and tissue perfusion in a porcine model of peripheral arterial disease." Circulation: Cardiovascular Imaging 7.1, Jan. 2014, 92-99.
Stephenson et al., "Development and evaluation of human ex vivo normothermic machine liver perfusion for viability testing and investigation of the role of TWEAK/Fn14 in ischaemia reperfusion injury", School of immunology & immunotherapy College of Medical and Dental Sciences, Jan. 1, 2018, 1-323.
Taunyane et al., "Preserved brain morphology after controlled automated reperfusion of the whole body following normothermic circulatory arrest time of up to 20 minutes." European Journal of Cardio-Thoracic Surgery 50.6, Dec. 1, 2016, 1025-1034.
Technologyreview.com [online], "Researchers are keeping pig brains alive outside the body" Apr. 25, 2018, retrieved on Mar. 19, 2025, retrieved from URL <https://www.technologyreview.com/2018/04/25/240742/researchers-are-keeping-pig-brains-alive-outside-the-body/>, 12 pages.
Timm et al., "Purification of Lumbricus terrestris erythrocruorin (LtEc) with anion exchange chromatography" Journal of Chromatography B 1150, Aug. 1, 2020, 21 pages.
Verwer et al., "Cells in human postmortem brain tissue slices remain alive for several weeks in culture." The FASEB journal 16.1, Jan. 2002, 54-60.
Vrselja et al., "Restoration of brain circulation and cellular functions hours post-mortem." Nature 568.7752, Apr. 18, 2019, 55 pages.
Zhang et al., "A universal scaling law between gray matter and white matter of cerebral cortex." Proceedings of the National Academy of Sciences 97.10, May 9, 2000, 5621-5626.
Zhu et al., "Stoichiometry of subunits and heme content of hemoglobin from the earthworm *Lumbricus terrestris*." Journal of Biological Chemistry 271.47, Nov. 1996, 29999-30006.
U.S. Appl. No. 18/690,785, Sestan et al., filed Mar. 11, 2024.
U.S. Appl. No. 19/009,835, Vrselja et al., filed Jan. 3, 2025.
U.S. Appl. No. 19/220,975, Vrselja, filed May 28, 2025.
Bodewes et al., "Oxygen Transport during Ex Situ Machine Perfusion of Donor Livers Using Red Blood Cells or Artificial Oxygen Carriers", International Journal of Molecular Sciences, vol. 22, No. 1, 235, Dec. 2020, 15 pages.
De Vries et al., "Transplantation of high-risk donor livers after resuscitation and viability assessment using a combined protocol of oxygenated hypothermic, rewarming and normothermic machine perfusion: study protocol for a prospective, single-arm study (DHOPE-COR-NMP trial)." BMJ open 9.8, Aug. 2019, e028596: 1-8.
Hogan et al., "Partial substitution of red blood cells with free hemoglobin solution does not improve maximal O2 uptake of working in situ dog muscle." Oxygen Transport to Tissue XVI. Boston, MA: Springer US, Jan. 1994, 375-378.
International Search Report and Written Opinion in International Appln. No. PCT/US2025/018342, mailed on Oct. 30, 2025, 31 pages.
International Search Report and Written Opinion in International Appln. No. PCT/US2025/031216, mailed on Sep. 22, 2025, 14 pages.
Jahr et al., "Does OxyVita, a new-generation hemoglobin-based oxygen carrier, or oxyglobin acutely interfere with coagulation compared with normal saline or 6% hetastarch? An ex vivo thromboelastography study." Journal of cardiothoracic and vascular anesthesia 22.1, Feb. 2008, 34-39.
Marchioro et al., "Extracorporeal perfusion for obtaining postmortem homografts", PMC, May 2011, 1-18.
Neya et al., "Hemoglobin Based Oxygen Carrying Solution Stability in Extracorporeal Circulation An In Vitro Evaluation and Implications for Clinical Use." ASAIO journal 44.3, May 1998, 166-170.
Vekemans et al., "Attempt to rescue discarded human liver grafts by end ischemic hypothermic oxygenated machine perfusion." Transplantation proceedings. vol. 43. No. 9. Elsevier, Nov. 2011, 3455-3459.
Andrijevic et al., "Cellular recovery after prolonged warm ischaemia of the whole body." Nature 608.7922, Aug. 2022, 405-412.
Barten et al., "Tau transgenic mice as models for cerebrospinal fluid tau biomarkers." Journal of Alzheimer's Disease 24.s2, Apr. 2011, 127-141.

(56) References Cited

OTHER PUBLICATIONS

Cho et al., "CX3CR1 protein signaling modulates microglial activation and protects against plaque-independent cognitive deficits in a mouse model of Alzheimer disease." Journal of Biological Chemistry 286.37, Sep. 2011, 32713-32722.
Cummings et al., "evoke and evoke+: design of two large-scale, double-blind, placebo-controlled, phase 3 studies evaluating efficacy, safety, and tolerability of semaglutide in early-stage symptomatic Alzheimer's disease." Alzheimer's research & therapy 17.1:14, Jan. 2025, 12 pages.
Daniele et al., "Brain vulnerability and viability after ischaemia." Nature Reviews Neuroscience 22.9, Sep. 2021, 553-572.
Doller et al., "Quality of Research Tools." Good Research Practice in Non-Clinical Pharmacology and Biomedicine. Cham: Springer International Publishing, Oct. 2019, 119-145.
Galatro et al., "Transcriptomic analysis of purified human cortical microglia reveals age-associated changes." Nature neuroscience 20.8, Aug. 2017, 1162-1171.
Gray et al., "Nucleoid size scaling and intracellular organization of translation across bacteria." Cell 177.6, May 2019, 1632-1648.
Hadžibegović et al., "Expression of leukocyte adhesion-related glycosyltransferase genes in acute coronary syndrome patients." Inflammation research 63.8, Aug. 2014, 629-636.
Harrison et al., "Activated RIC, a small GTPase, genetically interacts with the Ras pathway and calmodulin during *Drosophila* development." Developmental dynamics: an official publication of the American Association of Anatomists 232.3, Mar. 2005, 817-826.
Hlavacova et al., "Subchronic treatment with aldosterone induces depression-like behaviours and gene expression changes relevant to major depressive disorder." International Journal of Neuropsychopharmacology 15.2, Mar. 2012, 247-265.
Hölscher et al., "Glucagon-like peptide-1 class drugs show clear protective effects in Parkinson's and Alzheimer's disease clinical trials: a revolution in the making?." Neuropharmacology 253, Aug. 2024, 109952: 7 pages.
Holtman et al., "Induction of a common microglia gene expression signature by aging and neurodegenerative conditions: a co-expression meta-analysis." Acta neuropathologica communications 3.1, May 2015, 31: 18 pages.
Ištvanić et al., "Extended Eversion Carotid Endarterectomy: Computation of Hemodynamics." Annals of vascular surgery 29.8, Nov. 2015, 1598-1605.
Jove et al., "1079 Type I interferon regulation by USP18 is a key vulnerability in cancer." Nov. 2023, 1 page.
Kitazawa et al., "Blocking IL-1 signaling rescues cognition, attenuates tau pathology, and restores neuronal β-catenin pathway function in an Alzheimer's disease model." The Journal of Immunology 187.12, Dec. 2011, 6539-6549.
Kumar et al., "Identification of tomato root growth regulatory genes and transcription factors through comparative transcriptomic profiling of different tissues." Physiology and Molecular Biology of Plants 27.6, Jun. 2021, 1173-1189.
Macdonald et al., "Clazosentan to overcome neurological ischemia and infarction occurring after subarachnoid hemorrhage (CONSCIOUS-1): Randomized, double-blind, placebo-controlled phase 2 dose-finding trial." Stroke, 39(11), Nov. 2008, 3015-3021.
Macdonald et al., "Clazosentan, an endothelin receptor antagonist, in patients with aneurysmal subarachnoid haemorrhage undergoing surgical clipping: a randomised, double-blind, placebo-controlled phase 3 trial (CONSCIOUS-2)." The Lancet Neurology 10.7, Jul. 2011, 8 pages.
Macdonald et al., "Randomized trial of clazosentan in patients with aneurysmal subarachnoid hemorrhage undergoing endovascular coiling." Stroke, 43(6), Jun. 2012, 1463-1469.
Meulener et al., "*Drosophila* DJ-1 mutants are selectively sensitive to environmental toxins associated with Parkinson's disease." Current Biology 15.17, Sep. 2005, 1572-1577.
Möller et al., "Microglial biology in neuroinflammatory disease: pharmaco-industrial approach to target validation." Pathological Potential of Neuroglia: Possible New Targets for Medical Intervention, Sep. 2014, Chapter 9, 187-211.
Obradovic et al., "Assessment of the first and second generation antihistamines brain penetration and role of P-glycoprotein." Pharmaceutical research 24.2, Feb. 2007, 318-327.
Oh et al., "A cerebrospinal fluid synaptic protein biomarker for prediction of cognitive resilience versus decline in Alzheimer's disease." Nature medicine 31.5, May 2025, 1592-1603.
Paintdakhi et al., "Oufti: an integrated software package for high-accuracy, high-throughput quantitative microscopy analysis." Molecular microbiology 99.4, Feb. 2016, 767-777.
Parry et al., "The bacterial cytoplasm has glass-like properties and is fluidized by metabolic activity." Cell 156.1, Jan. 2014, 183-194.
Petruk et al., "Nimodipine treatment in poor-grade aneurysm patients: results of a multicenter double-blind placebo-controlled trial." Journal of neurosurgery 68.4, Apr. 1988, 505-517.
Pickard et al., "Effect of oral nimodipine on cerebral infarction and outcome after subarachnoid haemorrhage: British aneurysm nimodipine trial." British Medical Journal 298.6674, Mar. 1989, 636-642.
Salha et al., "Chemerin blood levels are associated with MRI measured volumes of abdominal adipose tissue compartments and lifestyle choices." Acta Clin Croat 56.4, Dec. 2017, 663-672.
Sankaranarayanan et al., "Passive immunization with phospho-tau antibodies reduces tau pathology and functional deficits in two distinct mouse tauopathy models." PloS one 10.5, May 2015, e0125614: 28 pages.
Shen et al., "De novo design of self-assembling helical protein filaments." Science 362.6415, Nov. 2018, 705-709.
Šram et al., "Epicardial adipose tissue is nonlinearly related to anthropometric measures and subcutaneous adipose tissue." International Journal of Endocrinology 2015.1, 2015, 456293: 6 pages.
Tashiro et al., "Central effects of fexofenadine and cetirizine: measurement of psychomotor performance, subjective sleepiness, and brain histamine H1-receptor occupancy using 11C-doxepin positron emission tomography." The Journal of Clinical Pharmacology 44.8, Aug. 2004, 890-900.
Trinh et al., "Induction of the phase II detoxification pathway suppresses neuron loss in *Drosophila* models of Parkinson's disease." Journal of Neuroscience 28.2, Jan. 2008, 465-472.
Vergouwen et al., "Cerebral infarction after subarachnoid hemorrhage contributes to poor outcome by vasospasm-dependent and-independent effects." Stroke 42.4, Apr. 2011, 924-929.
Vergouwen et al., "Definition of delayed cerebral ischemia after aneurysmal subarachnoid hemorrhage as an outcome event in clinical trials and observational studies: proposal of a multidisciplinary research group." Stroke 41(10), Oct. 2010, 2391-2395.
Vrselja et al., "Arterial tree asymmetry reduces cerebral pulsatility." Medical hypotheses 85.5, Nov. 2015, 622-627.
Vrselja et al., "Function of circle of Willis." Journal of Cerebral Blood Flow & Metabolism 34.4, Apr. 2014, 578-584.
Vrselja et al., "Penetrating arteries of the cerebral white matter: the importance of vascular territories of delivering arteries and completeness of circle of Willis." International journal of stroke 11.3, Apr. 2016, NP36-NP37.
Vrselja et al., "Restoration of brain circulation and cellular functions hours post-mortem." Nature 568.7752, Apr. 2019, 336-343.
Vrselja et al., "Transcardial gradient of adiponectin, interleukin-6 and tumor necrosis factor-α in overweight coronary artery disease patients." Cytokine 76.2, Dec. 2015, 321-327.
Vrselja, "Destined for destruction?." Science 366.6461, Oct. 2019, 2 pages.
Wes et al., "*C. elegans* odour discrimination requires asymmetric diversity in olfactory neurons." Nature 410.6829, Apr. 2001, 698-701.
Wes et al., "Myosin III (NINAC)" In Guidebook to the Cytoskeletal and Motor Proteins, Eds R. Vale and T. Kreis, Oxford University Press Inc., New York, 1999, 438-440.
Wes et al., "Next generation transcriptomics and genomics elucidate biological complexity of microglia in health and disease." Glia 64.2, Feb. 2016, 197-213.
Wes et al., "RIC, a calmodulin-binding Ras-like GTPase." The EMBO journal 15.21, Nov. 1996, 5839-5848.

(56) References Cited

OTHER PUBLICATIONS

Wes et al., "Targeting microglia for the treatment of Alzheimer's Disease." Glia 64.10, Oct. 2016, 23 pages.
Wes et al., "Tau overexpression impacts a neuroinflammation gene expression network perturbed in Alzheimer's disease." PloS one 9.8, Aug. 2014, e106050: 23 pages.
Wes et al., "Termination of phototransduction requires binding of the NINAC myosin III and the PDZ protein INAD." Nature neuroscience 2.5, May 1999, 447-453.
Wes et al., "TRPC1, a human homolog of a Drosophila store-operated channel." Proceedings of the National Academy of Sciences 92.21, Oct. 1995, 9652-9656.
Whitworth et al., "*Drosophila* models pioneer a new approach to drug discovery for Parkinson's disease." Drug discovery today 11.3-4, Feb. 2006, 119-126.
Whitworth et al., "Increased glutathione S-transferase activity rescues dopaminergic neuron loss in a *Drosophila* model of Parkinson's disease." Proceedings of the National Academy of Sciences 102.22, May 2005, 8024-8029.
Winnubst et al., "Reconstruction of 1,000 projection neurons reveals new cell types and organization of long-range connectivity in the mouse brain." Cell 179.1, Sep. 2019, 268-281.
Xiang et al., "Interconnecting solvent quality, transcription, and chromosome folding in *Escherichia coli*." Cell 184.14, Jul. 2021, 3626-3642.
Xu et al., "Retinal targets for calmodulin include proteins implicated in synaptic transmission." Journal of Biological Chemistry 273.47, Nov. 1998, 31297-31307.
Allen et al., "Cerebral arterial spasm- a controlled trial of nimodipine in patients with subarachnoid hemorrhage." New England Journal of Medicine 308.11, Mar. 1983, 619-624.
Bio-IT-World, "23rd Annual Bio It World" Brochure, Conference & Expo, Boston, MA, & Virtual, Apr. 15-17, 2024, 2 pages.
Chen et al., "P-glycoprotein limits the brain penetration of nonsedating but not sedating H1-antagonists." Drug Metabolism and Disposition 31.3, Mar. 2003, 312-318.
Etminan et al., "Unruptured intracranial aneurysms: development, rupture and preventive management." Nature Reviews Neurology 12.12, Dec 2016, 699-713.
Geraghty et al., "Delayed cerebral ischemia after subarachnoid hemorrhage: Beyond vasospasm" Current Neurology and Neuroscience Reports, 19(10), 2019, 75: 12 pages.
Kaur et al., "Specification of claustro-amygdalar and palaeocortical neurons and circuits." Nature 638.8050, Feb. 2025, 469-478.
Macdonald et al., "Spontaneous subarachnoid haemorrhage." The Lancet 389.10069, Feb. 2017, 655-666.
Macdonald, "Delayed neurological deterioration after subarachnoid haemorrhage." Nature Reviews Neurology 10.1, Jan. 2014, 44-58.
Reiner et al., "Neurochemistry and circuit organization of the lateral spiriform nucleus of birds: A uniquely nonmammalian direct pathway component of the basal ganglia." Journal of Comparative Neurology 532.5, May 2024, e25620: 47 pages.
Rowland et al., "Delayed cerebral ischaemia after subarachnoid haemorrhage: looking beyond vasospasm." British journal of anaesthesia 109.3, Sep. 2012, 315-329.
Shi et al., "A new anterograde trans-synaptic tracer based on Sindbis virus." Neural regeneration research 17.12, Dec 2022, 2761-2764.

* cited by examiner

PERFUSION AND METABOLIC RESTORATION OF ORGANS

CROSS-REFERENCE TO RELATED APPLICATIONS

This application claims the benefit of U.S. Provisional Application No. 63/562,094, filed on Mar. 6, 2024. The disclosure of the prior application is considered part of the disclosure of this application and is incorporated in its entirety into this application.

TECHNICAL FIELD

This specification relates to methods, systems, and compositions for perfusion and metabolic restoration of organs, in particular mammalian brains.

BACKGROUND

Perfusion in mammalian brains refers to the process of delivering perfusate (e.g., blood or an artificial perfusate) to the brain tissue to supply inputs, such as oxygen, glucose, and nutrients, while removing outputs, such as carbon dioxide and metabolic wastes. The process of perfusion is facilitated by a dense network of blood vessels, including arteries, capillaries, and veins, which collectively carry the cerebral blood flow.

SUMMARY

In one aspect, an ex-vivo brain perfusion system for perfusion of a brain includes a reservoir configured to receive perfusate, a housing configured to contain the brain, an arterial circuit configured to fluidly couple the reservoir to the brain, a venous circuit fluidly coupling the housing to the reservoir, and a syringe pump fluidly coupled to the reservoir and configured to introduce a therapeutic agent to the perfusate in the reservoir. The ex-vivo brain perfusion system is configured to perfuse the brain with the therapeutic agent to test at least one property of the therapeutic agent.

Implementations can include one or more of the following features in any combination.

In some implementations, the arterial circuit includes a fluid line fluidly coupling the reservoir to the brain, a pressure sensor configured to measure pressure along the fluid line, a flow sensor configured to measure a flow rate along the fluid line, and a pulse generation system configured to generate pulsatile flow of perfusate from the reservoir to the brain along the fluid line based on one or more signals generated by at least one of the pressure sensor or the flow sensor.

In certain implementations, the pulse generation system includes a pulse generator and an air supply system. The pulse generator includes a housing, a housing inlet, and a flexible diaphragm. The air supply system is fluidly coupled to the housing inlet of the pulse generator. The air supply system is configured to provide pressurized air into the housing inlet of the pulse generator based on one or more signals generated by at least one of the pressure sensor or the flow sensor, In some implementations, the pulse generation system is controlled based on an internal resistance of the brain detected by the pressure sensor.

In certain implementations, the syringe pump is configured to introduce the therapeutic agent into the reservoir according to a predefined release profile for the therapeutic agent.

In some implementations, the system includes a filtration system configured to filter the perfusate. The filtration system includes a dialyzer that includes an inlet port and an outlet port, an inlet line fluidly coupling the reservoir to the inlet port, an outlet line fluidly coupling the outlet port to the reservoir, and a pump configured to pump perfusate from the reservoir through the dialyzer. The dialyzer is configured to filter the perfusate.

In certain implementations, the system includes an in-line spectroscopy system configured to perform spectroscopy on the perfusate in real-time during a perfusion process.

In some implementations, the in-line spectroscopy system includes a spectroscopy chamber configured to receive perfusate from the reservoir or the venous circuit, a heat exchanger fluidly coupled to the spectroscopy chamber and configured to control a temperature of perfusate provided to the spectroscopy chamber, and a spectrometer configured to perform spectroscopy on perfusate in the spectroscopy chamber.

In certain implementations, the in-line spectroscopy system is configured to perform spectroscopy on one or more perfusate samples from the reservoir, and the syringe pump is configured to introduce the therapeutic agent into the reservoir according to a predefined release profile for the therapeutic agent based on spectroscopy data generated by performing spectroscopy on one or more perfusate samples from the reservoir using the in-line spectroscopy system.

In some implementations, the system further includes a filtration system configured to filter the therapeutic agent out of the perfusate, and the filtration system is configured to remove the therapeutic agent from the perfusate according to a predefined release profile for the therapeutic agent based on spectroscopy data generated by performing spectroscopy on one or more perfusate samples from the reservoir using the in-line spectroscopy system.

In certain implementations, the in-line spectroscopy system is configured to perform spectroscopy on one or more perfusate samples collected from the venous circuit to test the at least one property of the therapeutic agent.

In some implementations, the at least one property of the therapeutic agent includes whether the therapeutic agent passes through a blood-brain barrier of the brain.

In certain implementations, the in-line spectroscopy system is configured to perform Raman spectroscopy on the perfusate.

In certain implementations, the in-line spectroscopy system is configured to perform surface-enhanced Raman spectroscopy (SERS) on the perfusate.

In some implementations, the system includes a spectroscopy probe coupled to the housing, and the spectroscopy probe is configured to perform spectroscopy on tissue of the brain in the housing.

In certain implementations, the at least one property of the therapeutic agent is determined based on spectroscopy data generated by performing spectroscopy on the brain using the spectroscopy probe.

In some implementations, the spectroscopy probe is configured to perform Raman spectroscopy on the tissue of the brain.

In certain implementations, the spectroscopy probe is configured to perform surface-enhanced Raman spectroscopy (SERS) on the tissue of the brain.

In certain implementations, the at least one property of the therapeutic agent is a pharmacodynamic property of the therapeutic agent or pharmacokinetic property of the therapeutic agent.

In certain implementations, the at least one property of the therapeutic agent is an ability of the therapeutic agent to cross the blood-brain barrier of the brain.

In some implementations, the therapeutic agent includes at least one of a pharmaceutical compound, an antibody, a biologic, a viral vector, a lipid nanoparticle, or a peptide.

In another aspect, a method of testing at least one property of a therapeutic agent includes perfusing a brain with a perfusate using an ex-vivo perfusion system, introducing the therapeutic agent into the perfusate, while perfusing the brain, performing spectroscopy on tissue of the brain in real-time using the ex-vivo perfusion system to generate spectroscopy data, and determining, based on spectroscopy data, the at least one property of the therapeutic agent.

Implementations can include one or more of the following features in any combination.

In some implementations, performing spectroscopy on tissue of the brain in real-time while perfusing the brain using the ex-vivo perfusion system includes performing spectroscopy on tissue of the brain using a spectroscopy probe coupled to a brain housing of the ex-vivo perfusion system.

In certain implementations, determining, based on the spectroscopy data, the at least one property of the therapeutic agent includes determining whether the therapeutic agent has crossed a blood-brain barrier of the brain.

In some implementations, determining whether the therapeutic agent has crossed the blood-brain barrier of the brain includes analyzing the spectroscopy data to determine whether the therapeutic agent is present in the tissue of the brain, and in response to determining that the therapeutic agent is present in the tissue of the brain, determining that the therapeutic agent has crossed the blood-brain barrier of the brain.

In certain implementations, determining, based on the spectroscopy data, the at least one property of the therapeutic agent includes determining one or more molecules produced by the brain in response to the presence of the therapeutic agent.

In some implementations, determining one or more molecules produced by the brain in response to the presence of the therapeutic agent includes prior to introducing the therapeutic agent into the perfusate, performing spectroscopy on tissue of the brain to generate baseline spectroscopy data, and comparing the spectroscopy data generated after introducing the therapeutic agent with the baseline spectroscopy data.

In certain implementations, determining, based on the spectroscopy data, the at least one property of the therapeutic agent includes determining, based on the spectroscopy data, a concentration of the therapeutic agent in the tissue of the brain.

In some implementations, the method includes determining, based on the spectroscopy data, a release profile for the therapeutic agent that provides a desired uptake of the therapeutic agent by the brain.

In certain implementations, introducing the therapeutic agent into the perfusate includes introducing the therapeutic agent into the perfusate according to a first release profile, performing spectroscopy on the tissue of the brain in real-time while perfusing the brain using the ex-vivo perfusion system includes performing spectroscopy on the tissue of the brain while introducing the therapeutic agent into the perfusate according to the first release profile to generate first spectroscopy data; and the method further includes introducing the therapeutic agent into the perfusate according to a second release profile, perfusing a second brain while introducing the therapeutic agent into the perfusate according to the second release profile, performing spectroscopy on tissue of the second brain while introducing the therapeutic agent into the perfusate according to the second release profile to generate second spectroscopy data, and determining a release profile for the therapeutic agent by comparing the first spectroscopy data and the second spectroscopy data In some implementations, determining the release profile for the therapeutic agent includes comparing a first concentration of the therapeutic agent detected in the tissue of the brain based on the first spectroscopy data and a second concentration of the therapeutic agent detected in the tissue of the second brain based on the second spectroscopy data.

In certain implementations, the determined release profile for the therapeutic agent provides a desired uptake of the therapeutic agent by the brain.

In some implementations, performing spectroscopy on the tissue of the brain includes performing Raman spectroscopy on the tissue of the brain, and the spectroscopy data is Raman spectroscopy data.

In certain implementations, performing spectroscopy on the tissue of the brain includes performing surface-enhanced Raman spectroscopy (SERS) on the tissue of the brain, and the spectroscopy data is SERS data.

In some implementations, the therapeutic agent includes at least one of a pharmaceutical compound, an antibody, a biologic, a viral vector, a lipid nanoparticle, or a peptide.

In certain implementations, the at least one property of the therapeutic agent is a pharmacodynamic property of the therapeutic agent or pharmacokinetic property of the therapeutic agent.

In a further aspect, a method of testing at least one property of a therapeutic agent includes perfusing a brain with a perfusate using an ex-vivo perfusion system, introducing the therapeutic agent into the perfusate, while perfusing the brain, performing spectroscopy on the perfusate using an in-line spectroscopy system of the ex-vivo perfusion system to generate spectroscopy data, and determining, based on the spectroscopy data, the at least one property of the therapeutic agent.

Implementations can include one or more of the following features in any combination.

In some implementations, performing spectroscopy on the perfusate using an in-line spectroscopy system of the ex-vivo perfusion system includes operating a pump to deliver perfusate into a spectroscopy chamber of the in-line spectroscopy system, and controlling a spectrometer to perform spectroscopy on perfusate inside the spectroscopy chamber.

In certain implementations, performing spectroscopy on the perfusate using an in-line spectroscopy system of the ex-vivo perfusion system includes prior to delivering the perfusate into the spectroscopy chamber, adjusting a temperature of the perfusate to a predetermined temperature using a heat exchanger of the ex-vivo perfusion system.

In some implementations, performing spectroscopy on the perfusate using an in-line spectroscopy system of the ex-vivo perfusion system includes performing spectroscopy on used perfusate flowing out of the brain.

In certain implementations, determining, based on the spectroscopy data, the at least one property of the therapeutic agent includes determining whether the therapeutic agent has crossed a blood-brain barrier of the brain.

In some implementations, determining whether the therapeutic agent has crossed the blood-brain barrier of the brain includes analyzing the spectroscopy data generated by the in-line spectroscopy system to determine a concentration of the therapeutic agent in the used perfusate flowing out of the brain, comparing the concentration of the therapeutic agent in the used perfusate flowing out of the brain to a concentration of the therapeutic agent in fresh perfusate flowing into the brain, and in response to determining that the concentration of the therapeutic agent in the used perfusate flowing out of the brain is less than the concentration of the therapeutic agent in the fresh perfusate, determining that the therapeutic agent has crossed the blood-brain barrier of the brain.

In certain implementations, the method includes performing spectroscopy on the fresh perfusate using the in-line spectroscopy system to determine the concentration of the therapeutic agent in the fresh perfusate.

In some implementations, determining, based on the spectroscopy data, the at least one property of the therapeutic agent includes detecting one or more molecules produced by the brain in response to the presence of the therapeutic agent.

In certain implementations, detecting one or more molecules produced by the brain in response to the presence of the therapeutic agent includes prior to introducing the therapeutic agent into the perfusate, performing, using the in-line spectroscopy system, spectroscopy on fresh perfusate flowing to the brain to generate baseline spectroscopy data, and comparing the spectroscopy data generated by performing spectroscopy on the used perfusate with the baseline spectroscopy data.

In some implementations, introducing the therapeutic agent includes performing spectroscopy on fresh perfusate flowing into the brain using the in-line spectroscopy system to determine a concentration of the therapeutic agent in the fresh perfusate; and controlling the ex-vivo perfusion system to introduce the therapeutic agent into the fresh perfusate or remove the therapeutic agent from the fresh perfusate at a particular rate based on the concentration of the therapeutic agent in the fresh perfusate.

In certain implementations, controlling the ex-vivo perfusion system to introduce the therapeutic agent into the fresh perfusate or remove the therapeutic agent from the fresh perfusate at a particular rate based on the concentration of the therapeutic agent in the fresh perfusate includes controlling a syringe pump of the ex-vivo perfusion system to introduce the therapeutic agent into the fresh perfusate at the particular rate determined based on the concentration of the therapeutic agent in the fresh perfusate.

In some implementations, controlling the ex-vivo perfusion system to introduce the therapeutic agent into the fresh perfusate or remove the therapeutic agent from the fresh perfusate at a particular rate based on the concentration of the therapeutic agent in the fresh perfusate includes controlling a filtration system of the ex-vivo perfusion system to remove the therapeutic agent from the fresh perfusate at the particular rate determined based on the concentration of the therapeutic agent in the fresh perfusate.

In certain implementations, controlling the ex-vivo perfusion system to introduce the therapeutic agent into the fresh perfusate or remove the therapeutic agent from the fresh perfusate at a particular rate based on the concentration of the therapeutic agent in the fresh perfusate includes controlling the ex-vivo perfusion system to introduce the therapeutic agent into the fresh perfusate or remove the therapeutic agent from the fresh perfusate according to a predefined release profile.

In some implementations, the method includes determining, based on the spectroscopy data generated by the in-line spectroscopy system, a release profile for the therapeutic agent that provides a desired uptake of the therapeutic agent by the brain.

In certain implementations, introducing the therapeutic agent into the perfusate includes introducing the therapeutic agent into the perfusate according to a first release profile; performing spectroscopy on perfusate solution while perfusing the brain includes performing spectroscopy on used perfusate flowing out of the brain while introducing the therapeutic agent into the perfusate according to the first release profile to generate first spectroscopy data; and the method further includes introducing the therapeutic agent into the perfusate according to a second release profile, perfusing a second brain while introducing the therapeutic agent into the perfusate according to the second release profile, performing spectroscopy on used perfusate flowing out of the second brain using the in-line spectroscopy system while introducing the therapeutic agent into the perfusate according to the second release profile to generate second spectroscopy data, and determining a release profile for the therapeutic agent by comparing the first spectroscopy data and the second spectroscopy data.

In some implementations, determining a release profile for the therapeutic agent includes comparing a first concentration of the therapeutic agent detected based on the first spectroscopy data and a second concentration of the therapeutic agent detected based on the second spectroscopy data.

In certain implementations, the determined release profile for the therapeutic agent provides a desired uptake of the therapeutic agent by the brain.

In some implementations, the at least one property of the therapeutic agent is a pharmacodynamic property of the therapeutic agent or pharmacokinetic property of the therapeutic agent.

In certain implementations, performing spectroscopy on the perfusate while perfusing the brain using the in-line spectroscopy system includes performing Raman spectroscopy on the perfusate using the in-line spectroscopy system; and the spectroscopy data is Raman spectroscopy data.

In certain implementations, performing spectroscopy on the perfusate includes performing surface-enhanced Raman spectroscopy (SERS) on the perfusate, and the spectroscopy data is SERS data.

In some implementations, the therapeutic agent includes at least one of a pharmaceutical compound, an antibody, a biologic, a viral vector, a lipid nanoparticle, or a peptide.

In a further aspect, a method of perfusing a brain using an ex-vivo perfusion system to reduce internal resistance of the brain includes fluidly coupling the brain to a fluid line of the ex-vivo perfusion system, controlling a pulse generation system to provide pulsatile flow of the perfusate to the brain along the fluid line at an initial pressure, adjusting the pulsatile flow of the perfusate to increase a pressure along the fluid line until a flow rate of perfusate along the fluid line corresponds to a threshold flow rate, and in response to detecting that the flow rate of perfusate along the fluid line corresponds to the threshold flow rate, controlling the pulse generation system to maintain the threshold flow rate of perfusate along the fluid line.

Implementations can include one or more of the following features in any combination.

In some implementations, the pulse generation system includes a pulse generator and an air supply system fluidly coupled to the pulse generator, and adjusting the pulsatile flow of the perfusate to increase the pressure along the fluid line until a flow rate of perfusate along the fluid line corresponds to a threshold flow rate includes controlling the pulse generation system to increase the pressure along the fluid line.

In certain implementations, controlling the pulse generation system to increase the pressure along the fluid line includes controlling the air supply system to supply pressurized air to pulse generator at a particular frequency determined based on signals generated by a pressure sensor positioned along the fluid line.

In some implementations, detecting that the flow rate of perfusate along the fluid line corresponds to the threshold flow rate includes measuring the flow rate of perfusate along the fluid line using a flow sensor positioned along the fluid line.

In certain implementations, the method includes controlling a resistance valve positioned along the fluid line based on the pressure detected along the fluid line.

In some implementations, the method includes gradually increasing a temperature of the perfusate to a threshold temperature using a heat exchanger of the ex-vivo perfusion system.

In certain implementations, the method includes gradually increasing a concentration of oxygen in the perfusate to a threshold concentration using a gas mixer of the ex-vivo perfusion system.

In a further aspect, a pulse generation system configured to provide pulsatile flow of perfusate to a brain coupled to an ex-vivo perfusion system includes a pulse generator and an air supply system. The pulse generator includes a housing configured to receive perfusate from the ex-vivo perfusion system, an air inlet, and a flexible diaphragm. The air supply system is fluidly coupled the air inlet of the pulse generator. The air supply system is configured to provide pressurized air into the air inlet of the pulse generator based on one or more signals generated by at least one of a pressure sensor or a flow sensor downstream of the pulse generator.

Implementations can include one or more of the following features in any combination.

In some implementations, the pulse generator includes a perfusate inlet configured to be fluidly connected to a fluid line of the ex-vivo perfusion system upstream of the brain, a sensor block outlet configured to be fluidly coupled to a sensor block of the ex-vivo perfusion system, and an organ line outlet configured to be fluidly coupled to the brain.

In certain implementations, the pulse generator is configured to prevent flow of perfusate through the organ line outlet when the flexible diaphragm is in an unflexed position.

In some implementations, the pulse generator is configured to direct all of the perfusate in the housing to flow through the sensor block outlet when the flexible diaphragm is in an unflexed position.

In certain implementations, the pulse generator is configured to force a portion of the perfusate in the housing through the organ line outlet when the flexible diaphragm is in a flexed position.

In some implementations, the air supply system is configured to supply pressurized air to pulse generator at a particular frequency determined based on signals generated by a pressure sensor positioned along a fluid line extending between the pulse generator and the brain.

In some implementations, the air supply system includes an air source, a first electronic pressure regulator fluidly coupled to the air source, and a second electronic pressure regulator fluidly coupled to the first electronic pressure regulator. The first electronic pressure regulator is configured to regulate a pressure of a first stream of air provided by the air source. The second electronic pressure regulator is configured to regulate a pressure of a second stream of air provided by the first electronic pressure regulator.

In certain implementations, the second electronic pressure regulator has a smaller tolerance range than the first electronic pressure regulator.

In some implementations, the system includes a first pressure sensor coupled to a fluid line downstream of the first electronic pressure regulator and upstream of the second electronic pressure regulator, and the first electronic pressure regulator is controlled based on one or more signals generated by the first pressure sensor.

In certain implementations, the system includes a second pressure sensor coupled to the fluid line downstream of the second electronic pressure regulator, and the second electronic pressure regulator is controlled based on one or more signals generated by the second pressure sensor.

In a further aspect, an ex-vivo perfusion system for perfusion of a mammalian organ includes a reservoir configured to receive perfusate, a housing configured to contain the mammalian organ, an arterial circuit configured to fluidly couple the reservoir to the mammalian organ, a venous circuit fluidly coupling the housing to the reservoir, and a syringe pump fluidly coupled to the reservoir and configured to introduce a therapeutic agent to the perfusate in the reservoir. The ex-vivo perfusion system is configured to perfuse the mammalian organ with the therapeutic agent to test at least one property of the therapeutic agent.

Implementations can include one or more of the following features in any combination.

In some implementations, the mammalian organ is a human organ.

In some implementations, the mammalian organ is a brain.

In certain implementations, the mammalian organ is a human brain.

In some implementations, the therapeutic agent includes at least one of a pharmaceutical compound, an antibody, a biologic, a viral vector, a lipid nanoparticle, or a peptide.

In a further aspect, a method of testing at least one property of a therapeutic agent includes perfusing a mammalian organ with a perfusate using an ex-vivo perfusion system, introducing the therapeutic agent into the perfusate, while perfusing the mammalian organ, performing spectroscopy on tissue of the mammalian organ in real-time using the ex-vivo perfusion system to generate spectroscopy data, and determining, based on spectroscopy data generated by the spectroscopy, the at least one property of the therapeutic agent.

Implementations can include one or more of the following features in any combination.

In some implementations, the mammalian organ is a human organ.

In certain implementations, the mammalian organ is a brain.

In some implementations, the mammalian organ is a human brain.

In some implementations, the therapeutic agent includes at least one of a pharmaceutical compound, an antibody, a biologic, a viral vector, a lipid nanoparticle, or a peptide.

In a further aspect, a method of testing at least one property of a therapeutic agent includes perfusing a mammalian organ with a perfusate using an ex-vivo perfusion system, introducing the therapeutic agent into the perfusate, while perfusing the mammalian organ, performing spectroscopy on perfusate solution using an in-line spectroscopy system of the ex-vivo perfusion system to generate spectroscopy data, and determining, based on the spectroscopy data, the at least one property of the therapeutic agent.

Implementations can include one or more of the following features in any combination.

In some implementations, the mammalian organ is a human organ.

In certain implementations, the mammalian organ is a brain.

In some implementations, the mammalian organ is a human brain.

In some implementations, the therapeutic agent includes at least one of a pharmaceutical compound, an antibody, a biologic, a viral vector, a lipid nanoparticle, or a peptide.

In a further aspect, a pulse generation system configured to provide pulsatile flow of perfusate to a mammalian organ coupled to an ex-vivo perfusion system includes a pulse generator and an air supply system. The pulse generator includes a housing configured to receive perfusate from the ex-vivo perfusion system, an air inlet, and a flexible diaphragm. The air supply system is fluidly coupled the air inlet of the pulse generator. The air supply system is configured to provide pressurized air into the air inlet of the pulse generator based on one or more signals generated by at least one of a pressure sensor or a flow sensor downstream of the pulse generator Implementations can include one or more of the following features in any combination.

In some implementations, the mammalian organ is a human organ.

In certain implementations, the mammalian organ is a brain.

In some implementations, the mammalian organ is a human brain.

In another aspect, a method of testing at least one property of a therapeutic agent includes perfusing a brain with a perfusate using an ex-vivo perfusion system, introducing the therapeutic agent into the perfusate, testing tissue of the brain using the ex-vivo perfusion system to generate test data, and determining, based on the test data, the at least one property of the therapeutic agent.

Implementations can include one or more of the following features in any combination.

In certain implementations, testing the tissue of the brain comprises performing one or more of spectroscopy, gene sequencing, cytokine analysis, anti-body analysis, genomic analysis, transcriptomic analysis, proteomic analysis, or metabolomic analysis.

In some implementations, the therapeutic agent comprises one or more of a pharmaceutical compound, an antibody, a biologic, a viral vector, a lipid nanoparticle, or a peptide.

In certain implementations, determining, based on the test data, the at least one property of the therapeutic agent comprises determining whether the therapeutic agent has crossed a blood-brain barrier of the brain.

In a further aspect, a method of testing at least one property of a therapeutic agent includes perfusing a brain with a perfusate using an ex-vivo perfusion system, introducing the therapeutic agent into the perfusate, testing the perfusate using a test device of the ex-vivo perfusion system to generate test data, and determining, based on the test data, the at least one property of the therapeutic agent.

Implementations can include one or more of the following features in any combination.

In certain implementations, the test device comprises one or more of a spectroscopy device, a gene sequencing device, a cytokine analysis device, an anti-body analysis device, a genomic analysis device, a transcriptomic analysis device, a proteomic analysis device, or a metabolomic analysis device.

In some implementations, the therapeutic agent comprises one or more of a pharmaceutical compound, an antibody, a biologic, a viral vector, a lipid nanoparticle, or a peptide.

In some implementations, determining, based on the test data, the at least one property of the therapeutic agent comprises determining whether the therapeutic agent has crossed a blood-brain barrier of the brain.

In an additional aspect, a method of testing at least one property of a therapeutic agent includes perfusing a mammalian organ with a perfusate using an ex-vivo perfusion system, introducing the therapeutic agent into the perfusate, testing tissue of the mammalian organ using the ex-vivo perfusion system to generate test data, and determining, based on test data, the at least one property of the therapeutic agent.

Implementations can include one or more of the following features in any combination.

In certain implementations, testing the tissue of the mammalian organ comprises performing one or more of spectroscopy, gene sequencing, cytokine analysis, anti-body analysis, genomic analysis, transcriptomic analysis, proteomic analysis, or metabolomic analysis.

In some implementations, the therapeutic agent comprises one or more of a pharmaceutical compound, an antibody, a biologic, a viral vector, a lipid nanoparticle, or a peptide.

In some implementations, the mammalian organ is a human organ.

In certain implementations, the mammalian organ is a brain.

In some implementations, the mammalian organ is a human brain.

In another aspect, a method of testing at least one property of a therapeutic agent includes perfusing a mammalian organ with a perfusate using an ex-vivo perfusion system, introducing the therapeutic agent into the perfusate, testing the perfusate to generate test data, and determining, based on the test data, the at least one property of the therapeutic agent.

Implementations can include one or more of the following features in any combination.

In certain implementations, testing the perfusate comprises performing one or more of spectroscopy, gene sequencing, cytokine analysis, anti-body analysis, genomic analysis, transcriptomic analysis, proteomic analysis, or metabolomic analysis.

In some implementations, the therapeutic agent comprises one or more of a pharmaceutical compound, an antibody, a biologic, a viral vector, a lipid nanoparticle, or a peptide.

In some implementations, the mammalian organ is a human organ.

In certain implementations, the mammalian organ is a brain.

In some implementations, the mammalian organ is a human brain.

In a further aspect, a method performed by one or more computers includes receiving test data that is generated by a test device of an ex-vivo brain perfusion system. The test data relates to (i) tissue of a brain being perfused by the ex-vivo brain perfusion system, or (ii) perfusate that has passed through the tissue of the brain being perfused by the ex-vivo brain perfusion system. The method further includes processing a model input that comprises the test data using a machine learning model, in accordance with values of a set of machine learning model parameters, to generate a model output that comprises a prediction characterizing the brain, and outputting the prediction characterizing the brain.

Implementations can include one or more of the following features in any combination.

In some implementations, the prediction characterizing the brain includes one or more of: a prediction for whether the brain is currently experiencing swelling; or a prediction for whether the brain is currently infected; or a prediction for a reaction of the brain to a therapeutic agent being provided to the brain by the ex-vivo brain perfusion system.

In certain implementations, the machine learning model includes one or more of: a neural network, or a random forest, or a support vector machine.

In some implementations, the model input comprises test data captured at multiple time points in a sequence of time points.

In another aspect, a system includes one or more computers and one or more storage devices communicatively coupled to the one or more computers, wherein the one or more storage devices store instructions that, when executed by the one or more computers, cause the one or more computers to perform operations comprising: receiving test data that is generated by a test device of an ex-vivo brain perfusion system; processing a model input that comprises the test data using a machine learning model, in accordance with values of a set of machine learning model parameters, to generate a model output that comprises a prediction characterizing the brain, and outputting the prediction characterizing the brain. The test data relates to (i) tissue of a brain being perfused by the ex-vivo brain perfusion system, or (ii) perfusate that has passed through the tissue of the brain being perfused by the ex-vivo brain perfusion system.

In an additional aspect, one or more non-transitory computer storage media store instructions that when executed by one or more computers cause the one or more computers to perform operations comprising: receiving test data that is generated by a test device of an ex-vivo brain perfusion system; processing a model input that comprises the test data using a machine learning model, in accordance with values of a set of machine learning model parameters, to generate a model output that comprises a prediction characterizing the brain, and outputting the prediction characterizing the brain. The test data relates to (i) tissue of a brain being perfused by the ex-vivo brain perfusion system, or (ii) perfusate that has passed through the tissue of the brain being perfused by the ex-vivo brain perfusion system.

Implementations can include one or more of the following advantages. The perfusion systems and methods described herein enable restoration and preservation of a human brain, including normal cellular activity of the brain, for up to 24 hours or longer post-mortem. As a result, cellular and metabolic health of the brain can be preserved in the brain.

In addition, human brains that are perfused using the perfusion systems and methods described herein can be tested to study disease mechanisms within the human brain. For example, brains exhibiting a particular disease or condition can be exposed to certain therapeutic agents (e.g., pharmaceutical compounds, antibodies, biologics, viral vectors, lipid nanoparticles, peptides, etc.) during perfusion using the perfusion systems and methods described herein, and the response of the brains to the therapeutic agents can be studied by performing testing on the brain and/or the perfusate in real-time during the perfusion process. In addition, brains can be mechanically or chemically altered prior to perfusion in order to simulate a particular disease mechanism. The mechanically or chemically altered brains can be exposed to certain therapeutic agents during perfusion using the perfusion systems and methods described herein, and the response of the brains to the therapeutic agents can be studied by performing testing on the brain and/or the perfusate in real-time during the perfusion process. In addition, individual mechanisms associated with particular brain diseases can be studied using the systems and methods described herein. For example, brains exhibiting a particular disease or altered to simulate the disease can be analyzed using the systems and methods described herein to identify and study particular compounds or molecules generated by the brain related to the disease or particular chemical or electrical activity of the brain related to disease.

The perfusion systems and methods described herein can also be used to determine the pharmacokinetics of therapeutic agents (also referred to herein as "drugs"), the pharmacodynamics of therapeutic agents, the likely efficacy of particular therapeutic agents on treating targeted diseases, and potential side effects that may result from administration of therapeutic agents. The perfusion systems and methods described herein can also be used to determine whether a therapeutic agent is able to cross the blood-brain barrier of the brain. As a result, the safety and efficacy of potential new drugs can be tested using the perfusate systems and methods described herein to accurately determine their likely effectiveness in treating the targeted diseases in humans without requiring administration of the drug to humans. For example, perfusion systems and techniques described herein provide a tightly controlled arterial input and high-dimension data sampling that allows investigators to expose the brain to any therapeutic modality in order to generate real and precise human multi-omic brain response networks required for phenotype-based drug discovery. The perfusion systems and techniques described herein can also provide highly differentiated capacity to determine safety profiles, pharmacological properties, and target engagement validation and deconvolution of desired therapeutics. The systems and methods described herein can be used to study the effects of drugs on the brain using non-diseased brains, diseased brains, or modeled brains.

The perfusion systems and techniques described herein can also be used to study mechanisms and potential treatments for brain injuries.

The accuracy of the data related to the brain captured using the systems and methods described herein has a high level of accuracy (e.g., a high signal to noise ratio) due to the isolation of the brain and the lack of influence from peripheral organs. The response of the brain to a particular stimulus can be isolated and determined with high levels of accuracy.

The details of certain implementations are set forth in the accompanying drawings and the description below. Other aspects, features, and advantages will be apparent from the description and drawings, and from the claims.

BRIEF DESCRIPTION OF DRAWINGS

Like references symbols in the various drawings indicate like elements.

DETAILED DESCRIPTION

This specification generally describes devices, systems, and methods for ex-vivo perfusion of mammalian organs. In particular, this specification describes devices, systems, and methods for perfusing a human brain for ex-vivo restoration and preservation of the human brain, including normal cellular activity of the brain, for 24 hours or longer post-mortem or after global ischemia. In addition, this specification describes devices, systems, and methods for performing pharmacokinetic modeling and pharmacological testing using a perfused brain.

An example of an electromechanical perfusion device is described in: Zvonimir Vrselja et al., "Restoration of brain circulation and cellular functions hours postmortem," *Nature,* 2019 April; 568 (7752), which is incorporated by reference herein. Examples of electromechanical perfusion devices and artificial perfusion experiments are also described in U.S. patent application Ser. No. 16/967,925, which is incorporated by reference herein.

Figure 1:
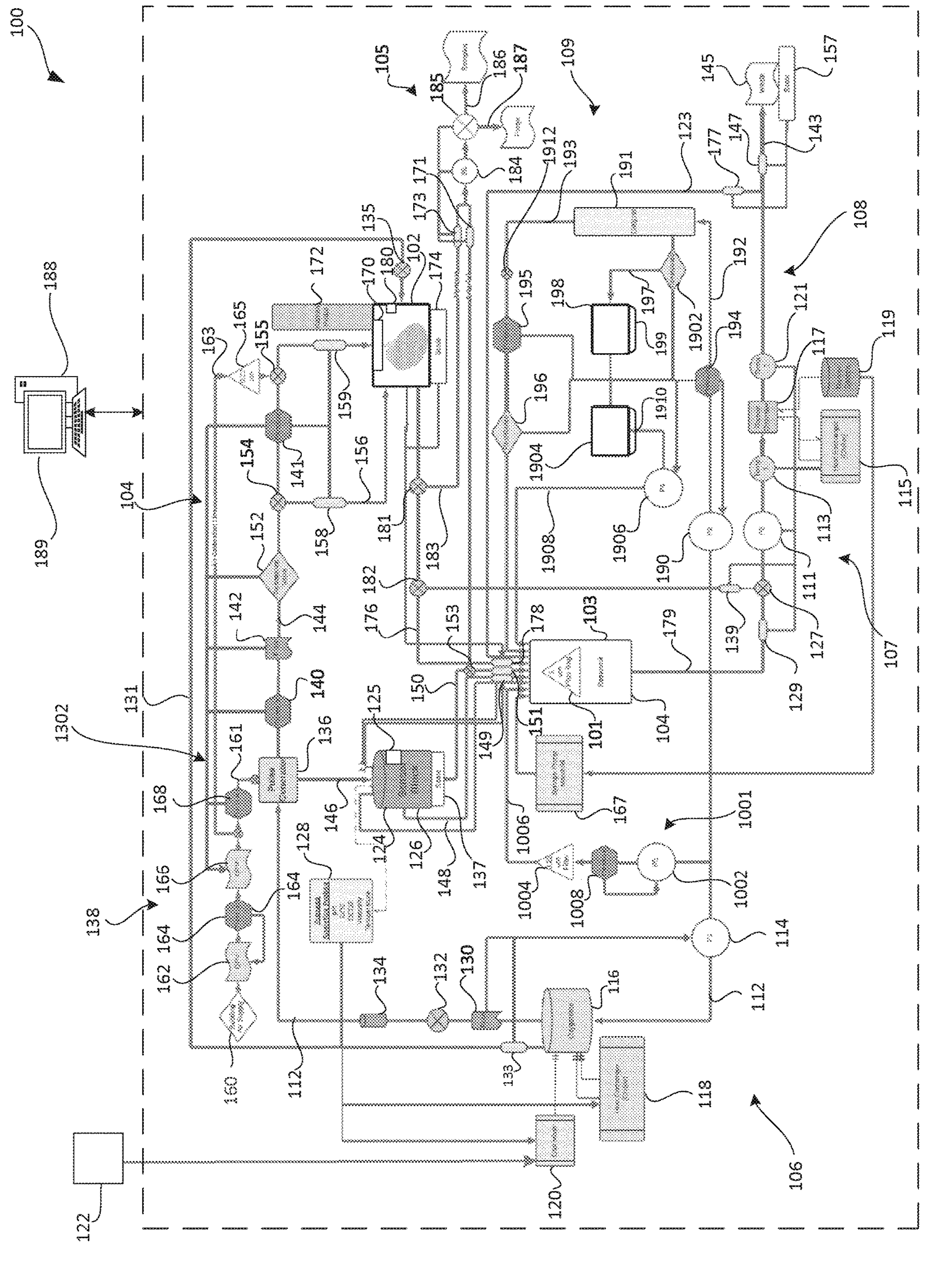
FIG. 1 is a schematic illustration of a system for ex-vivo perfusion of a mammalian brain.
Figure 13:
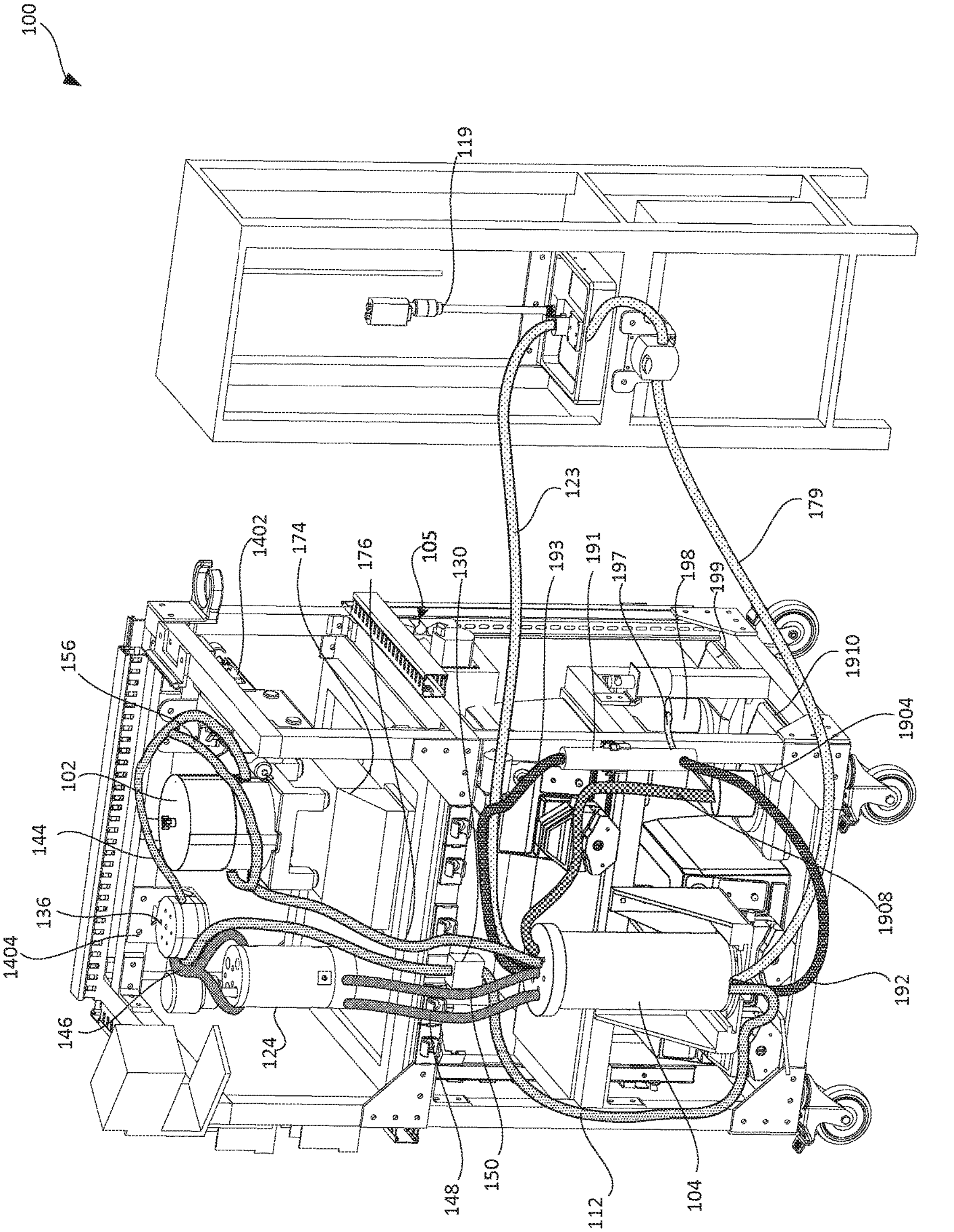
FIG. 13 is a perspective view of the example system of FIG. 1.
Figure 15:
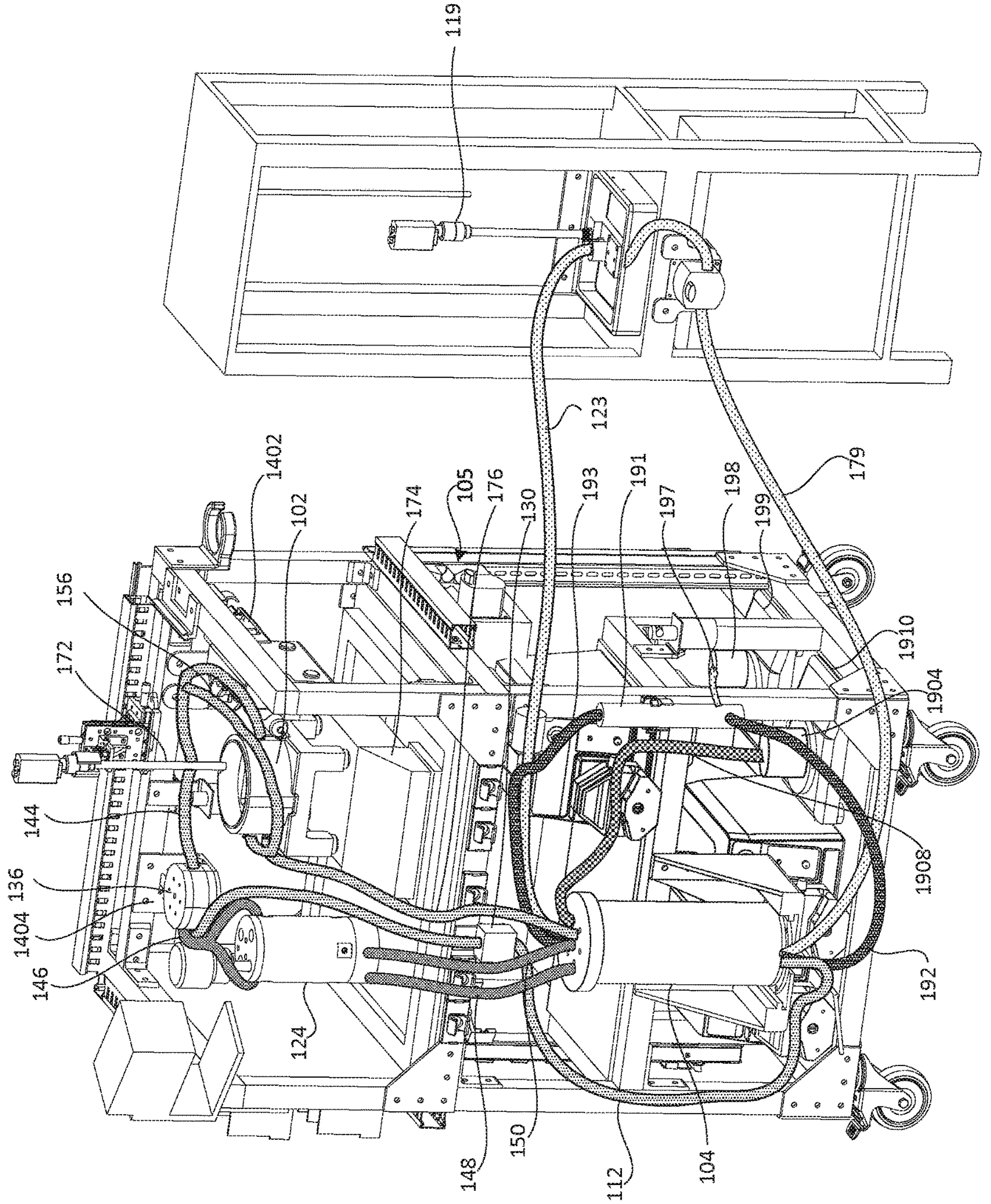
FIG. 15 is a perspective view of the example system of FIG. 1 with an example Raman probe positioned over the brain housing.

FIGS. 1, 13, and 15 depict an example perfusion system 100 for perfusion, restoration, and preservation of a human brain 110. The perfusion system 100 includes a brain housing 102 that is configured to enclose a human brain 110 and a perfusate reservoir 104 that is configured to contain a perfusate solution (also referred to herein as "perfusate"). As will be described in further detail herein, the perfusate contained within the perfusate reservoir 104 is configured to perfuse and restore a human brain 110 contained inside the brain housing 102.

The brain housing 102 is fluidly connected to the perfusate reservoir 104 through an arterial circuit 106 and a venous circuit 108, which together form a closed-loop fluid circuit to circulate a synthetic acellular perfusate under a pulsatile flow. The arterial circuit 106 includes an arterial fluid line 112 and an organ line 144 fluidly coupling the perfusate reservoir 104 to the brain housing 102, and the fresh perfusate contained within the perfusate reservoir 104 is provided to brain 110 inside the brain housing 102 along the arterial fluid line 112 and the organ line 144. The arterial circuit 106 also includes a flow pump 114 positioned along the arterial fluid line 112 between the perfusate reservoir 104 and an oxygenator 116. The flow pump 114 is a peristaltic pump configured to pump fresh perfusate from the perfusate reservoir 104 to the oxygenator 116. The peristaltic flow pump 114 is configured to minimize shear of the perfusate as it is pumped along the arterial fluid line 112. In some implementations, the flow pump 114 is configured to flow the perfusate to the oxygenator 116 at a rate of 400 mL/minute.

The oxygenator 116 includes a heat exchanger 118 and a gas mixer 120. The heat exchanger 118 includes one or more metal heat exchanging coils configured to regulate the temperature of the perfusate received by the oxygenator 116. As will be described in further detail herein, the arterial circuit 106 includes a sensor block 124 with sensor probes 128 configured to measure certain characteristics of the fresh perfusate flowing through the arterial circuit 106, including the temperature of the fresh perfusate, and the heat exchanger 118 is configured to adjust the temperature of the perfusate flowing through the heat exchanger 118 based on the temperature of the perfusate detected by the sensor block 124. For example, the heat exchanger 118 is configured to adjust the temperature of the perfusate to be within a predetermined range of temperature based on the temperature signals generated by the sensor block 124. For example, as will be described in further detail herein, at the beginning of treatment, the temperature of the perfusate in the system 100 is in a range of 16° C. to 20° C. and the heat exchanger 118 can be used to increase the temperature of the perfusate at a controlled rate at the beginning of the perfusion process.

In some implementations, the heat exchanger 118 is configured to increase to temperature of the perfusate to be within a range of 35° C. to 37° C.

The gas mixer 120 of the oxygenator 116 is fluidly coupled to and receives one or more gasses from a gas source 122, and the gas mixer 120 is configured to dissolve the one or more gasses into the perfusate flowing through the oxygenator 116. The gas mixer 120 includes three inlets fluidly coupled to the gas source 122. A first inlet of the gas mixer 120 is configured to be fluidly coupled to a source of $O_2$, a second inlet of the gas mixer 120 is configured to be coupled to a source of $N_2$, and a third inlet of the gas mixer 120 is configured to be coupled to a source of $CO_2$. The gas mixer 120 is controlled based on one or more signals generated by the sensor block 124 indicating the dissolved gas levels of the perfusate within the sensor block 124. For example, the sensor block 124 can generate one or more signals indicating the dissolved oxygen concentration of the perfusate within the sensor block 124, the dissolved nitrogen concentration of the perfusate within the sensor block 124, and the dissolved carbon dioxide concentration of the perfusate within the sensor block 124 and, based on the signals, the gas mixer 120 adjusts the amount of oxygen, nitrogen, and/or carbon dioxide provided to the perfusate within the oxygenator 116 in order to control the dissolved oxygen concentration, the dissolved nitrogen concentration, and the dissolved carbon dioxide concentration of the perfusate to be within a predetermined range. For example, based on the signals generated by the sensor block 124, the gas mixer 120 generates commands to control internal gas valves of the gas mixer 120 to control the flow rate of gas into each respective inlet of the gas mixer 120 in order to control the amount and rate that each gas ($O_2$, $N_2$, and $CO_2$) are provided to the oxygenator 116.

In addition, the gas mixer 120 monitors the pressure and flow rate of gas provided from the gas mixer 120 to the oxygenator 116. In some implementations, the gas mixer 120 maintains the flow rate of gas from the gas mixer 120 to the oxygenator 116 at approximately 700 mL/minute. As described herein, in some implementations, the flow pump 114 is configured to flow the perfusate to the oxygenator 116 at a rate of 400 mL/minute. By flowing the gas into the oxygenator 116 at a rate of 700 mL/minute and simultaneously flowing perfusate into the oxygenator 116 at a rate of 400 mL/minute, a predetermined ventilation/perfusion coefficient of 700/400 can be maintained throughout the perfusion process. By adjusting the flow rate of each of the gasses flowing into the gas mixer 120 while maintaining the rate of gas flowing out of the gas mixer 120 into oxygenator 116, $the_2$ gas mixer 120 can control and adjust the concentration of each of the respective gasses within the perfusate while maintaining the predetermined ventilation/perfusion coefficient.

The concentration of the $CO_2$, $N_2$, and $O_2$ within the perfusate are maintained within physiological limits, as determined based on the concentration detected using the sensor probes 128 in the sensor block 124. In some implementations, the gas mixer 120 and oxygenator 116 are controlled based on an alpha stat approach to maintain the blood gas concentrations within normal, physiological limits. In some implementations, the partial pressure of $CO_2$ within the partial pressure of the $CO_2$ within the perfusate is maintained at a partial pressure of approximately 400 mmHg during the perfusion process. In some implementations, the partial pressure of $O_2$ in the perfusate is maintained at 450 mmHg during the perfusion process. As will be described in further detail herein, at the beginning of a perfusion procedure, the temperature of the perfusate is gradually increased by the heat exchanger 118 and the $O_2$ concentration of the perfusate is gradually increased by the gas mixer 120 until a target temperature and $O_2$ concentration for the perfusate are reached, as detected based on the sensor probes 128 in the sensor block 124. For example, at the beginning of perfusion, the partial pressure of $O_2$ in the perfusate is 200 mmHg and the gas mixer 120 and oxygenator 116 are controlled to gradually increase the partial pressure of $O_2$ in the perfusate to 450 mmHg. By gradually increasing the temperature and the $O_2$ concentration of the perfusate, the internal resistance of the brain 110 is decreased, which results in improved perfusion of the brain 110 and reduced risk of injury to the brain 110.

A shunt line 131 is coupled to and extends from the oxygenator 116 and fluidly couples the oxygenator 116 to the brain housing 102. The shunt line 131 is configured to carry fresh perfusate out of the oxygenator 116 directly to the brain housing 102 without passing through a pulse generator 136 of the perfusate system 100. The shunt line 131 can be used in preparation stages to quality check the device prior to the connection of the brain. The shunt line 131 can be used to provide perfusate to the brain housing 102 during the quality check period but is generally not used during the primary application of brain perfusion. A stopcock 135 is positioned along the shunt line 131 downstream of the oxygenator 116. The stopcock 135 can be used to fluidly coupled the shunt line 131 to the brain housing 102 and to sample the perfusate flowing out of the oxygenator 116 prior to providing the perfusate to the brain 110, for example, in order to conduct tests on the perfusate following oxygenation of the perfusate by the oxygenator 116.

A solenoid valve 133 is positioned along the shunt line 131 and is configured to control the flow of perfusate between the oxygenator 116 and the brain housing 102 along the shunt line 131. For example, during the initial set up of the perfusate system 100 for a perfusate procedure, the stopcock 135 is controlled (e.g., using a servo-motor) to fluidly couple the shunt line 131 to the brain housing 102, the solenoid valve 133 along the shunt line 131 is opened and the flow pump 114 is operated to gradually increase the flow of perfusate through the oxygenator 116 to 400 mL/minute, and perfusate flows through the oxygenator 116 along the shunt line 131 and into the brain housing 102. As perfusate flows through the oxygenator 116 and the shunt line 131, any air in the fibers of the oxygenator 116 is forced out of the oxygenator 116 along the shunt line 131 to the brain housing 102, which allow for gas exchange into the perfusate in the oxygenator 116. Once all of the air has been flushed out of the oxygenator 116, the solenoid valve 133 is closed to prevent flow of perfusate from the oxygenator 116 to the brain housing 102 along the shunt line 131.

The arterial circuit 106 includes a flow sensor 130 positioned along the arterial fluid line 112 downstream of the oxygenator 116. When the solenoid valve 133 along the shunt line 131 is closed and the flow pump 114 is operated, fresh perfusate exiting the oxygenator 116 flows along the arterial fluid line 112 through the flow sensor 130, and the flow pump 114 is controlled based on signals generated by the flow sensor 130. In some implementations, the pump speed of the flow pump 114 is adjusted based on one or more signals received from the flow sensor 130 indicating the flow rate of the perfusate exiting the oxygenator 116 in order to control the flow rate of the perfusate exiting the oxygenator 116 to be within a predetermined range. In some implementations, the flow pump 114 is controlled to maintain the flow rate of perfusate exiting the oxygenator 116 to be 400 mL/minute. As previously discussed, the flow rate of perfusate into the oxygenator 116 and the flow rate of gas into the oxygenator 116 can each be controlled to maintain a predetermined ventilation/perfusion coefficient. Thus, in some implementations, the flow pump 114 and the gas mixer 120 are each controlled to adjust the flow rates of perfusate and gas, respectively, into the oxygenator 116 in order to maintain the predetermined ventilation/perfusion coefficient.

Still referring to FIG. 1, the arterial circuit 106 includes a stopcock 132 positioned along the arterial fluid line 112 downstream of the oxygenator 116. The stopcock 132 can be used to sample the perfusate flowing out of the oxygenator 116, for example, in order to conduct tests on the perfusate following oxygenation of the perfusate by the oxygenator 116.

The arterial circuit 106 also includes a one-way valve 134 positioned downstream of the oxygenator 116 and the flow sensor 130. The one-way valve 134 is configured to prevent perfusate in upstream portions of the arterial fluid line 112 from flowing back into the oxygenator 116.

The arterial circuit 106 also includes a pulse generation system 1302 configured to convert laminar flow of perfusate along the arterial fluid line 112 to pulsatile flow along the organ line 144. The pulse generation system 1302 includes a pulse generator device 136 (also referred to herein as "pulse generator 136") and an air supply system 138 fluidly coupled to the pulse generator 136. After flowing out of the oxygenator 116, the perfusate flows along the arterial fluid line 112 to the pulse generator 136. The pulse generator 136 is configured to convert the steady state flow of the fresh perfusate along the arterial fluid line 112 to pulsatile flow. As a result, fresh perfusate is provided to the brain 110 as a pulsatile flow that more closely mimics the anatomical flow of blood to the human brain, which results in improved perfusion of the brain 110. As will be described in detail herein, the pulsatile flow of perfusate generated by the pulse generation system 1302 is dynamically adjusted throughout the perfusion process to optimize the flow rate and fluid pressure of perfusate provided to the brain 110 responsive to the level of resistance of the brain 110, which improves longevity of the cellular and metabolic activity and tissue of the brain 110 being perfused by the system 100.

FIGS. 2A-2D depict the example pulse generator device 136. The pulse generator 136 includes a body 240 that defines a perfusate inlet 204, a sensor block outlet 206, and an organ line outlet 208. Referring to FIGS. 1 and 2A-2D, the perfusate inlet 204 is fluidly coupled to a fluid chamber 236 of the pulse generator 136. The fluid chamber 236 is configured to receive perfusate flowing into the pulse generator 136 from the arterial fluid line 112 through the perfusate inlet 204. The fluid chamber 236 includes a plurality of openings 210 through an upper surface of the fluid chamber 236, and perfusate received by the fluid chamber 236 from the perfusate inlet 204 is configured to flow through the openings 210 into the interior 212 of a central housing 202 of the pulse generator 136. Fluid contained within the interior 212 of the central housing 202 flows through the sensor block outlet 206 and/or the organ line outlet 208, as will be described herein. In some implementations, the diaphragm 214 is a back pressure regulator membrane manufactured by EQUILIBAR®.

Figure 2A:
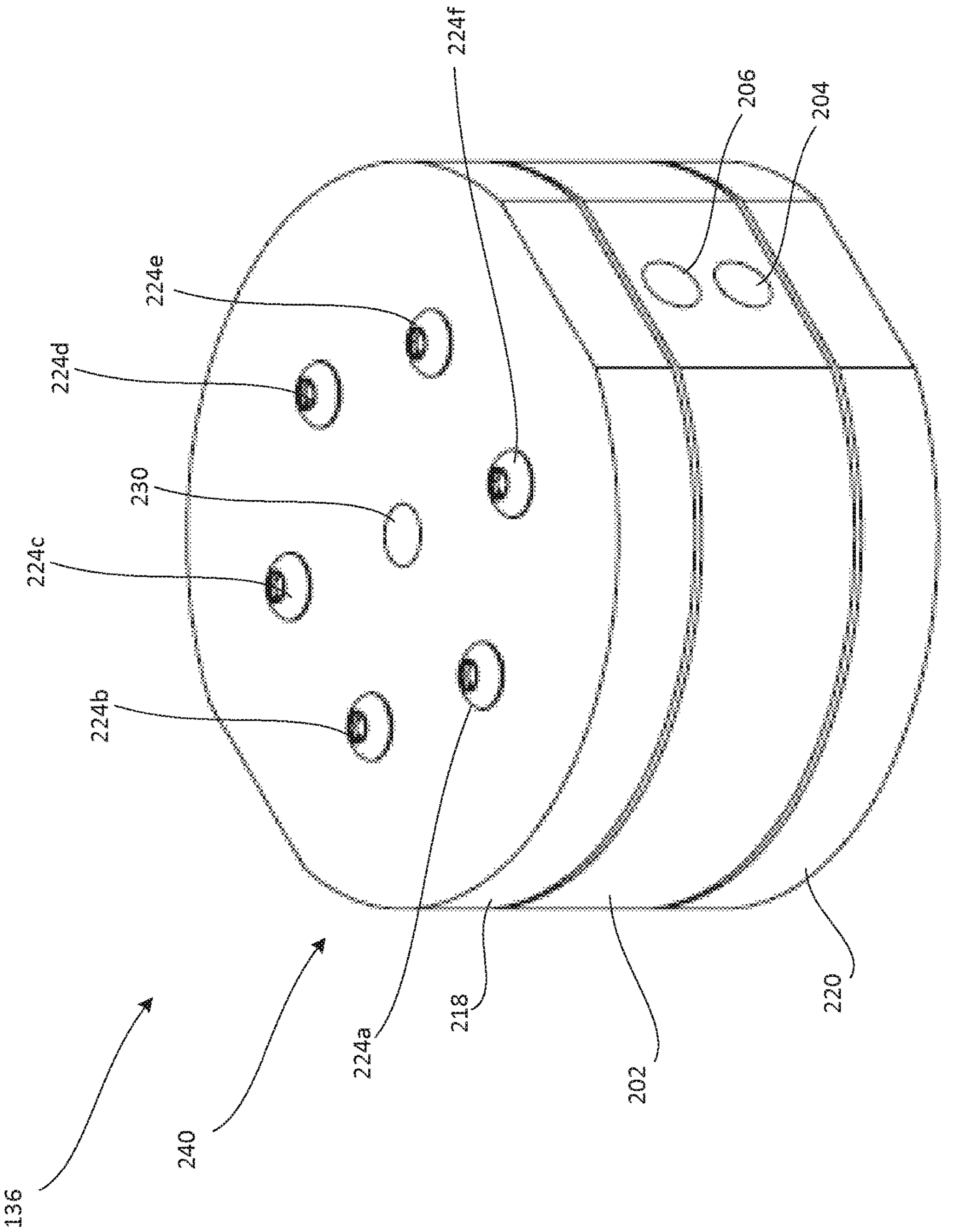
FIG. 2A is a perspective view of an example pulse generator of the system of FIG. 1.
Figure 2B:
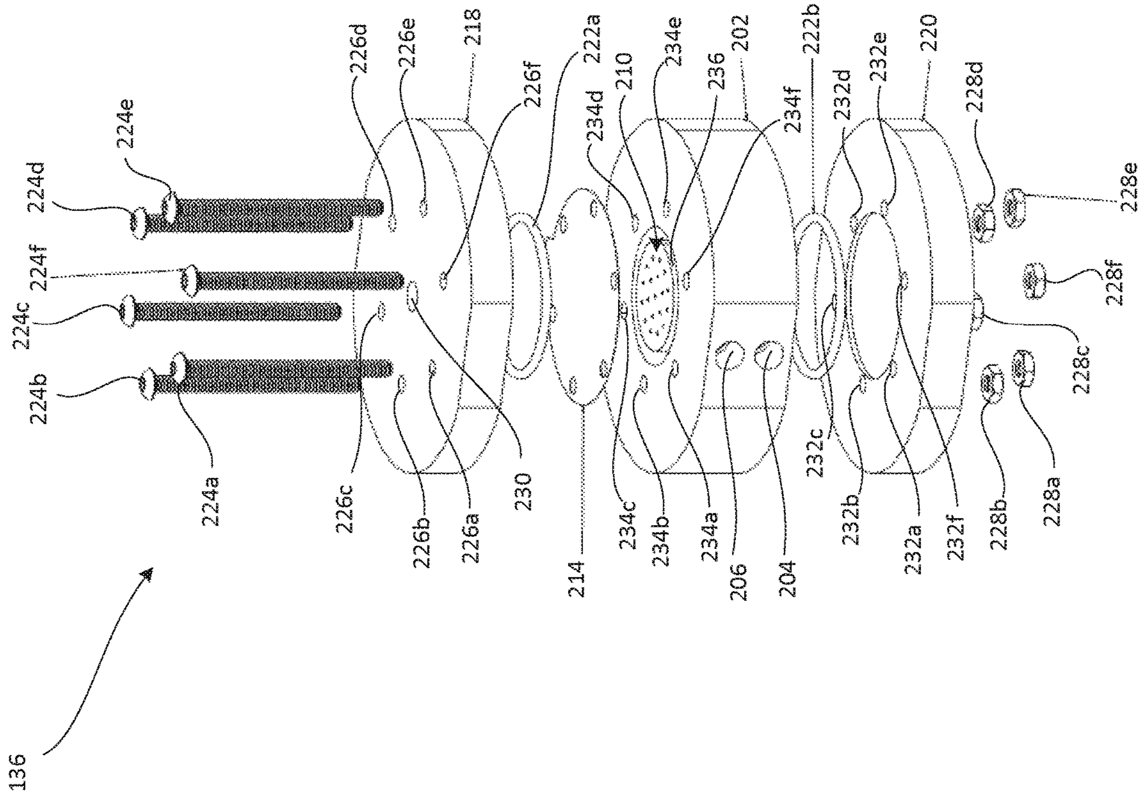
FIG. 2B is an exploded view of the example pulse generator of FIG. 2A.
Figure 2C:
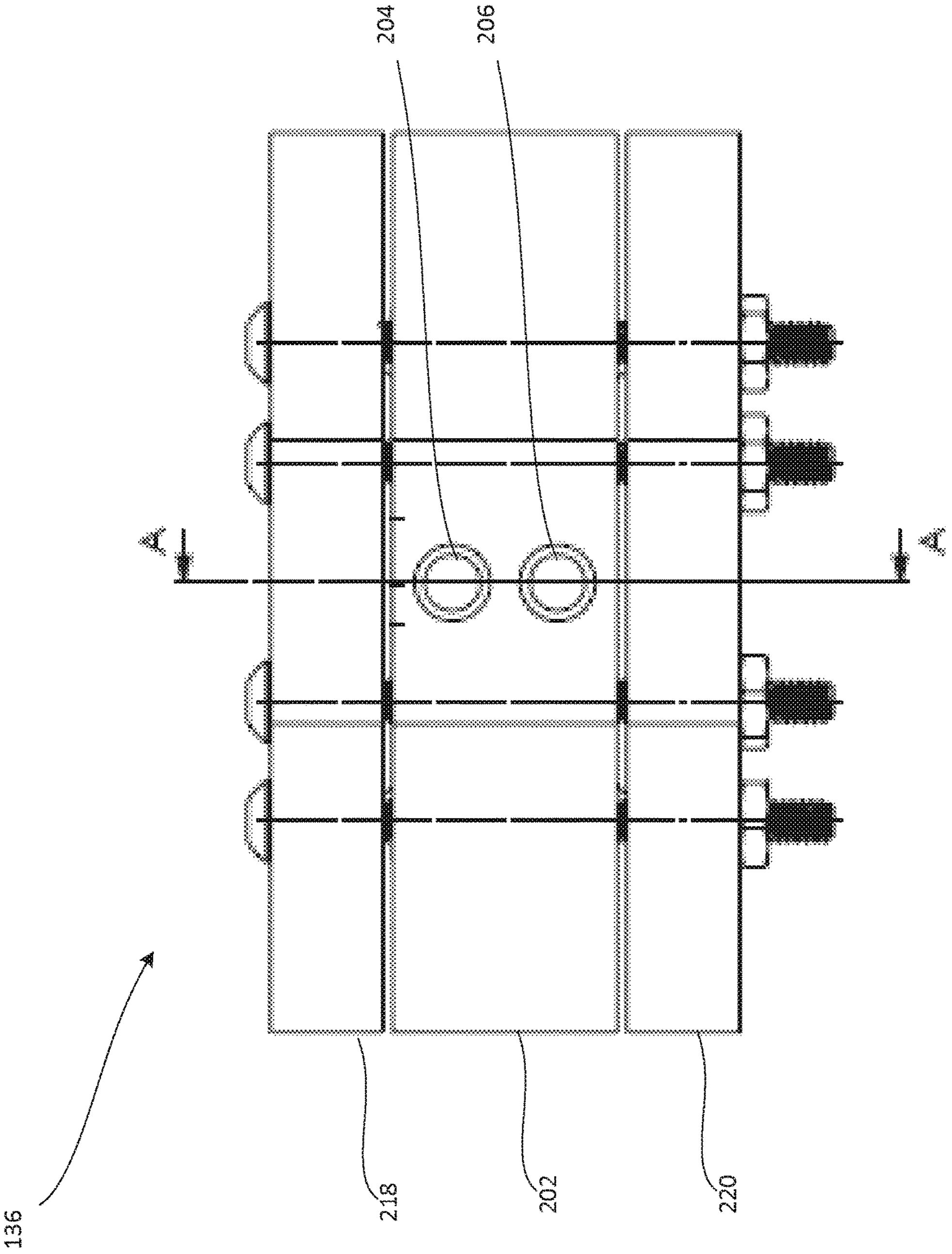
FIG. 2C is a side view of the example pulse generator of FIG. 2A.

Referring to FIG. 2B, the pulse generator 136 further includes a lid 218 and a base 220. A flexible diaphragm 214 is positioned over the fluid chamber 236 between the lid 218 and the central housing 202 of the pulse generator 136. The lid 218 is coupled to an upper surface of the central housing 202 and the base 220 is coupled to a lower surface of the central housing 202. O-rings 222*a*, 222*b* are positioned between the lid 218 and the central housing 202 and between the base 220 and the central housing 202, respectively, in order to prevent perfusate contained within the interior 212 of the central housing 202 from leaking outside of the central housing 202. The lid 218 and the base 220 are coupled to the central housing 202 by a plurality of bolts 224*a*, 224*b*, 224*c*, 224*d*, 224*e*, 224*f* (collectively referred to herein as bolts 224) inserted through a series of respective openings 226*a*, 226*b*, 226*c*, 226*d*, 226*e*, 226*f* through the lid 218, respective openings 234*a*, 234*b*, 234*c*, 234*d*, 234*e*, 234*f* through the central housing 202, and respective openings 232*a*, 232*b*, 232*c*, 232*d*, 232*e*, 232*f* through the base 220. A respective plurality of nuts 228*a*, 228*b*, 228*c*, 228*d*, 228*e*, 228*f* are to the bolts 224.

The lid 28 of the pulse generator 136 defines an air inlet 230 fluidly coupled to and configured to receive pressurized air from the air supply system 138. The air supply system 138 is configured to provided pressurized air to the pulse generator 136 in order to control the pulsatile flow of perfusate received by pulse generator 136. For example, the diaphragm 214 flexes downwards towards the fluid chamber 236 in response to pressurized air being provided by the air supply system 138 through the air inlet 230 of the pulse generator 136. The flexure of the diaphragm 214 causes the openings 210 in the fluid chamber 236 to be covered by the diaphragm 214 and increases the pressure within the interior 212 of the central housing 202, which results in increased flow through the organ line outlet 208 of the pulse generator 136 to the organ line 144 that fluidly couples the pulse generator to the brain 110.

Referring to FIG. 1, the air supply system 138 includes an air source 160, a first electronic pressure regulator 162, a first pressure sensor 164 positioned downstream of the first electronic pressure regulator 162, a second electronic pressure regulator 166 positioned downstream of the first electronic pressure regulator 162, and a second pressure sensor 168 positioned downstream of the second electronic pressure regulator 166. The air source 160, the first electronic pressure regulator 162, the second electronic pressure regulator 166, and the pulse generator 136 are each fluidly coupled along an air supply line 161.

The first electronic pressure regulator 162 is controlled based on pressure signals received from the first pressure sensor 164 in order to provide a pressurized stream of air in a particular pressure range in a particular pressure range to the second electronic pressure regulator 166. In some implementations, the first electronic pressure regulator 162 is configured to regulate the air supply 160 in order to provide a stream of pressurized air to the second electronic pressure regulator 166 that is in a range of 1 to 5 psi.

The second electronic pressure regulator 166 has tighter tolerances compared to the first electronic pressure regulator 162 and is configured to provide a pressurized air stream within a particular pressure range to the air inlet 230 of the pulse generator 136. In some implementations, the second pressure sensor 166 is configured to generate an air stream with a pressure of 5 psi. The pressure of the air stream generated by the second electronic pressure regulator 166 is controlled based on pressure signals received from the second pressure sensor 168 of the air supply system 138. In addition, as will be described in further detail herein, the second electronic pressure regulator 166 is controlled based on signals received from a pressure sensor 141 and a flow sensor 142 positioned along the organ line 144 that fluidly couples the pulse generator 136 to the brain 110 inside the brain housing 102. The use of two electronic pressure regulators 162, 166 to regulate the pressure of the air stream provided to the pulse generator 136 results in a smoother and more controlled supply of pressurized air to the pulse generator 136 compared to using a single electronic pressure regulator. In some implementations, the electronic pressure regulators 162, 166 are QPV electronic pressure regulators manufactured by EQUILIBAR®.

The air supply system 138 also includes an air calibration line 163 that fluidly couples the air supply line 161 to the organ line 144 downstream of the pressure sensors 140, 141 positioned along the organ line 144. As will be described in further detail, the pressure sensors 140, 141 along the organ line 144 are calibrated by providing pressurized air to the organ line 144 along the air calibration line 163. A filter 165 is positioned along the air calibration line 163 in order to filter out and prevent any particulates in the pressurized air stream flowing along the air calibration line 163 from entering the organ line 144. In some implementations, the filter 165 is a 0.22 μm filter.

Figure 2D:
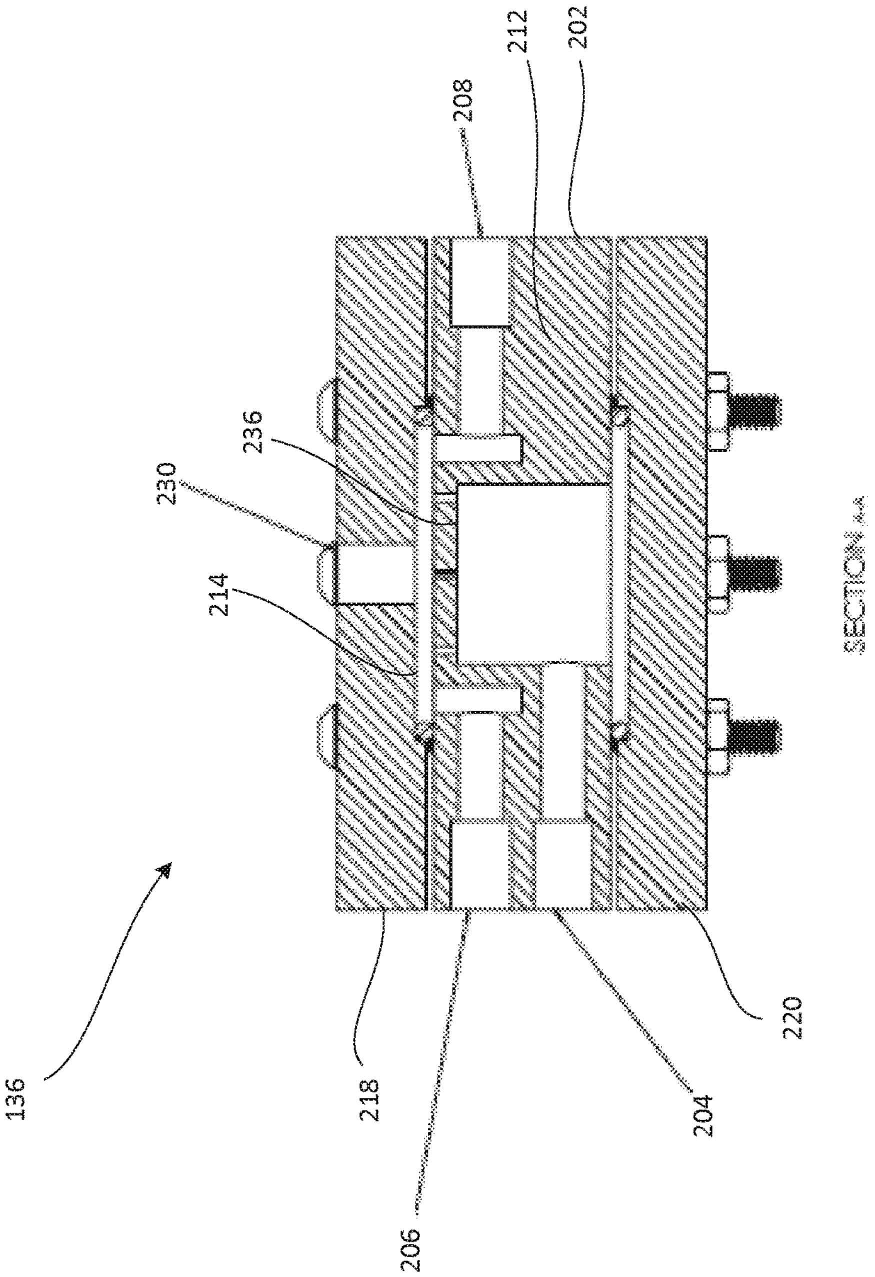
FIG. 2D is a cross-sectional view of the pulse generator of FIG. 2A along axis A-A depicted in FIG. 2C.
Figure 14:
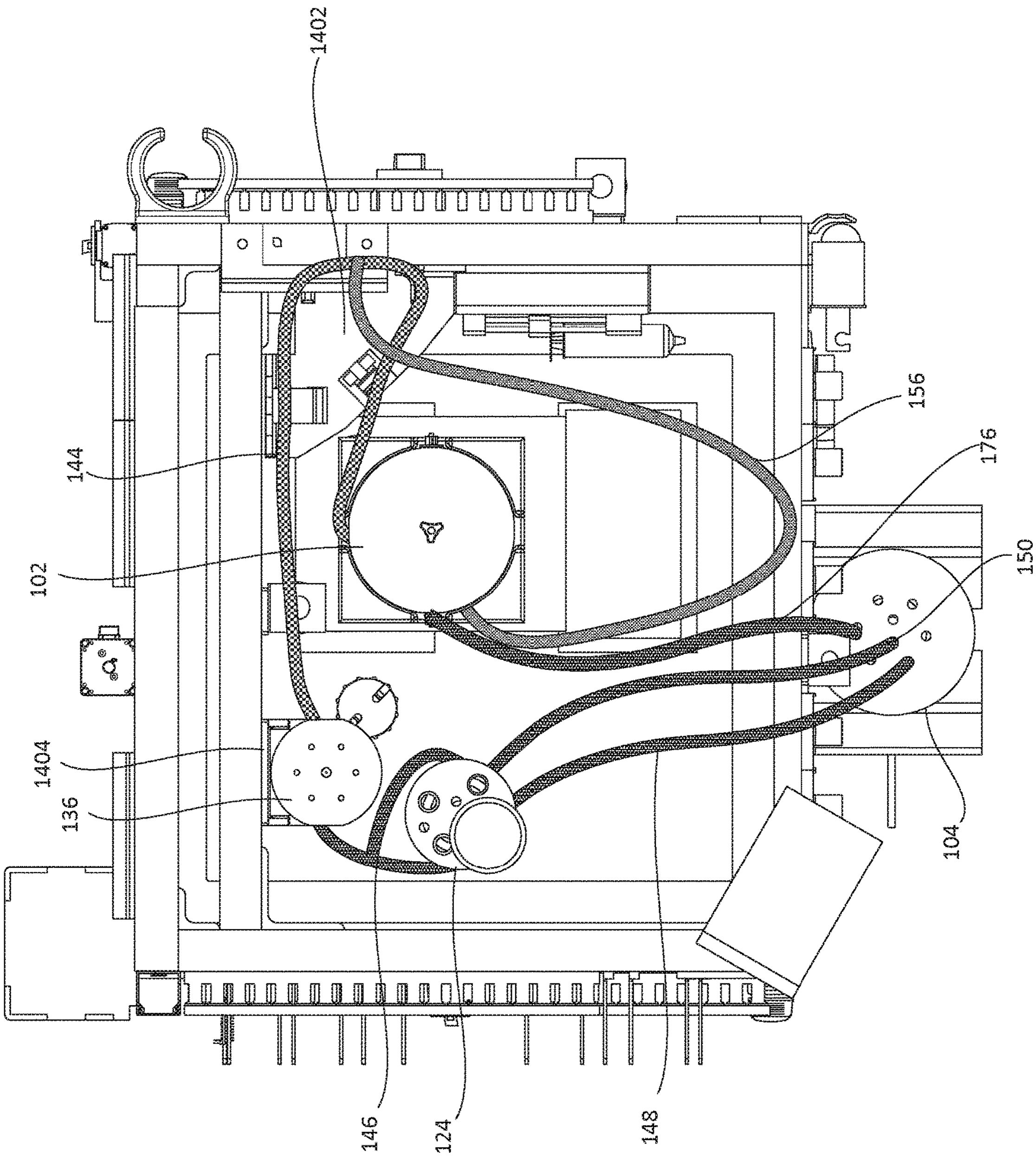
FIG. 14 is a top down view of a portion of the example system of FIG. 1.

In order to restore and maintain the cellular and metabolic activity of the brain 110, the pulse generator 136 and the air supply system 138 are controlled to provide a pulsatile flow of fresh perfusate to the brain 110 within predetermined boundaries of pressure and flow rate that are selected to effectively perfuse the brain while minimizing damage to the vasculature and other tissues of the brain 110. Referring to FIGS. 1 and 2D, a sensor block inlet line 146 is coupled to the sensor block outlet 206 of the pulse generator 136 to fluidly couple the pulse generator 136 to the sensor block 124. The organ line 144 is coupled to the organ line outlet 208 of the pulse generator 136 to fluidly couple the pulse generator 136 to the brain 110. The sensor block inlet line 146 has a larger diameter than the organ line 144. In addition, as can be seen in FIGS. 13-15, the organ line 144 and the pulse generator 136 are each positioned on a respective platform 1402, 1404 that maintains the brain housing 102, the organ line 144, and the pulse generator 136 at substantially equal heights above the height of the sensor block inlet line 146.

As depicted in FIG. 15, in some implementations, the sensor block inlet line 146 is a y-splitter line with a single line flowing out of the pulse generator 136 that splits into two fluid lines flowing into the sensor block 124. The sensor block inlet line 146 extends downwards relative to the organ line 144. As a result of the relative positioning of the pulse generator 136, the brain housing 102, the organ line 144, and the sensor block 124, there is no passive flow of fluid from the pulse generator 136 to the brain 110 inside the brain housing 102, and all of the perfusate contained within the interior 212 of the central housing 202 of the pulse generator 136 passively flows through the sensor block inlet line 146 when the diaphragm 214 of the pulse generator 136 is in an unflexed ("neutral") position. Therefore, in order to provide fresh perfusate from the pulse generator 136 to the brain 110 via the organ line 144, the diaphragm 214 of the pulse generator 136 must be flexed downwards towards the fluid chamber 236 to cover the openings 210 in the fluid chamber 236 and increase the pressure within the interior 212 of the central housing 202. As result of the increased pressure caused by flexing the diaphragm 214, at least a portion of the fresh perfusate contained within the interior 212 of the pulse generator is forced through the organ line outlet 208 and along the organ line 144 to the brain 110.

In addition, the sensor block inlet line 146 has a larger diameter than the organ line 144. In some implementations, the sensor block inlet line 146 includes a Y-connector and two fluid lines extending from the Y-connector to fluidly couple the pulse generator 136 to the sensor block 124, further decreasing the resistance to flow between the pulse generator 136 and the sensor block 124. As a result of the decreased resistance to flow between the pulse generator 136 and the sensor block 124 compared to the resistance to flow between the pulse generator 136 and brain 110 inside the brain housing 102 due to the structural differences in the sensor block inlet line 146 and the organ line 144, at least a portion of the perfusate flowing through the pulse generator 136 is provided to the sensor block 124 from the pulse generator 136, even when the diaphragm 214 of the pulse generator 136 is in a flexed position.

In order to maintain an optimal pulsatile flow of perfusate along the organ line that is responsive to the internal resistance of the brain 110, the air supply system 138 coupled to the pulse generator 136 is controlled based on signals generated by a pressure sensor 141 and a flow sensor 142 positioned along the organ line 144. In some implementation, the pulse generation system 1302 is controlled to maintain the pressure along the organ line 144, as measured by the pressure sensor 141, between 5 mmHg and 100 mmHg. In some implementation, the pulse generation system 1302 is controlled to maintain the flow rate along the organ line 144, as measured by the flow sensor 142, between 0 mL/min and 750 mL/minute. The flow rate measured by the flow sensor 142 corresponds to the average flow rate of the pulse of fluid provided by the pulse generator 136.

The second electronic pressure regulator 166 of the air supply system 138 is controlled to provide pressurized air to the air inlet 230 of the pulse generator 136 at particular intervals and durations based on the signals generated the second pressure sensor 141 and the flow sensor 142 along the organ line 144 in order to achieve a particular pressure and/or flow rate of perfusate along the organ line 144. As the second electronic pressure regulator 166 provides pressurized air to the air inlet 230 of the pulse generator 136, the diaphragm 214 of the pulse generator 136 flexes downwards towards the fluid chamber 236 in response to the increased positive pressure in the air inlet 230 and covers the openings 210 in the fluid chamber 236. As result of the increased pressure within the interior 212 of the pulse generator 136 caused by the flexing of the diaphragm 214, at least a portion of the fresh perfusate contained within the interior 212 of the pulse generator is forced through the organ line outlet 208 and along the organ line 144 to the brain 110. By adjusting the frequency and/or duration of the pressurized air streams provided by the second electronic pressure regulator 166 to the pulse generator 136 in response to pressure and flow rate signals received from sensors 141, 142, the amplitude and base of the pulse of perfusate provided by the pulse generator 136 to the organ line 144 can be optimized based on the internal resistance of the brain detected by the sensor 141, 142.

In addition, as depicted in FIG. 1, the perfusion system 100 includes a resistance valve 152 positioned along the organ line 144 and that can be operated to further provide a particular flow resistance along the organ line 144. In particular, the resistance valve 152 is controlled to prevent passive flow of perfusate along the organ line 144 due to the driven flow provided by the flow pump 114.

The resistance valve 152 is positioned along the organ line 144 downstream of the first pressure sensor 140 and the flow sensor 142 and is positioned upstream of the second pressure sensor 141. During calibration of the system 100, the flow pump 114 is operated to flow perfusate along the organ line 144 toward the brain 110 at a predetermined rate without operating the pulse generation system 1302. As the flow pump flows perfusate along the organ line 144 during calibration, the pressure along the organ line 144 upstream of the resistance valve 152 is measured by the first pressure sensor 140 and the pressure along the organ line 144 downstream of the resistance valve 152 is measured by the second pressure sensor 141. Based on the pressure measured by the pressure sensors 140, 141, the resistance valve 152 can be adjusted (e.g., partially or fully opened or partially or fully closed) in order to predetermined internal resistance along the organ line 144. In some implementations, the resistance valve 152 is controlled, based on the data generated by the pressure sensors 140, 141, to provide an internal resistance of 1 mmHg along the organ line 144.

During the post-mortem interval prior to beginning the perfusion process, the brain 110 undergoes processes resulting in an increased internal resistance to flow within the vasculature of the brain 110. For example, during the post-mortem interval prior to beginning the perfusion process, water leaks into the brain tissue and collapses the capillaries of the brain 110, resulting in the formation of internal Starling resistors in the brain and an increased internal resistance to flow within the vasculature of the brain 110. Therefore, in order to condition the vasculature of the brain 110 to sufficiently uptake the fresh perfusate and perfuse the brain, the pulse generator 136 is controlled at the beginning of the perfusion process to gradually increase the pressure and flow rate of the fresh perfusate provided along the organ line 144 in a stepwise manner based on signals received from the second pressure sensor 141 and the flow sensor 142 positioned along the organ line 144. For example, at the beginning of the perfusion process, the electronic pressure regulators 162, 166 of the air supply system 138 are controlled to provide pressurized air to the pulse generator 136 and cause the pulse generator 136 to increase the pressure of the pulsatile flow of the fresh perfusate along the organ line 144 until an initial pressure threshold is detected by the second pressure sensor 141. In some implementation, the initial pressure threshold along the organ line is 16 mmHg. Once the initial pressure threshold along the organ line 144 has been maintained for a predetermined period, the electronic pressure regulator 166 of the air supply system 138 is controlled to cause the pulse generator 136 to increase the pulsatile flow along the organ line 144 until a second pressure threshold is detected along the organ line 144 by the second pressure sensor 141. In some implementations, the air supply system 138 and the pulse generator 136 are controlled based on signals received from the pressure sensor 141 to increase the pressure along the organ line 144 at a rate of 0.0333 mmHg/minute. By controlling the pulse generation system 1302 to gradually increase the pressure of perfusate provided to the brain 110, the internal resistance of the brain 110 is correspondingly gradually reduced, which enables the vasculature of the brain 110 to more effectively receive the perfusate while minimizing injury or other damage to the brain 110.

As the pressure along the organ line 144 is increased, the flow rate of perfusate along the organ line 144 is simultaneously monitored using the flow sensor 142, and the pulse generation system 1302 is controlled to continually increase the pressure along the organ line 144 until a predetermined target flow rate is detected along the organ line 144. In some implementations, the target flow rate is 10 mL/minute. Once the target flow rate is detected by the flow sensor 142, the pulse generation system 1302 is controlled based on signals generated by the flow sensor 142 in order to provide pulsatile flow along the organ line 144 sufficient to maintain the predetermined flow rate along the organ line 144 as detected by the flow sensor 142.

The pulse generation system 1302 is controlled throughout the perfusion period (e.g., 24 hours or longer, 48 hours or longer, etc.) based on the signals generated by the pressure sensor 141 and the flow sensor 142 in order to maintain the predetermined flow rate of perfusate along the organ line 144 throughout the perfusion process while also maintaining the pressure along the organ line 144 within the predetermined pressure boundaries. For example, while perfusate is provided to the brain 110 in pulses generated by the pulse generation system 1302 to maintain a predetermined flow rate, the pressure along the organ line 144 continues to be measured by the pressure sensor 141. If the pressure detected by the second pressure sensor 141 falls outside of predetermined pressure boundaries, the pulse generation system 1302 is controlled to adjust the pulsatile flow along the organ line 144 is adjusted so that the pressure measured by the second pressure sensor 141 is within the pressure boundaries. Because the pulsatile flow provided by the pulse generator 136 to the brain 110 is controlled in real-time based on the pressure and the flow rate detected by the second pressure sensor 141 and the flow sensor 142, respectively, the flow of perfusate to the brain 110 is controlled dynamically in response to the real-time changes in internal resistance experienced by the brain 110 throughout the perfusion process. As used herein, a real-time operation may describe an operation that is performed with minimal delay, taking into account the limitations of the computing system(s) performing the operation. For example, in some implementations, the flow sensor 142 is sampled at a rate of 100 Hz, the pressure sensors 140, 141 are sampled at a rate of 80 Hz, and the pulse generation system 1302 is controlled adjust the flow of perfusate to the brain every one second based on the data received from the flow sensor 142 and the pressure sensor 141. In some implementations, the flow sensor 130 is sampled at a rate of 100 Hz and the flow pump 114 is controlled every 0.5 seconds based on the data generated by the flow sensor 130. In some implementations, the sensor probes 128 in the sensor block 124 are each sampled at a rate of 1 Hz, and the operations of the heat exchanger 118 and the gas mixer 120 are each updated every one second based on the data generated by the sensor probes 128. In some implementations, the resistance valve 152 is controlled at a 10 Hz frequency. The dynamic nature of the perfusate flow provided to the brain 110 by the pulse generation system 1302 ensures that the brain 110 is sufficiently perfused while simultaneously preventing injury to the brain 110.

As previously discussed, at least a portion of the fluid flowing through the pulse generator 136 is provided to the sensor block 124 along the sensor block inlet line 146. The sensor block 124 includes a housing 126 configured to receive and contain fresh perfusate flowing from the pulse generator 136. The housing 126 of the sensor block 124 is positioned on a sensor block scale 137 that is configured to measure the weight of perfusate contained in the housing 126 of the sensor block 124 throughout the perfusion procedure. The flow rate of perfusate into and out of the sensor block 124, the volume of perfusate flowing into and out of the sensor block 124, and the times at which perfusate is added to and drained from the sensor block 124 can be monitored and recorded based on the weight measured by the sensor block scale 137. In addition, the sensor block scale 137 can be used to validate the time at which samples of perfusate are collected from the sensor block 124 by the automatic sampler system 105.

The sensor block 124 also includes a plurality of sensor probes 128 positioned within the housing 126 of the sensor block 124. The sensor probes 128 are configured to measure certain characteristics of the fresh perfusate inside the housing 126 including, but not limited to, pH, dissolved oxygen concentration, dissolved nitrogen concentration, dissolved carbon dioxide concentration, viscosity, redox potential, and temperature. As previously described, the oxygenator 116, the heat exchanger 118, and the gas mixer 120 are controlled based on the characteristics measured by the sensor probes 128 in order to optimize the temperature, $O_2$ level, and gas composition of the perfusate. In some implementations, an alpha stat approach is used to control the concentration of gasses with the fresh perfusate and the pH of the fresh perfusate.

The housing 126 of the sensor block 124 is fluidly coupled to the perfusate reservoir 104 along a sensor block outlet line 148 and an arterial sample line 150, and fresh perfusate flowing through the sensor block 124 is provided to the perfusate reservoir 104 along the sensor block outlet line 148 and/or the arterial sample line 150. A stopcock 153 is positioned along the arterial sample line 150, and can be used to sample the perfusate flowing out of the sensor block 124, for example, to conduct tests on the perfusate exiting the sensor block 124. Solenoid valves 149, 151 are positioned along the sensor block outlet line 148 and the arterial sample line 150, respectively, and are configured to control flow of fluid from the sensor block 124 to the perfusate reservoir 104. For example, the sensor block 124 includes a level sensor 125 that is configured to detect the level of fluid (e.g., fresh perfusate) inside the housing 126 of the sensor block 124, and the solenoid valve 149 along the sensor block outlet line 148 is controlled to open or close based on signals generated by the level sensor 125. In some implementations, the level sensor 125 is an optical level sensor, such as an infrared level sensor. For example, the solenoid valve 149 is controlled to remain in a closed state and prevent flow of fresh perfusate from the sensor block 124 into the perfusate reservoir 104 until the level sensor 125 generates a signal indicating that the fluid level inside the housing 126 of the sensor block 124 has exceeded a threshold fluid level. In response to the level sensor 125 generating a signal indicating that the fluid level inside the housing 126 of the sensor block 124 has exceeded a threshold fluid level, the solenoid valve 149 is controlled to open to allow perfusate to flow from the sensor block 124 along the sensor block outlet line 148 to the perfusate reservoir 104. Once the level sensor 125 detects that the fluid level inside the housing 126 of the sensor block 124 has fallen below the threshold level, the solenoid valve 149 is controlled to close, which prevents perfusate from flowing from the sensor block 124 to the perfusate reservoir 104 along the sensor block outlet line 148.

Figure 3:
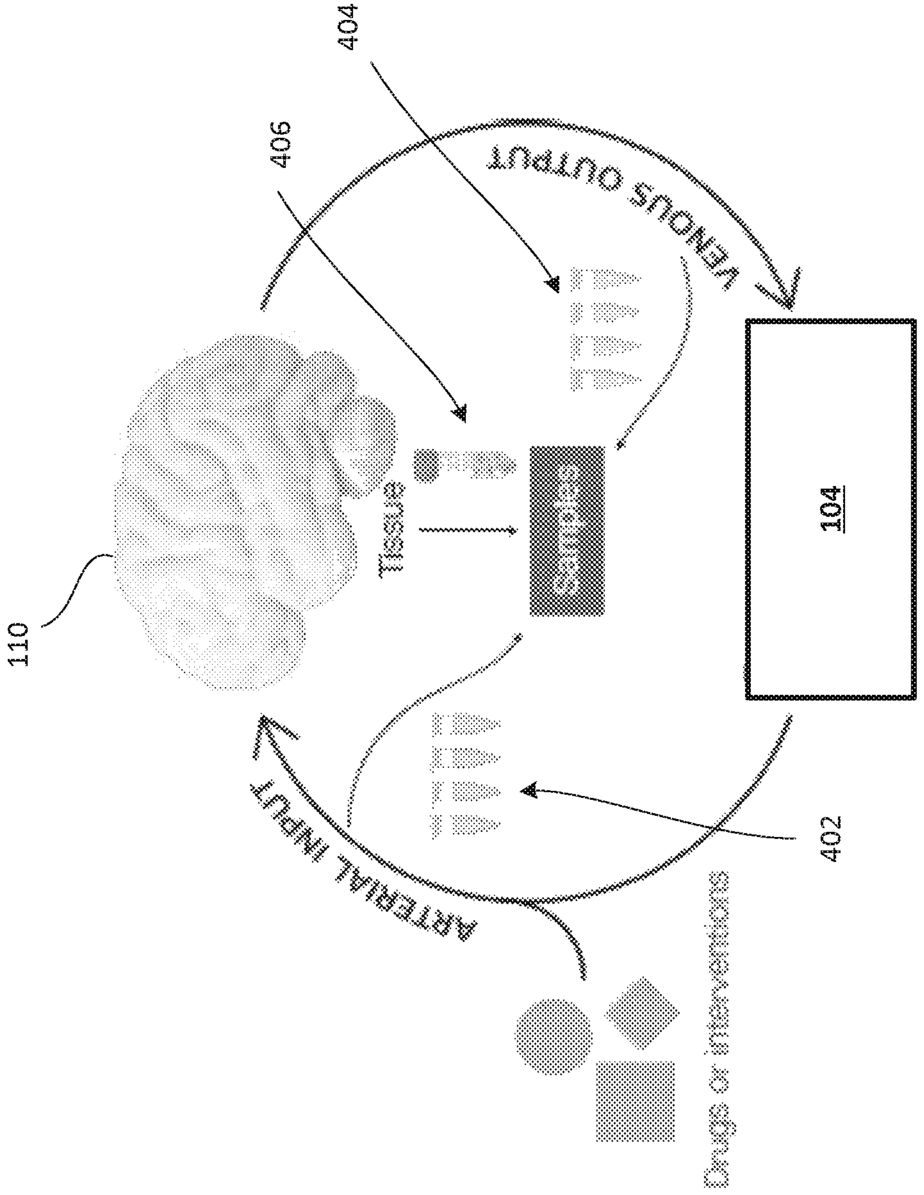
FIG. 3 is a schematic illustration of a process of sampling perfusate and brain tissue during perfusion of a brain using the system of FIG. 1.

Referring to FIGS. 1 and 3, in addition to fluidly coupling the sensor block 124 to the perfusate reservoir 104, the arterial sample line 150 fluidly couples the sensor block 124 to an automatic sampler system 105. The automatic sampler system 105 includes a pump 184, a solenoid manifold 185, a sample collection line 186, and a purge line 187. The automatic sampler system 105 can be operated to automatically collect a sample of perfusate from the sensor block 124, for example, for testing one or more characteristics of the fresh perfusate contained inside the sensor block 124. A solenoid valve 171 is positioned along the arterial sample line 150 between the sensor block 124 and the automatic sampler system 105. In order to automatically collect a sample of perfusate from the arterial sample line 150, the solenoid valve 171 along the arterial sample line 150 between the sensor block 124 and the automatic sampler system 105 is opened, and the pump 184 of the automatic sampler system 105 is operated to draw perfusate out of the sensor block 124 along the arterial sample line 150, and the solenoid manifold 185 is controlled to direct the perfusate through the sample collection line 186 and into a sample collection vessel. The automatic sampler system 105 can be controlled to collect samples of fresh perfusate 302 from the sensor block 124 at predetermined intervals during the perfusion process. For example, in some implementations, the automatic sampler system 105 is configured to collect samples of fresh perfusate 302 from the sensor block 124 at the start of a perfusion process ("0 hour"), 6 hours after the start of a perfusion process, 12 hours after the start of a perfusion process, and 24 hours after the start of a perfusion process. Samples can alternatively be collected at any other desired frequency.

The purge line 187 of the automatic sampler system 105 is used to purge the contents of the arterial sample line 150 and the contents of a corresponding venous sample line 183 prior to collecting a fluid sample from the arterial sample line 150 or the venous sample line 183, respectively. For example, prior to sampling fluid from the arterial sample line 150, the solenoid valve 171 along the arterial sample line 150 is opened, the pump 184 and the solenoid manifold 185 of the automated sampler system 105 are controlled to draw the fluid contained inside the arterial sample line 150 through the purge line 187 to a drain or waste container. After a predetermined amount of time has elapsed, the solenoid manifold 185 is operated to direct the fluid flowing along the arterial sample line 150 through the sample collection line 186 and into a sample collection vessel. As a result of this purging process, the perfusate samples 402 collected by the automatic sampler system 105 from the arterial sample line 150 corresponds to fresh perfusate that has exited the sensor block 124 at the time the sample collection is performed, rather than perfusate that was present in the arterial sample line 150 prior to the time of sample collection.

Still referring to FIG. 1, a first stopcock 154 is positioned along the organ line 144 upstream of the resistance valve 152 and a second stopcock 155 is positioned along the organ line 144 downstream of the resistance valve 152. An operator of the system 100 can use the stopcocks 154, 155 to sample fluid from the organ line 144 upstream or downstream, respectively of the resistance valve 152, for example, to test one of more properties of the perfusate being provided to the brain 110. In addition, the stopcocks 154, 155 can be operated in order to control the flow of air along the organ line during initial set up and calibration of the system 100. For example, during initial calibration of the pressure sensor 141, pressurized air is provided to the organ line along the air calibration line 163 through stopcock 155, and the stopcocks 154, 155 are both closed to generate a stable air pressure along the organ line 144 between the stopcocks 154, 155, and the pressure sensor 141 can be calibrated based on the measured pressure.

A solenoid valve 159 is positioned along the organ line 144 downstream of the second pressure sensor 141 and the second stopcock 155. The solenoid 159 is configured to control fluid flow from the organ line 144 into a brain interface 170 inside the brain housing 102. For example, during perfusion of the brain 110, the solenoid 159 is opened to allow fluid within the organ line 144 flow to the brain interface 170 inside the brain housing 102. As will be described in further detail herein, the solenoid 159 is closed during calibration of the pressure sensors 140, 141 and the flow sensors 142 to prevent fluid along the organ line 144 from flowing into the brain interface 170.

Figure 10A:
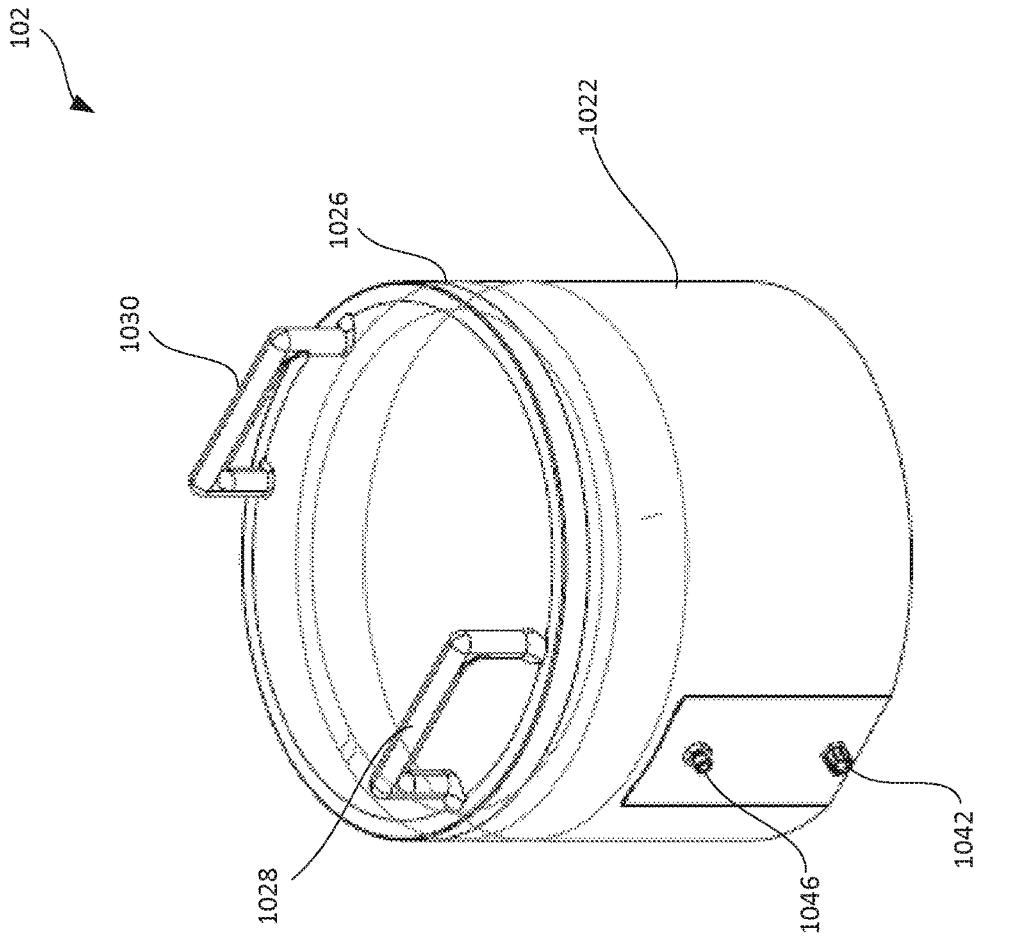
FIG. 10A is a perspective view of an example brain housing of the system of FIG. 1.
Figure 10C:
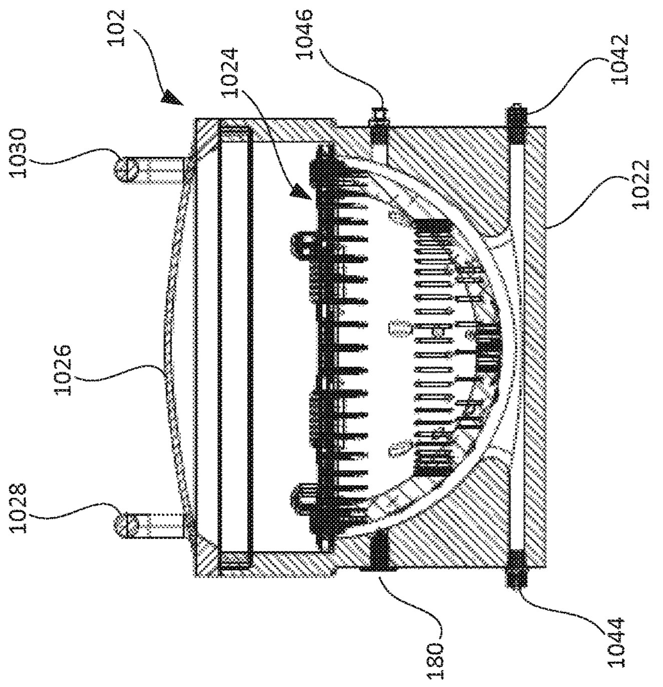
FIG. 10C is a cross-sectional view of the example brain housing of FIG. 10A.
Figure 10B:
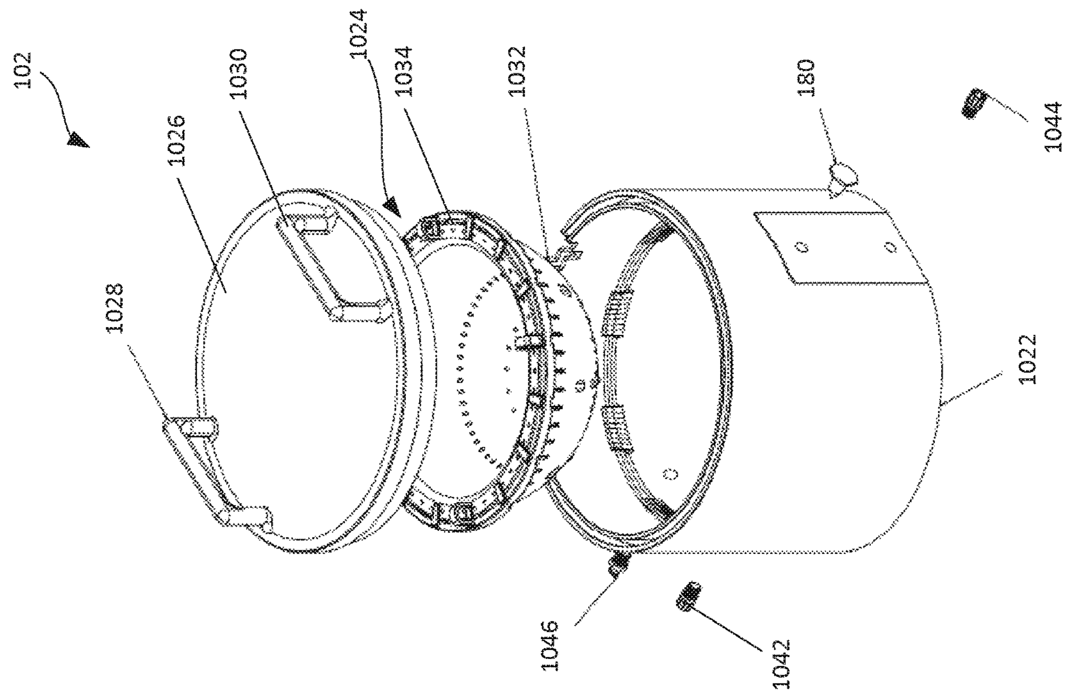
FIG. 10B is an exploded view of the example brain housing of FIG. 10A.

A brain housing shunt line 156 extends from the organ line 144 to the brain housing 102 and fluidly couples the organ line 144 to the interior of the brain housing 102. Referring to FIGS. 10A-10C, the brain housing 102 includes a fluid coupling 1046 that fluidly connects the shunt line 156 to the interior of the brain chamber 102. In some implementations, the coupling 1046 is a quick-turn tube coupling. The brain housing shunt line 156 is positioned downstream of the resistance valve 152 and upstream of the second pressure sensor 141. A solenoid valve 158 is positioned along the brain housing shunt line 156 and can be operated to fluidly couple the organ line 144 to the brain housing 102 along the brain housing shunt line 156. In some implementations, the solenoid valve 158 along the brain shunt line 156 is opened to allow perfusate to flow from the organ line 144 to the brain housing 102 along the brain housing shunt line 156 during initial calibration of the pressure sensors 140, 141 and flow sensor 142 along the organ line 144.

In some implementations, the organ line 144 is fluidly coupled to the brain 110 positioned in the housing through a brain interface 170 inside the brain housing 102. The brain interface 170 is a 3D-printed mechanical interface that includes a base plate configured to stabilize and support the brain 110 inside the housing, two fluid inlets, and two corresponding fluid outlets. A y-connector is coupled to an end of the organ line 144, and each of the fluid inlets of the brain interface 170 are fluidly coupled to the organ line 144 using the y-connector and each inlet of the brain interface 170 receives fresh perfusate flowing out of the organ line 144 into the brain interface 170. The brain interface 170 defines flow paths fluidly coupling each of the fluid inlets of the brain interface 170 to a respective outlet of the brain interface 170. Prior to placing the brain 110 in the brain housing 102 and beginning perfusion of the brain 110, each of the carotid arteries of the brain 110 is sutured to a respective fluid outlet of the brain interface 170. Once the carotid arteries of the brain 110 are sutured to the fluid outlets of the brain interface 170, the inlets of the brain interface 170 are coupled to the organ line 144 using a y-connector and the brain 110 and brain interface 170 are enclosed in the brain housing 102 throughout the perfusion process. As fresh perfusate flows along the organ line 144, the perfusate enters the fluid inlets of the brain interface 170 and flows through the fluid pathways defined by the brain interface 170, through the fluid outlets of the brain interface 170, and into the carotid arteries of the brain 110.

The pressure and flow rate of the perfusate provided to the brain 110 are controlled to enable the perfusate entering the carotid arteries of the brain 110 to perfuse the entire vasculature of the brain 110, including the penetrating arterioles, pre-capillary arterioles, and capillaries of the brain 110.

The brain 110 is contained inside the brain housing 102 throughout the perfusion process. FIGS. 10A-F depict an example brain housing 102. Referring to FIGS. 10A and 10B, the brain housing 102 includes a basin 1022, a hemispherical brain chamber 1024, and an upper lid 1026.

The lid 1026 is configured to releasably couple to the basin 1022 of the brain housing 102 and can be separated from the basin 1022 to allow a brain 110 to be positioned inside the brain housing 102 on the hemispherical brain chamber 1024. The lid 1026 includes a pair of handles 1028, 1030 to enable removal of the lid 1026 from the basin 1022 When the lid 1026 is coupled to the basin 1022, the basin 1022 and lid 1026 form slots for the tubing of the organ line 144 to enter inside the interior of the brain housing 102 with minimal air gaps between the lid 1026 and the basin 1022.

Referring to FIGS. 10B and 10C, the hemispherical brain chamber 1024 is configured to be positioned within the basin 1022 and is covered by the upper lid 1026 when the upper lid 1026 is attached to the basin 1022. During the perfusion process, the brain 110 is positioned on the hemispherical brain chamber 1024 with the carotid and basilar arteries of the brain 110 facing upwards toward the lid 1026.

Figure 10E:
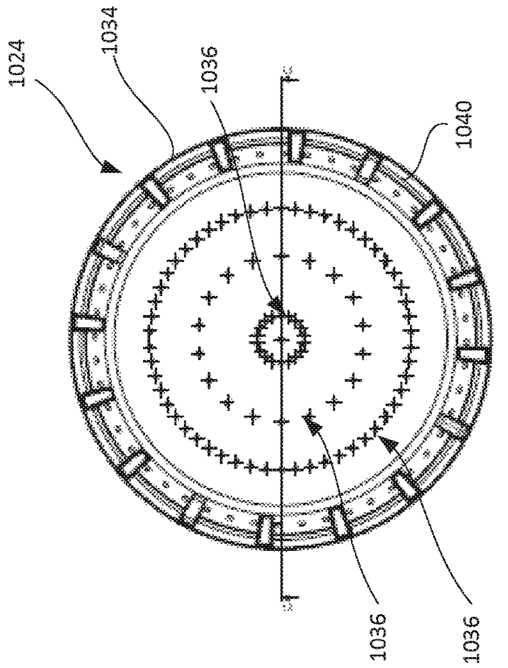
FIG. 10E is a top view of the example hemispherical brain chamber of FIG. 10D.
Figure 10F:
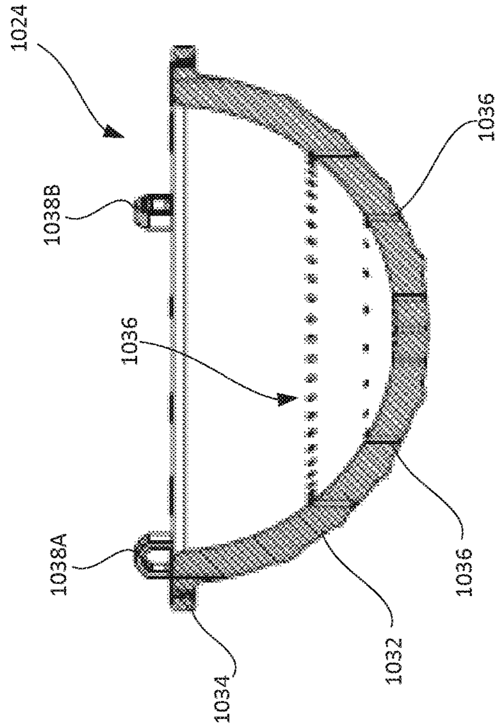
FIG. 10F is a cross-sectional view of the example hemispherical brain chamber of FIG. 10D.
Figure 10D:
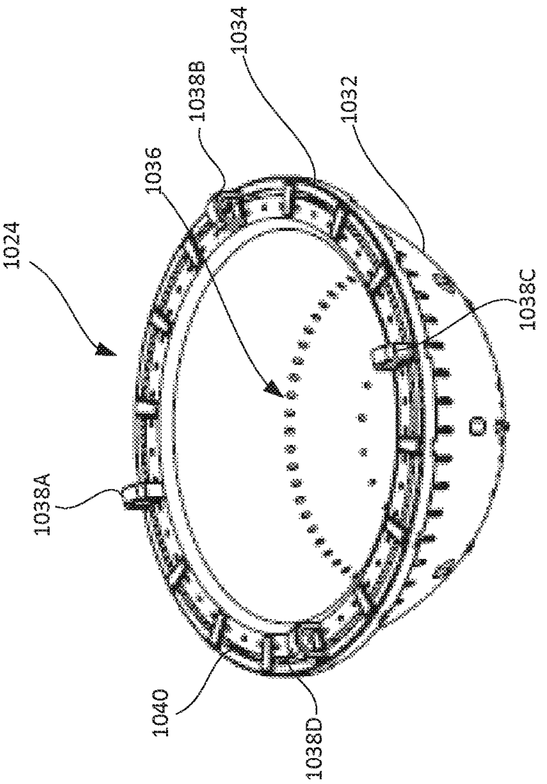
FIG. 10D is a perspective view of an example hemispherical brain chamber of the example brain housing of FIG. 10A.

Referring to FIGS. 10D-10F, the hemispherical brain chamber 1024 includes a chamber body 1032 that is configured to receive and support the brain 110 throughout a perfusion process. The chamber body 1032 is formed of a polymer material that provides a soft surface on which the brain 110 can be positioned and supported within the brain housing 102 throughout the perfusion process. The size, shape, and material of the chamber body 1032 are selected to maintain integrity of the brain 110 throughout the perfusion process. The chamber body 1032 defines a plurality of drain holes 1036 through the chamber body 1032. The drain holes 1036 allow perfusate flowing out of the veins of the brain 110 to flow through the hemispherical brain chamber 1024 into the basin 1022 such that the perfusate flowing out of the brain 110 is collected in the basin 1022.

As can be seen in FIGS. 10C-10F, the hemispherical brain chamber 1024 includes an upper lip 1034 extending from the chamber body 1032. When the hemispherical brain chamber 1024 is positioned within the basin 1022, the upper lip 1034 of the hemispherical brain chamber 1023 rests on an upper edge of the basin 1022 and allows the hemispherical brain chamber 1024 to be suspended within the basin 1022 without the contacting the bottom surface of the basin 1022 or blocking a level sensor 180 of the brain housing 102. The upper lip 1034 also defines a plurality of support slots 1040 configured to receive corresponding support structures of the basin 1022 that help support the weight of the brain 110 positioned on the hemispherical brain chamber 1024.

Referring to FIGS. 10D and 10F, the hemispherical brain chamber 1024 includes loops 1038A-1038D that are coupled to the upper lip 1034 and that can be used to facilitate removal of the hemispherical brain chamber 1024 from the basin 1022. For example, an operator of the system 100 can grasp one or more of the loops 1038A-1038D with her fingers to lift the hemispherical brain chamber 1024 out of the basin 1022.

The brain housing 102 is configured to maintain the brain 110 under normothermic conditions. For example, when the basin 1022 and lid 1026 of the brain housing 102 are securely coupled together, a warm, humid environment is maintained within the brain housing 102. In some implementations, the brain housing 102 includes temperature and humidity controls configured maintain a particular temperature and humidity level to prevent drying or other injury to the brain 110.

After the perfusate flows through the capillaries of the brain 110, the perfusate flows out of the brain 110 via veins, through the drain holes 1036 in the hemispherical brain chamber 1024, and into the basin 1022 of the brain housing 102. The basin 1022 of the brain housing 102 collects and contains the perfusate that flows out of the brain 110 ("used perfusate").

The brain housing 102 is positioned on a brain housing scale 174 that measures the weight of the brain 110 and the contents inside the housing (e.g., the brain 110 and used perfusate) throughout the perfusion process. Based on the weight measurements generated by the brain housing scale 174, the amount of swelling of the brain 110 due to fluid retention can be estimated in real-time throughout the perfusion process. In addition to monitoring swelling, the brain housing scale 174 can be used also to calculate and validate the flow measurements generated by the flow sensor 142 along the organ line 144. For example, the amount of perfusate provided to the brain housing 102 during a particular period of time as determined by the weight measured by the brain housing scale 174 can be compared to the amount of perfusate flow measured by the flow sensor 142 during the particular time period in order to validate the measurements of the flow sensor 142. In addition, the brain housing scale 174 can be used to validate the time at which samples of perfusate is collected from the brain housing 102 by the automatic sampler system 105.

A housing outlet line 176 extends from the brain housing 102 and fluidly couples the brain housing 102 to the perfusate reservoir 104. A solenoid valve 178 is positioned along the housing outlet line 176 to control the flow of used perfusate from the brain housing 102 into the perfusate reservoir 104. For example, when the solenoid valve 178 is open, used perfusate collected in the brain housing 102 flows along the housing outlet line 176 into the perfusate reservoir 104.

Referring to FIGS. 10B and 10C, the brain housing 102 includes a coupling 1042 connected to the side of the basin 1022. The coupling 1042 fluidly connects the interior of the basin 1022 of the brain chamber 102 to the housing outlet line 176. In some implementations, the coupling 1042 is a quick-turn tube coupling. In some implementations, the brain housing 102 includes a second coupling 1044 that can be coupled to the outlet line 176 or to another outlet line in order to increase the rate of drainage of fluid out of the brain housing 102 to the perfusate reservoir 104.

The brain housing 102 includes a level sensor 180 to detect the level of fluid (e.g., used perfusate) inside the basin 1022 of the brain housing 102, and the solenoid valve 178 along the housing outlet line 176 is controlled to open or close based on signals generated by the level sensor 180. As depicted in FIG. 10C, the level sensor 180 is coupled to the basin 1022 of the brain chamber 102. In some implementations, the level sensor 180 is coupled to the basin 1022 at the same or similar height along the basin 1022 as the fluid coupling 1046 that fluidly connects the shunt line 156 to the interior of the brain chamber 102. In some implementations, the level sensor 180 is an optical level sensor, such as an infrared level sensor. For example, the solenoid valve 178 is controlled to remain in a closed state and prevent flow of used perfusate from the brain housing 102 into the perfusate reservoir 104 until the level sensor 180 generates a signal indicating that the fluid level inside the brain housing 102 has exceeded a threshold fluid level. In response to the level sensor 180 generating a signal indicating that the fluid level inside the brain housing 102 has exceeded a threshold fluid level, the solenoid valve 178 is opened to allow used perfusate to flow from the brain housing 102 along the housing outlet line 176 to the perfusate reservoir 104. Once the level sensor 180 detects that the fluid level inside the brain housing 102 has fallen below the threshold level, the solenoid valve 178 is closed, which prevents fluid from flowing from the brain housing 102 to the perfusate reservoir 104.

Two stopcocks 181, 182 are positioned along the housing outlet line 176 between the brain housing 102 and the perfusate reservoir 104. An operator of the system 100 can use the stopcocks 181, 182 to sample the used perfusate flowing out of the brain housing 102, for example, to test one of more properties of the used perfusate discharged from the brain 110.

The stopcock 181 along the housing outlet line 176 fluidly couples the housing outlet line 176 to a venous sample line 183, which fluidly couples the brain housing 102 to the automatic sampler system 105. The automatic sampler system 105 can be operated to automatically collect a sample of used perfusate from the brain housing 102, for example, to test one or more characteristics of the used perfusate. A solenoid valve 173 is positioned along the venous sample line 183 between the brain housing 102 and the automatic sampler system 105. In order to automatically collect a sample of perfusate from the venous sample line 183, the stopcock 181 is automatically controlled (e.g., using a servo motor) to fluidly couple the housing outlet line 176 to the venous sample line 183, the solenoid valve 173 along the venous sample line 183 is opened, and the pump 184 of the automatic sampler system 105 is operated to draw used perfusate out of the brain housing 102 along the venous sample line 183, and the solenoid manifold 185 is controlled to direct the used perfusate through the sample collection line 186 and into a sample collection vessel. Referring to FIGS. 1 and 3, the automatic sampler system 105 can be controlled to collect samples of used perfusate 304 from the brain housing 102 at predetermined intervals during the perfusion process. For example, in some implementations, the automatic sampler system 105 is configured to collect samples of used perfusate 304 from the brain housing 102 at the start of a perfusion process ("0 hour"), 6 hours after the start of a perfusion process, 12 hours after the start of a perfusion process, and 24 hours after the start of a perfusion process. Samples can alternatively be collected at any other desired frequency.

The automatic sampler system 105 purges the contents of the venous sample line 183 prior to collecting a fluid sample from the venous sample line 183. For example, prior to sampling fluid from the venous sample line 183, the solenoid valve 173 along the venous sample line 183 is opened, the pump 184 and the solenoid manifold 185 of the automated sampler system 105 are controlled to draw the fluid contained inside the venous sample line 183 through the purge line 187 to a drain or waste container. After a predetermined amount of time has elapsed, the solenoid manifold 185 is operated to direct the fluid flowing along the venous sample line 183 through the sample collection line 186 and into a sample collection vessel. As a result of this purging process, the samples 404 collected by the automatic sampler system 105 from the venous sample line 183 correspond to used perfusate that exited the brain housing 102 at the time of the sample collection, rather than used perfusate that was present in the venous sample line 183 prior to the time of sample collection.

Still referring to FIG. 1, the perfusate reservoir 104 includes a reservoir housing 103 that is configured to receive fresh perfusate from the sensor block 124 along the sensor block outlet line 148 and along the arterial sample line 150, and to receive used perfusate from the brain housing 102 along the housing outlet line 176. The reservoir housing 103 is a watertight container that can be formed of any suitable material including, but not limited to, plastic, metal, or glass. The perfusate reservoir 104 includes a filter bag 101 positioned within the reservoir housing 103 to filter the fluid flowing into the perfusate reservoir 104. In some implementations, the filter bag 101 is formed of a 0.22 μm filter.

In addition to the filter bag 101 positioned inside the reservoir housing 103, the perfusion system 100 includes an in-line mechanical filtration system 1001 that includes a peristaltic filtration pump 1002, a 0.22 μm filter 1004 fluidly coupled to the filtration pump 1002 along a filtration line 1006, and a pressure sensor 1008 positioned along the filtration line 1006 between the filtration pump 1002 and the filter 1004. In order to further filter the perfusate contained in the perfusate reservoir 104 prior to providing the perfusate to the brain 110, the filtration pump 1002 can be operated to draw fluid out of the perfusate reservoir 104 along a reservoir outlet line 179 extending from the perfusate reservoir 104 and along the filtration line 1006, through the filter 1004, and back to the perfusate reservoir 104. The filtration pump 1002 is communicably coupled to the pressure sensor 1008, and the rate of the filtration pump 1002 is controlled to maintain a predetermined range of pressure along the filtration line 1006, as detected by the pressure sensor 1008. In some implementations, the filtration pump 1002 is controlled based on signals from the pressure sensor 1008 to maintain the pressure along the filtration line 1006 within a range of 50 mmHg and 150 mmHg. In some implementations, the filtration pump 1002 is controlled to generate a particular pressure along the filtration line 1006, as measured by pressure sensor 1008, based on the condition of the perfusate and the level of residue in the filter 1004. As the perfusate flows through the filter 1004 of the perfusate filtration system 1001, additional particulates and other potential contaminants are removed from the perfusate before returning the perfusate to the perfusate reservoir 104 and flow the perfusate to the brain 110. The in-line mechanical filtration system 1001 can be operated throughout the process of perfusing the brain 110 to further filter the perfusate any bacteria or contaminates.

The perfusion system 100 also includes a dialysis filtration system 109 that is configured to further filter the perfusate flowing through the system 100 and remove metabolic waste products or other unwanted substances from the perfusate. The dialysis filtration system 109 includes a dialysis pump 190, a dialyzer 191, a dialyzer inlet line 192 coupled to the dialyzer 191, and a dialyzer outlet line 193 coupled to the dialyzer 191. The dialyzer 191 includes a membrane configured filter waste particles out of the perfusate. The dialysis pump 190 is a peristaltic pump that is controlled throughout the perfusion process to draw perfusate from the perfusate reservoir 104 along the dialyzer inlet line 192 and into the dialyzer 191 at a controlled pressure. As the perfusate flows through the dialyzer 191, waste particles within the perfusate are filtered out of the perfusate by the membrane of the dialyzer 191 and the filtered perfusate exits the dialyzer 191 along the dialyzer outlet line 193. A stopcock 1912 is positioned along the dialyzer outlet line 193. The stopcock 1912 can be used to sample perfusate fluid flowing out of the dialyzer 191 to test one of more properties of the perfusate being provided to the perfusate reservoir 104, for example, to test the effectiveness of the dialysis filtration system 109.

The dialysis filtration system 109 includes a first pressure sensor 194 positioned upstream of the dialyzer 191 and a second pressure sensor 195 positioned downstream of the dialyzer 191, and the rate of the dialysis pump 190 is controlled based on pressure signals generated by pressure sensors 194, 195 in order to control the pressure within the dialyzer 191 to provide efficient filtration across the membrane of the dialyzer 191. For example, the pressure drop across the dialyzer 191 can be determined based on the difference between the pressure upstream of the dialyzer 191 measured by the first sensor 194 and the pressure downstream of the dialyzer 191 measured by the second sensor 195, and the pump rate of the dialysis pump 190 can be controlled in order to maintain a pressure drop across the dialyzer 191 within a predetermined range that is sufficient to enable efficient waste removal and nutrient exchange within the dialyzer 191. The dialysis filtration system 109 also includes a resistance valve 196 positioned along the dialyzer outlet line 193 between the pressure sensor 195 and the perfusate reservoir 104. The resistance valve 196 is a pinch valve that is controlled based on the pressure signals generated by pressure sensors 194, 195 along the dialyzer inlet and outlet lines 192, 193, respectively. For example, the resistance valve 196 can be controlled to increase the pressure along the dialyzer outlet line 193 in response to determining, based on the difference between the pressure signals generated by pressure sensors 194, 195, that the pressure within the dialyzer 191 is below a threshold pressure.

As filtered perfusate flows back to the perfusate reservoir 104 along the dialyzer outlet line 193, the waste filtered out of the perfusate flows along the waste line 197 to the waste fluid receptacle 198 positioned on a waste scale 199. As the waste flows into the waste fluid receptacle 198, the waste scale 199 measures, in real-time, the weight of waste contained within the waste fluid receptacle 198.

A resistance valve 1902 is positioned along waste line 197 and is configured to control the rate of flow of waste between the dialyzer 191 and the waste fluid receptacle 198. For example, the resistance valve 1902 can be a pinch valve and, based on signals received from the waste scale 199, the resistance valve 1902 can be adjusted to increase or decrease the flow rate of waste into the waste fluid receptacle 198 in order to maintain a particular rate of waste entering the waste fluid receptacle 198. In some implementations, the resistance valve 1902 is controlled to cause waste to exit the dialyzer 191 and enter the waste fluid receptacle 198 at a rate of 1 gram/minute, as detected by the waste scale 199. In addition, the resistance valve 1902 can be controlled based on the pressure signals generated by pressure sensors 194, 195 along the dialyzer inlet and outlet lines 192, 193, respectively. For example, the resistance valve 1902 can be controlled to increase the pressure along the waste line 197 in response to determining, based on the difference between the pressure signals generated by pressure sensors 194, 195, that the pressure within the dialyzer 191 is below a threshold pressure.

The dialysis filtration system 109 also includes a fresh perfusate reservoir 1904 that contains a supply of perfusate solution and a fresh perfusate pump 1906 that is configured to pump fresh perfusate fluid contained within the fresh perfusate reservoir 1904 into the perfusate reservoir 104 along a fresh perfusate line 1908. The fresh perfusate reservoir 1904 is positioned on a fresh perfusate scale 1910 that is configured to measure the weight of perfusate contained within the fresh perfusate reservoir 1904. The fresh perfusate pump 1906 is controlled to pump fresh perfusate from the fresh perfusate reservoir 1904 into the perfusate reservoir 104 based on signals received from waste scale 199 and signals received from the fresh perfusate scale 1910. For example, based on the signals received from the waste scale 199 indicating an amount of fluid removed from the dialyzer 191 into the waste fluid receptacle 198, the fresh perfusate pump 1906 can be controlled to provide a corresponding amount of fresh perfusate from the fresh perfusate reservoir 1904 into the perfusate reservoir 104, as determined based on the signals received from the fresh perfusate scale 1910. In some implementations, the fresh perfusate pump 1906 is controlled to pump fresh perfusate from the fresh perfusate reservoir 1904 to the perfusate reservoir 104 at the same rate that waste fluid is provided from the dialyzer 191 to the waste fluid receptacle 198, as determined based on signals generated by the waste scale 199 and the fresh perfusate scale 1910.

As the brain is perfused with the perfusate, homeostasis and cellular activity of the brain 110 are maintained throughout the length of the perfusion process. In some implementations, the perfusion of the brain can be used to maintain homeostasis and cellular activity of the brain 24 hours or longer (e.g., 24-48 hours, 48-72 hours, 48-96 hours, 96 hours or longer, etc.) post-mortem. As a result of the restored metabolic and cellular activity provided by the perfusion of the brain, chemical exchanges and reactions occur within the brain 110 throughout the perfusion process, and these reactions can be monitored in real-time using the perfusion system 100. For example, as depicted in FIG. 1, the perfusion system 100 includes an in-line Raman spectroscopy system 107 (also referred to herein as "spectroscopy system 107") that is configured to perform Raman spectroscopy on perfusate flowing through the system 100 and a Raman spectroscopy probe 172 coupled to or near the brain housing 102 for performing Raman spectroscopy on the tissue of the brain 110 in real-time during perfusion of the brain 110.

The in-line Raman spectroscopy system 107 includes a pump 111, a Raman chamber 117, a Raman sample line 123 fluidly coupling the pump 111 to the Raman chamber 117, and Raman spectrometer 119 configured to perform Raman spectroscopy on perfusate contained inside the Raman chamber 117. A stopcock 127 is positioned along the Raman sample line 123 upstream of the pump 111. The stopcock 127 can be used to sample the perfusate flowing to the Raman chamber 117, for example, in order to conduct tests on the perfusate flowing to the Raman chamber 117 to calibrate the Raman spectrometer 119.

In order to accurately perform Raman spectroscopy, the perfusate in the Raman chamber is maintained within a predetermined temperature range that is suitable for Raman spectroscopy. As depicted in FIG. 1, the Raman spectroscopy system 107 includes a heat exchanger 115 upstream of the Raman chamber 117, a first temperature sensor 113 positioned upstream of the Raman chamber 117 and the heat exchanger 115, and a second temperature sensor 121 positioned downstream of the Raman chamber 117 and the heat exchanger 115. As perfusate flows along the Raman sample line 123, the temperature of the perfusate is measured by the first temperature sensor 113, the perfusate is provided to the heat exchanger 115, and the heat exchanger 115 is controlled based on the temperature signals generated by the first temperature sensor 113 to adjust the temperature of the perfusate provided to the Raman chamber 117 to be within the predetermined range. For example, the heat exchanger 115 can be configured to continually adjust (e.g., raise or lower) the temperature of the perfusate flowing through the Raman sample line 123 until the temperature of the perfusate downstream of the Raman chamber 117 measured by the second temperature sensor 121 is within the predetermined temperature range. In some implementations, the heat exchanger 115 is configured to adjust the temperature of the perfusate provided to the Raman chamber 117 to be approximately 26° C.

The Raman spectroscopy system 107 can be used to perform spectroscopy on both the fresh perfusate contained within the perfusate reservoir 104 and used perfusate flowing out of the brain housing 102. For example, as depicted in FIG. 1, the reservoir outlet line 179 that extends from the perfusate reservoir 104 is fluidly coupled to the Raman sample line 123 and, in order to perform Raman spectroscopy on the perfusate contained within the perfusate reservoir 104, a solenoid valve 177 along the Raman sample line 123 downstream of the Raman chamber 117 is closed, the stopcock 127 is controlled (e.g., using a servo-motor) to fluidly couple the reservoir outlet line 179 to the Raman chamber 117, a solenoid valve 129 along the reservoir outlet line 179 between the perfusate reservoir 104 and the Raman chamber 117 is opened, and the pump 111 is operated to draw perfusate from the perfusate reservoir 104, along the reservoir outlet line 179 and the Raman sample line 123, through the heat exchanger 115, and into the Raman chamber 117. In order to perform Raman spectroscopy on the used perfusate flowing out of the brain 110, the stopcock 182, 127 are controlled (e.g., using a servo-motor) to fluidly couple the housing outlet line 176 to the Raman chamber 117, a solenoid valve 139 along the housing outlet line 176 between the brain housing 102 and the Raman chamber 117 is opened, and the pump 111 is operated to draw used perfusate along the housing outlet line 175 and the Raman sample line 123, through the heat exchanger 115, and into the Raman chamber 117. Once the Raman chamber 117 is filled with perfusate, the pump 111 is stopped and the Raman spectrometer 119 is controlled to perform Raman spectroscopy analysis on the perfusate to analyze the chemical composition of the perfusate and identify one or more molecules present in the perfusate. Once the Raman spectrometer 119 has completed performing spectroscopy on the perfusate sample inside the Raman chamber 117, the solenoid valve 177 along the Raman sample line 123 downstream of the Raman chamber 117 is opened and the pump 111 is controlled to pump the perfusate inside the Raman chamber 117 along the Raman sample line 123 to the perfusate reservoir 104.

Figure 4:
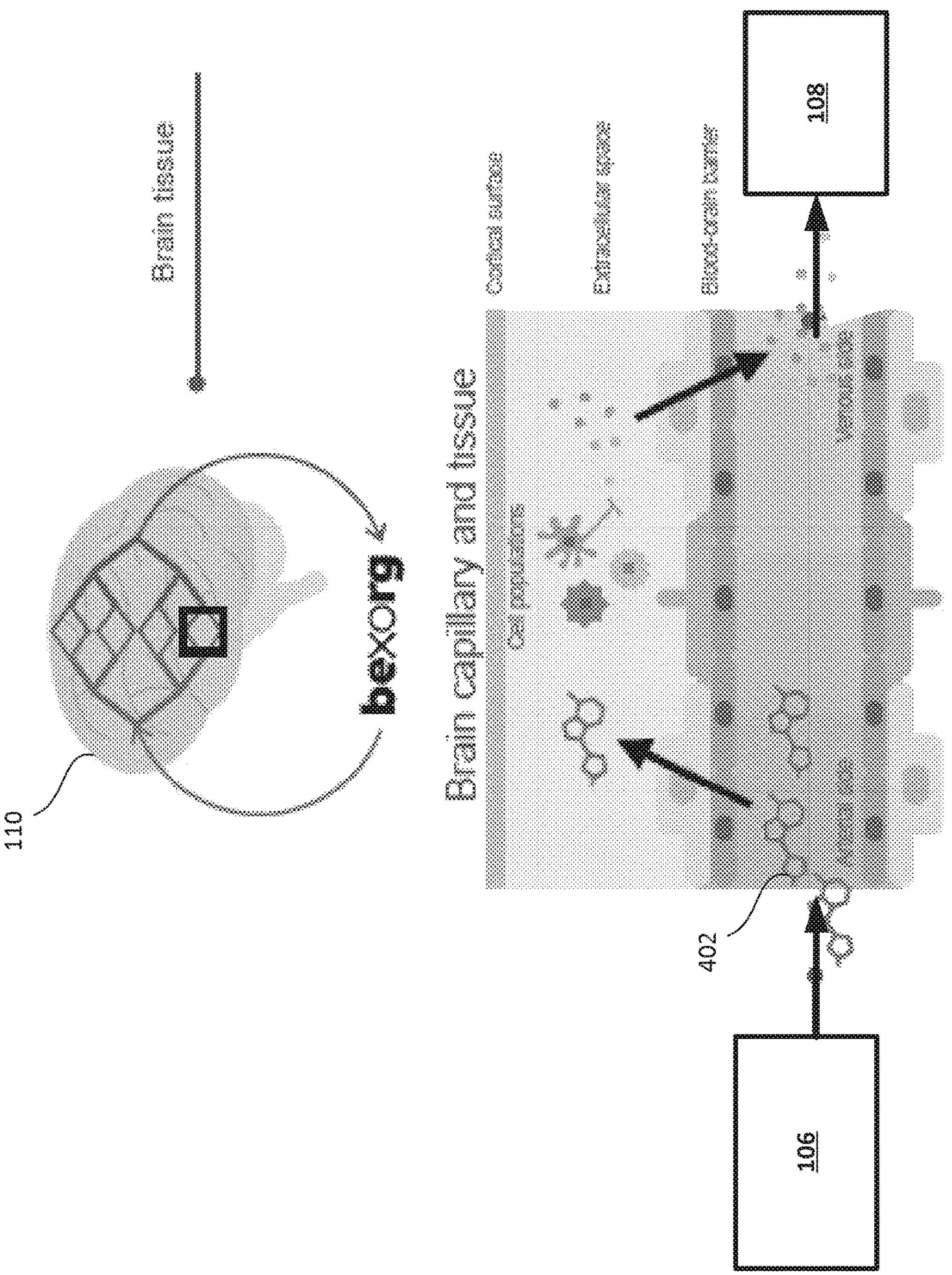
FIG. 4 is a schematic illustration of molecules in perfusate crossing the blood-brain barrier of a brain being perfused by the system of FIG. 1.

By performing Raman spectroscopy on the fresh perfusate inside the perfusate reservoir 104, the chemical composition and proportions of components of the perfusate can be confirmed and adjusted, if needed. In addition, by performing Raman spectroscopy on the used perfusate flowing out of the brain 110, the uptake of chemical compounds by the brain 110 from the perfusate can be determined. For example, the chemical composition of the fresh perfusate provided to the brain 110 is predefined and can be confirmed by performing Raman spectroscopy on the fresh perfusate in the perfusate reservoir 104 using the spectroscopy system 107, as described above. The spectroscopy system 107 can then be used to determine the chemical composition of the used perfusate flowing out of the brain 110, as described above. The known composition of the fresh perfusate provided to the brain 110 can be compared to the chemical composition of the used perfusate flowing out of the brain 110, as determined using the spectroscopy system 107, in order to identify any differences in chemical composition in the fresh perfusate and used perfusate. The identified differences between the fresh perfusate and used perfusate can be used to determine various metabolic processes performed by the brain 110 during perfusion. As an example, the fresh perfusate provided by the brain 110 can include a particular concentration of a particular molecule, and the concentration of the same molecule in the used perfusate flowing out of the brain 110 can be determined using the Raman spectroscopy system 107. In response to determining that the concentration of the particular molecule is higher in the fresh perfusate than in the used perfusate, it can be determined that the particular molecule crossed the blood-brain barrier and that there has been uptake of the particular molecule by the brain 110. As depicted in FIG. 4, the blood-brain barrier selectively regulates passage of molecules 402 from the bloodstream (or perfusate) to the brain 110 through the use of specific proteins, such as transporters and tight junction proteins. In addition, the percentage of uptake of the particular molecule by the brain 110 can be determined by comparing the concentration of the particular molecule in the fresh perfusate and the concentration of the particular molecule in the used perfusate determined using the Raman spectroscopy.

Further, by comparing the chemical composition of the fresh perfusate provided to the brain 110 with the chemical composition of the used perfusate flowing out of the brain 110, as determined using the spectroscopy system 107, metabolic activity of the brain 110 and the health of the brain 110 can be determined in real-time during the perfusion process. For example, based on Raman spectroscopy on the used perfusate using the spectroscopy system 107, it can be determined that the used perfusate flowing out of the brain 110 includes one or more chemical compounds that are not present in the fresh perfusate used perfusate, which indicates that the brain 110 has reacted to one or more components of the perfusate. In addition, based on performing Raman spectroscopy on the used perfusate using the spectroscopy system 107. the response of the brain 110 to the perfusate can be determined, and other related side effects of the response of the brain 110 can be determined.

In addition to determining the response of the brain 110 to perfusate solution in real-time during the perfusion process, the perfusion system 100 can also be used to test the pharmacodynamics of pharmaceutical compounds by the brain 110 in real-time, such as the rate of uptake of the pharmaceutical compounds by the brain and the chemical and metabolic reaction of the brain 110 to the pharmaceutical compounds. For example, referring to FIG. 1, the perfusion system 100 includes a syringe pump manifold 167 that is configured to support one or more syringes and a stepper motor that is configured to control movement of a respective plunger of each of the syringes contained within the manifold 167. The syringe pump manifold 167 is fluidly coupled to the perfusate reservoir 104 along a drug input line 169. Each of the syringes contained within the syringe pump manifold are filled with a pharmaceutical compound, and the syringe pump manifold 167 is controlled throughout the perfusion process to add the pharmaceutical compound to the fresh perfusate in the perfusate reservoir 104 at a predetermined rate. For example, the syringe pump manifold 167 can be controlled to add a pharmaceutical compound into the perfusate at a rate that corresponds to the release profile for oral administration or intravenous administration of the pharmaceutical compound to a human.

The syringe pump manifold 167 is communicably coupled to the Raman spectrometer 119, and the rate of release of the pharmaceutical compound by the syringe pump manifold into the perfusate in the perfusate reservoir 104 can be controlled based on Raman spectroscopy analysis of the perfusate in the reservoir 104 by the spectroscopy system 107. For example, as previously discussed, the Raman spectroscopy system 107 can be used to perform Raman spectroscopy of the fresh perfusate in the perfusate reservoir 104. As the syringe pump manifold 167 operates to deliver a pharmaceutical compound into the perfusate inside the perfusate reservoir 104, the concentration of the pharmaceutical compound in the fresh perfusate can be determined in real-time by performing Raman spectroscopy using the Raman spectroscopy system 107 on perfusate sampled from the reservoir 104. Based on the concentration of the pharmaceutical compound in the fresh perfusate detected by the Raman spectroscopy system 107, the syringe pump manifold 167 can be controlled to increase, decrease, or maintain the rate the pharmaceutical compound is provided to the perfusate reservoir 104 in order to align the concentration of the pharmaceutical compound within the perfusate with the desired release profile in real-time.

In addition, the dialysis filtration system 109 can be used in conjunction with the Raman spectroscopy system 107 to provide a desired release profile of the pharmaceutical compound to the brain 110. As previously discussed, the perfusate system 100 is a closed-loop system. Therefore, any pharmaceutical compound added to the perfusate that is not metabolized by the brain 110 is recirculated within the perfusate. However, the release profile for many pharmaceutical compounds increases to a peak concentration, and then subsequently decreases. Therefore, in order to simulate certain release profiles, the concentration of the pharmaceutical compound within the perfusate needs to be reduced following a peak concentration. The dialysis filtration system 109 can be operated to remove the pharmaceutical compound from the perfusate at a controlled rate in order to cause the concentration of the pharmaceutical compound within the perfusate to decrease corresponding to the desired release profile. For example, as previously discussed, the concentration of the pharmaceutical compound in perfusate contained in the perfusate reservoir 104 can be determined in real-time by performing Raman spectroscopy using the Raman spectroscopy system 107 on perfusate sampled from the reservoir 104. Based on the concentration of the pharmaceutical compound in the fresh perfusate detected by the Raman spectroscopy system 107, the dialysis filtration system 109 can be controlled to decrease the concentration of the pharmaceutical compound in the perfusate at a predetermined rate to align the concentration of the pharmaceutical compound with the desired release profile for the pharmaceutical compound. For example, based on the concentration of the pharmaceutical compound detected in the fresh perfusate by the Raman spectroscopy system 107, the dialysis pump 190 can be controlled to pump perfusate from the perfusate reservoir 104 along the dialyzer inlet line 192 to the dialyzer 191 and the dialyzer 191 removes at least a portion of the pharmaceutical compound from the perfusate. The perfusate with a reduced concentration of the pharmaceutical compound exits the dialyzer 191 and is pumped back to the perfusate reservoir 104 along the dialyzer outlet line 193. The dialysis pump 190 can be controlled to continue flowing perfusate through dialyzer 191 until the Raman spectroscopy system 107 detects that the concentration of the pharmaceutical compound in the perfusate within the perfusate reservoir 104 is below a concentration corresponding to the desired release profile. In some implementations, the flow rate of the dialysis pump 190 is controlled in real time based on the level of pharmaceutical compound within the perfusate detected by the Raman spectroscopy system 107. In some implementations, the dialysis pump 190 is controlled to flow perfusate from the perfusate reservoir 104 at a predetermined rate and for a predetermined duration in order to remove the pharmaceutical compound at a rate corresponding to the desired release profile.

Figure 5:
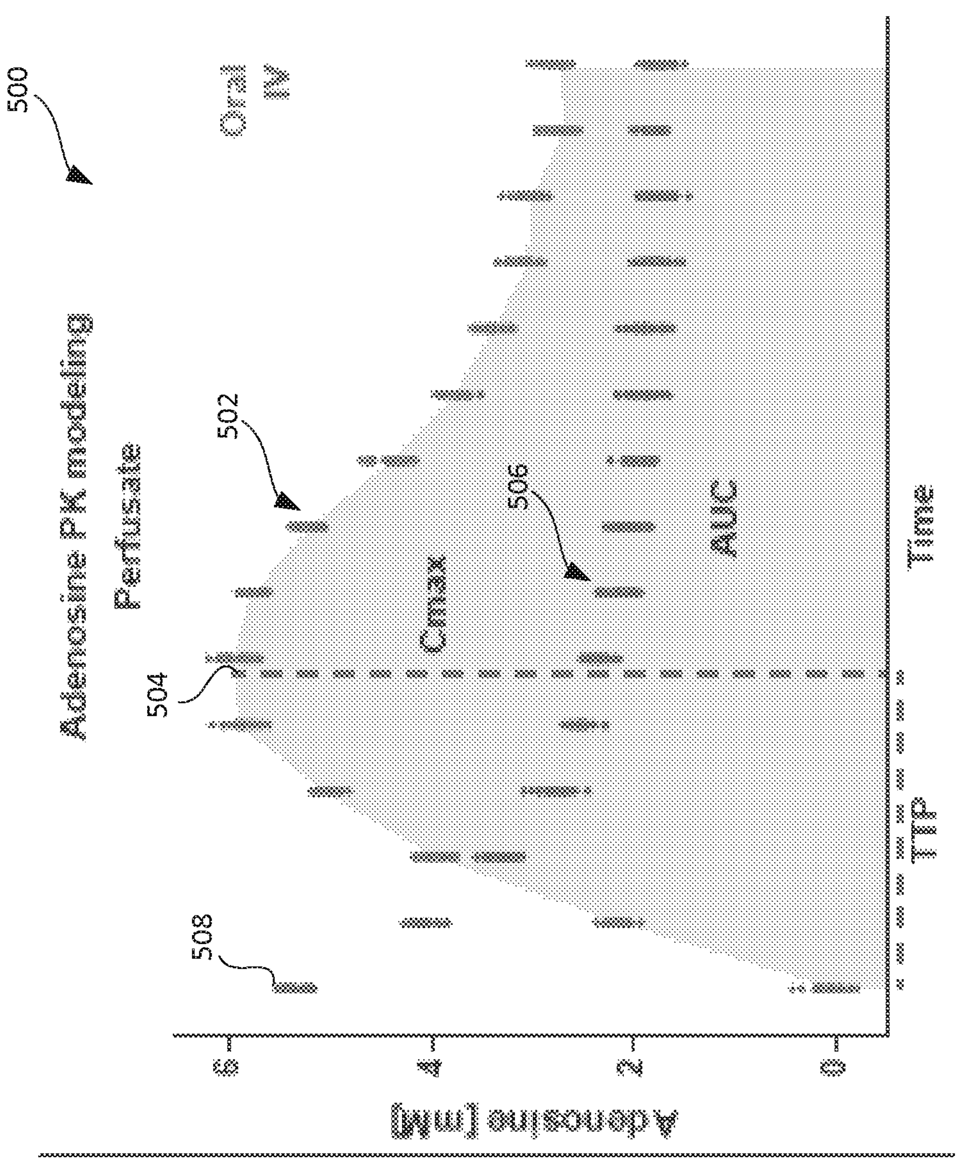
FIG. 5 depicts example Raman spectroscopy data indicating release profiles of rapamycin provided through perfusate of the perfusion system of FIG. 1.

FIG. 5 depicts Raman spectroscopy data 500 generated during example perfusion procedures in which adenosine was added to the perfusate during the perfusion procedure. During a first perfusion procedure, the syringe pump manifold 167 and dialysis filtration system 109 were controlled to adjust the concentration of adenosine within the perfusate in the perfusate reservoir 104 to correspond to a typical release profile 502 for oral administration of adenosine. As can be seen in FIG. 5, the oral administration release profile 502 defines an initial increase in concentration of adenosine until the concentration of adenosine reaches a peak concentration 504, followed by a decrease in concentration of adenosine. In order to administer adenosine to a brain being perfused by the system 100 according to the oral release profile 502, the syringe pump manifold 167 was initially controlled to provide adenosine to the perfusate in the perfusate reservoir 104. As the syringe pump manifold 167 operated to add adenosine to the perfusate in the perfusate reservoir 104, samples of the perfusate from the perfusate reservoir 104 were periodically tested using the Raman spectroscopy system 107, as described above. Based on the Raman spectroscopy data 500, the concentration 502 of adenosine within the fresh perfusate in the perfusate reservoir 104 was tracked in real-time and the rate of the syringe pump manifold 167 was periodically adjusted to reduce the rate at which the concentration of adenosine increased, in accordance with the portion of the release profile 502 before the peak concentration 504. Once the concentration of adenosine in the perfusate in the perfusate reservoir 104 was identified as being equal to the peak concentration 504, as determined based on the Raman spectroscopy data 500 generated by performing Raman spectroscopy system 107, the dialysis filtration system 109 was operated to remove adenosine from the perfusate at a controlled rate to gradually decrease the concentration of adenosine in the perfusate, as depicted in the portion of the release profile 502 after the peak concentration 504. As the dialysis filtration system 109 was operated to remove adenosine from the perfusate, samples of the perfusate from the perfusate reservoir 104 were periodically tested using the Raman spectroscopy system 107, as described above. Based on the Raman spectroscopy data 500, the concentration 502 of adenosine within the fresh perfusate in the perfusate reservoir 104 was tracked in real-time and the dialysis filtration system 109 was controlled to progressively reduce the rate at which the concentration of adenosine within the perfusate decreased, as depicted in the portion of the release profile 502 after the peak concentration 504.

During a second perfusion procedure on a second brain, the syringe pump manifold 167 and dialysis filtration system 109 were controlled to cause the concentration of adenosine within the perfusate in the perfusate reservoir 104 to correspond to a typical release profile 506 for intravenous (IV) administration of adenosine. As can be seen in FIG. 5, the IV administration release profile 506 defines a peak initial increase concentration 508 of adenosine that decrease exponentially. In order to administer adenosine according to the IV release profile 506 to a brain being perfused by the system 100, the syringe pump manifold 167 was controlled to provide an initial bolus of adenosine into the perfusate in the perfusate reservoir 104 to achieve the initial peak concentration 508 of adenosine in the perfusate. The initial peak concentration 508 of adenosine in the perfusate was confirmed by performing Raman spectroscopy on a sample of perfusate from the perfusate reservoir 104, as described above. Once the initial peak concentration 508 was provided to the perfusate by the syringe pump manifold 167, as confirmed based on the Raman spectroscopy data 500 generated by the Raman spectroscopy system 107, the dialysis filtration system 109 was operated to remove adenosine from the perfusate at a controlled rate to exponentially decrease the concentration of adenosine in the perfusate in accordance with the IV release profile 506. As the dialysis filtration system 109 was operated to remove adenosine from the perfusate, samples of the perfusate from the perfusate reservoir 104 were periodically tested using the Raman spectroscopy system 107, as described above. Based on the Raman spectroscopy data 500, the concentration 506 of adenosine within the fresh perfusate in the perfusate reservoir 104 was tracked in real-time and the dialysis filtration system 109 was dynamically controlled to exponentially reduce the rate at which the concentration of adenosine within the perfusate in accordance with the IV release profile 506.

Referring back to FIG. 1, as the pharmaceutical compound flows from the one or more syringes in the syringe pump manifold 167 into the perfusate in the perfusate reservoir 104, the perfusate with the pharmaceutical compound is simultaneously provided to the brain 110 from the perfusate reservoir 104 along the organ line 144 and the used perfusate exits the brain 110 into the basin 1022 of the brain housing 102, as previously described. The Raman spectroscopy system 107 can be controlled to perform Raman spectroscopy on the used perfusate flowing out of the brain housing 102 in order to determine the effects of the pharmaceutical compound on the brain 110. For example, at predetermined intervals throughout the perfusion process, the solenoid valve 139 along the housing outlet line 176 between the brain housing 102 and the Raman chamber 117 is opened, and the pump 111 is operated to draw used perfusate along the housing outlet line 175 and the Raman sample line 123, through the heat exchanger 115, and into the Raman chamber 117. As used perfusate flows through the Raman chamber 117, the Raman spectrometer 119 is controlled to perform Raman spectroscopy analysis on the used perfusate to analyze the chemical composition of the used perfusate. The effect of the pharmaceutical compound on the brain 110 can be determined based on the chemical composition of the used perfusate determined by the Raman spectroscopy system 107. For example, the spectroscopy analysis of the used perfusate can be used to determine the concentration of the pharmaceutical compound present in the used perfusate. In response to detecting that the concentration of pharmaceutical compound in the used perfusate flowing out of the brain 110 is lower than the concentration of the pharmaceutical compound in the fresh perfusate in the perfusate reservoir 104 at a corresponding time, it can be determined that the brain has metabolized (e.g., "taken up") at least a portion of the pharmaceutical compound. As a result, the concentration of the pharmaceutical compound in the used perfusate detected by the Raman spectroscopy system 107 can be used to determine whether the pharmaceutical compound is capable of crossing the blood-brain barrier and the rate at which the brain 110 has metabolized the pharmaceutical compound.

The used perfusate flowing out of the brain 110 can also be analyzed by the Raman spectroscopy system 107 to determine one or more molecules generated by the brain 110 in response to the to the pharmaceutical compound. For example, prior to adding a pharmaceutical compound to the perfusate, the chemical composition of the used perfusate flowing out of the brain 110 can be analyzed by the Raman spectroscopy system 107 in order to form a baseline composition. After the pharmaceutical compound has been introduced to the perfusate and flowed to the brain 110, the chemical composition of the used perfusate flowing out of the brain 110 can be analyzed by the Raman spectroscopy system 107 and compared to the baseline chemical composition for the used perfusate to determine one or more molecules that are present in the used perfusate flowing out of the brain 110 following the introduction of the pharmaceutical compound that were not present prior to the introduction of the pharmaceutical compound. The molecules produced by the brain 110 in response to the introduction of the pharmaceutical compound and detected in the used perfusate by the spectroscopy system 107 can be used to determine the reaction of the brain 110 to the pharmaceutical compound, the likely efficacy of the pharmaceutical compound on treating the targeted disease, and potential side effects that may result from the pharmaceutical compound. As a result, potential new drugs can be tested using the perfusate system 100 to accurately determine their likely effectiveness in treating the target disease in humans.

Figure 11B:
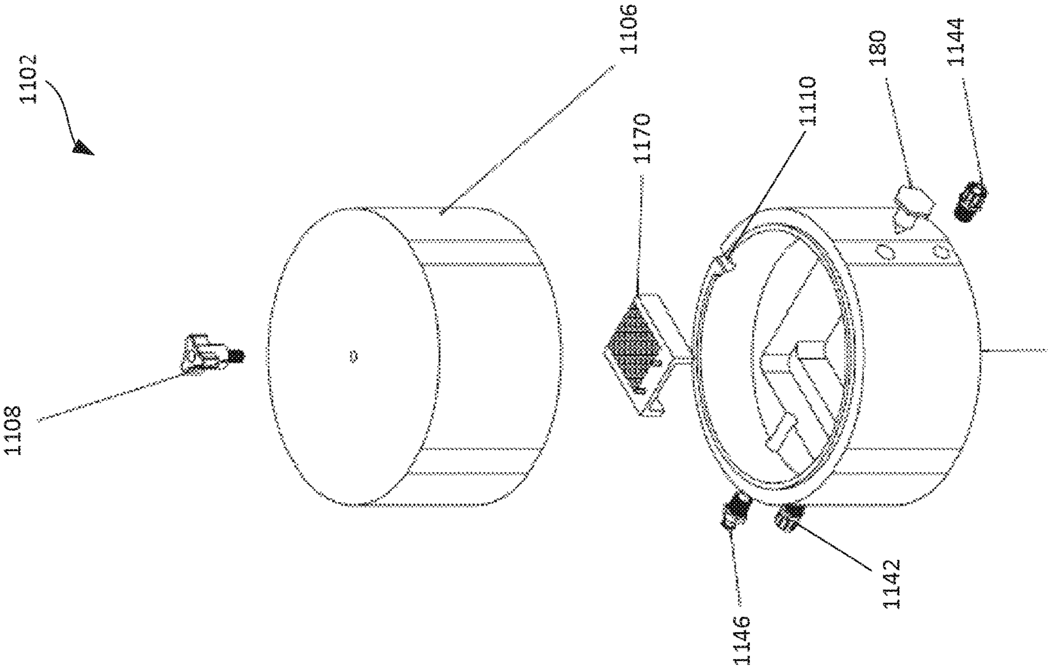
FIG. 11B is an exploded view of the example brain housing of FIG. 11A.
Figure 11A:
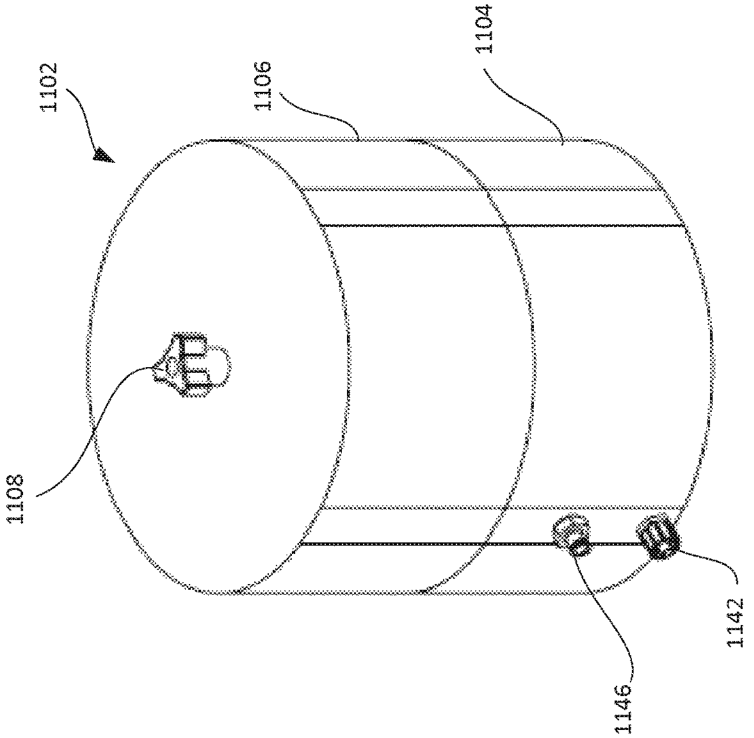
FIG. 11A is a perspective view of another example brain housing.

As previously discussed, the perfusion system 100 also includes a Raman spectroscopy probe 172 that is coupled to or positioned near the brain housing 102 for performing Raman spectroscopy on the tissue of the brain 110 in real-time during perfusion of the brain 110. Once the brain 110 is fluidly coupled to the organ line 144 and is positioned inside the brain housing 102, the Raman spectroscopy probe 172 is positioned on the surface of the brain 110 and can be operated periodically throughout the perfusion process to perform Raman spectroscopy on the tissue of the brain 110 in real-time as the brain is perfused. Referring to FIGS. 11A and 15, in some implementations, the brain housing 102 includes a lid 1106 removably coupled to a basin 1104 and, in order to position the Raman spectroscopy probe 172 on or near the surface of the brain 110, a lid 1106 of the brain housing 102 is removed from the basin 1104. In some implementations, the Raman spectroscopy probe 172 is incorporated into the brain housing 102 (e.g., into a lid 1106 of the housing 102) and the housing 102 can remain closed while performing Raman spectroscopy on the brain 110 inside the housing 102.

Similar to the Raman spectroscopy data generated for the perfusate by the Raman spectroscopy system 107, the data generated by the Raman spectroscopy probe 172 can be used to determine the metabolic activity of the brain 110 and chemical compounds generated by the brain 110 in real-time throughout the perfusion process. For example, at the beginning of the perfusion process, the Raman spectroscopy probe 172 can be controlled to perform Raman spectroscopy on the brain 110 to identify molecules and chemical compounds present in the tissue of the brain 110 in order to form a baseline spectroscopy reading for the brain tissue. After the brain 110 has been perfused with the perfusate for a predetermined period, the Raman spectroscopy probe 172 can be controlled to perform Raman spectroscopy on the brain 110 and the results can be compared to the baseline spectroscopy reading for the brain tissue to determine changes in the types and concentrations of molecules present in the tissue of the brain 110 compared to the baseline. These changes in the molecular composition of the brain tissue in response to perfusion of the brain 110 detected by the Raman spectroscopy probe 172 can be used to determine the effectiveness of the perfusion process, as well as predict the length of time the brain 110 can be effectively perfused, for example, before the brain 110 undergoes significant swelling.

Similar to the Raman spectroscopy system 107, the Raman spectroscopy probe 172 can also be used to determine the effect of a pharmaceutical compound on the brain 110. As discussed above, the syringe pump manifold 167 and the dialysis filtration system 109 can be operated to provide a pharmaceutical compound to the brain 110 through the perfusate at a rate corresponding to a particular release profile. As the pharmaceutical compound is simultaneously provided to the brain 110 from the perfusate reservoir 104, the Raman spectroscopy probe 172 is controlled to perform Raman spectroscopy on the tissue of the brain 110 at predetermined intervals as the pharmaceutical compound is provided to the brain 110.

The data generated by the Raman spectroscopy probe 172 can be used to determine whether the pharmaceutical compound is capable of crossing the blood-brain barrier. The pharmaceutical compound can be determined as capable of crossing the blood-brain barrier in response to detecting that one or more chemical compounds corresponding to the pharmaceutical compound are present in the tissue of the brain 110 using the Raman spectroscopy probe 172. In addition, the percentage of the pharmaceutical compound taken up and metabolized by the brain 110 can be determined based on the concentration of one or more chemical compounds corresponding to the pharmaceutical compound that is detected in the tissue of the brain 110 by the Raman spectroscopy probe 172.

In addition, the Raman spectroscopy probe 172 can be used to determine one or more chemical compounds generated by the brain 110 in response to administration of the pharmaceutical compound. For example, the Raman spectroscopy probe 172 can be controlled to perform Raman spectroscopy on the tissue of the brain 110 at predetermined intervals as a pharmaceutical compound is provided to the brain 110 through the perfusate. The results can be compared to a spectroscopy analysis of the tissue of the brain 110 taken prior to introduction of the pharmaceutical compound to the perfusate in order to determine changes in the types and concentrations of molecules present in the tissue of the brain 110 resulting from the introduction of the pharmaceutical compound. These changes in the molecular composition of the brain tissue in response to introduction of the pharmaceutical compound that are detected by the Raman spectroscopy probe 172 can be used to determine the reaction of the brain 110 to the pharmaceutical compound. For example, the molecules produced by the brain 110 in response to the introduction of the pharmaceutical compound into the perfusate and detected in the brain tissue by the Raman spectroscopy probe 172 can be used to determine the reaction of the brain 110 to the pharmaceutical compound, the likely efficacy of the pharmaceutical compound on treating the targeted disease, and potential side effects that may result from the pharmaceutical compound. As a result, potential new drugs can be tested using the perfusate system 100 to accurately determine their likely effectiveness in treating the target disease in humans.

Using the Raman spectroscopy probe 172 and the Raman spectroscopy system 107 to take Raman spectroscopy measurements on the tissue of the brain 110 and the used perfusate flowing out of the brain 110, respectively, in real-time throughout the perfusion process allows for real-time analysis of the chemical processes occurring in the brain 110 during perfusion without requiring samples of the brain tissue to be removed during the perfusion process. As a result, the sterility and functionality of the brain 110 can be more closely regulated and maintained, which improves and prolongs the perfusion process.

In addition, the data generated by performing Raman spectroscopy on the brain tissue using probe 172 and on the used perfusate using the Raman spectroscopy system 107 can be provided to a trained machine learning model in order to predict one or more characteristics about the brain 110. For example, by aggregating the Raman spectroscopy data collected throughout numerous perfusion processes on respective brains, a machine learning model can be trained to identify Raman spectroscopy data corresponding to particular responses by a human brain to a particular compound.

Once the machine learning model has been trained, the Raman spectroscopy data generated by the sensor probe 172 and/or spectroscopy system 107 following introduction of a pharmaceutical compound into the perfusate can be provided to the trained machine learning model to predict certain responses or reactions relating to the administration of the pharmaceutical compound, such as a metabolic pathway of the pharmaceutical compound in the brain, an activation or deactivation of certain gene pathways in the brain, and/or physiological changes to the brain (e.g., swelling, tissue damage, infection, etc.). For example, the Raman spectroscopy data generated by the sensor probe 172 and/or spectroscopy system 107 indicating the changes in chemical bonds within the brain can be provided to a trained machine learning model, which can utilize the Raman spectroscopy data to determine the likelihood that the brain is currently experiencing swelling or will experience swelling during the perfusion procedure.

The machine learning model can be implemented as any appropriate type of machine learning model, e.g., including one or more of: a neural network, or a random forest, or a support vector machine, or a linear regression model. Further, the machine learning model can have any appropriate architecture that enables the machine learning model to perform its described functions, e.g., processing a model input that is based on Raman spectroscopy of brain tissue or used perfusate that has passed through brain tissue to generate a prediction characterizing the brain. For example, for a machine learning model implemented as a neural network model, the architecture of the neural network can include any appropriate types of neural network layers (e.g., convolutional layers, attention layers, fully connected layers, recurrent layers, message passing layers, pooling layers, transformer layers, and so forth) in any appropriate number (e.g., 3 layers, or 10 layers, or 25 layers) and connected in any appropriate configuration (e.g., as a directed graph of layers).

The model input provided to the machine learning model can represent the Raman spectroscopy data as an ordered collection of numerical values, e.g., a vector, matrix, or other tensor of numerical values. For instance, the Raman spectroscopy data can include a wavelength axis, representing the energy shift from the laser light and an intensity axis representing the amount of scattered light at each energy level. The model input can include Raman spectroscopy data captured at one time point, or at a sequence of multiple time points, e.g., that are spaced at regular intervals in a time window. The model output generated by the machine learning model can be, e.g., a classification output (e.g., that classifies the model input into a category from a predefined set of categories), or a regression output (e.g., that predicts a continuous value based on the model input), or any other appropriate type of model output.

The machine learning model can be trained on a set of training examples by a machine learning training technique. Each training example can include: (i) a training input that includes Raman spectroscopy data generated by performing Raman spectroscopy on brain tissue of a brain or on used perfusate that has passed through the brain tissue of the brain, and (ii) a target output defining a model output that should be generated by the machine learning model by processing the training input. The target output can characterize one or more characteristics of the brain, e.g., a metabolic pathway of a pharmaceutical compound that has been provided to the brain (e.g., in perfusate passed through the brain), an activation or deactivation of certain gene pathways in the brain, or physiological changes to the brain (e.g., swelling, tissue damage, infection, etc.). The target outputs included in the training examples may be generated based on experimental measurements or observations of brains during previous perfusion experiments.

Training the machine learning model on the set of training examples can include, for each training example, training the machine learning model to reduce a discrepancy between: (i) a predicted output generated by processing the training input of the training example using the machine learning model, and (ii) the target output specified by the training example. More specifically, the machine learning model can be trained to optimize an objective function that, for each training example, measures an error between: (i) a predicted output generated by processing the training input of the training example using the machine learning model, and (ii) the target output specified by the training example. The objective function can measure the error, e.g., as a cross-entropy error, or as a squared error, or in any other appropriate way.

Figure 6:
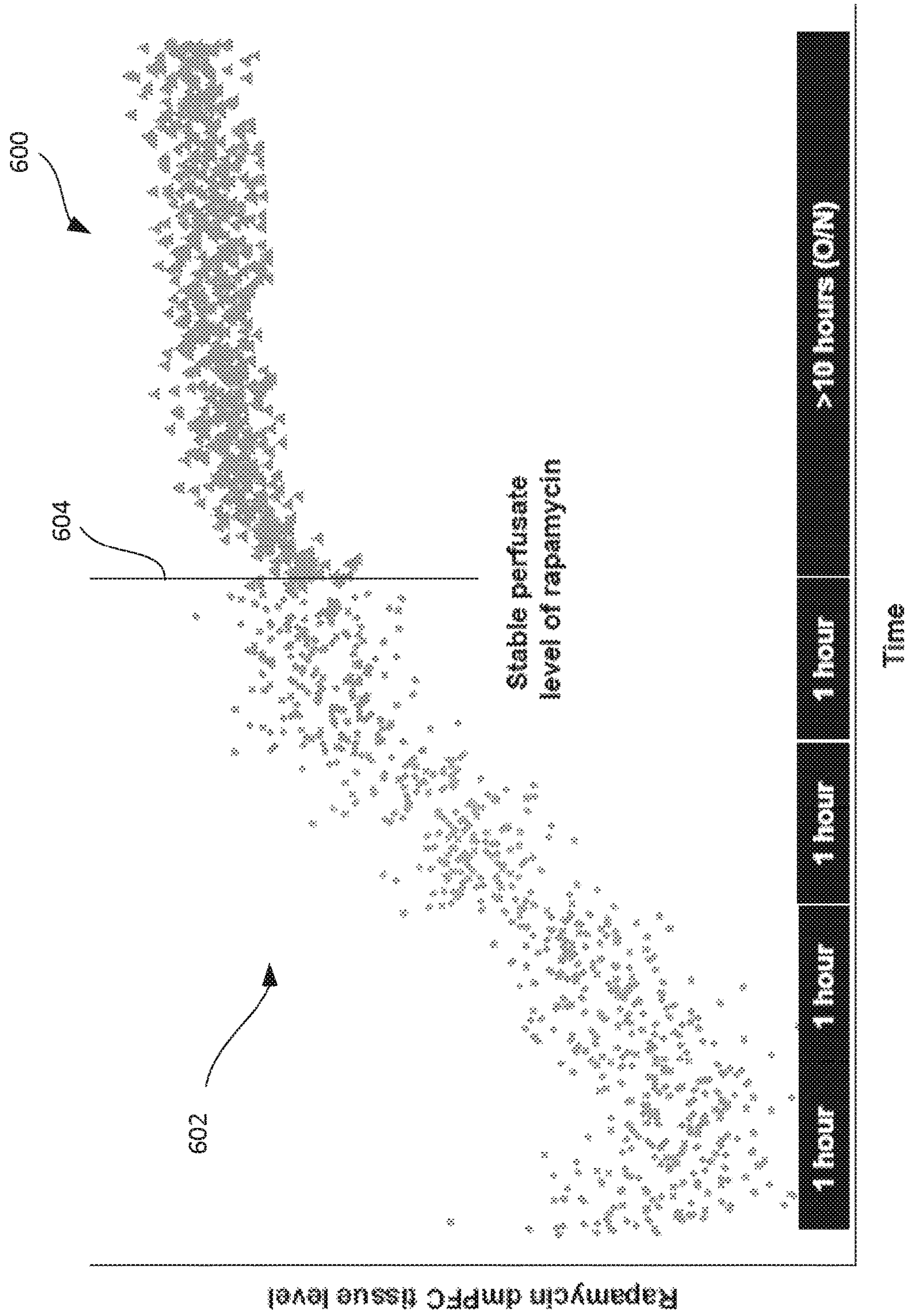
FIG. 6 depicts example Raman spectroscopy data indicating the concentration of rapamycin in the tissue of a brain following introduction of rapamycin into the perfusate of the system of FIG. 1.

FIG. 6 depicts Raman spectroscopy data 500 generated during an example perfusion procedure in which the drug rapamycin was provided to the brain 110. During perfusion of the brain 110 using the perfusion system 100, the syringe pump manifold 167 was controlled to provide rapamycin to the perfusate in the perfusate reservoir 104 at a particular rate, which was then provided to the brain 110 along the organ line 144. As the perfusate containing the rapamycin was provided to the brain 110, Raman spectroscopy was performed on the tissue of the dorsomedial prefrontal cortex (dmPFC) of the brain 110. As can be seen from the Raman spectroscopy data 600 in FIG. 6, the concentration 602 of rapamycin present in the brain 110 continually increased until a stable concentration 604 was reached. Based on the Raman spectroscopy data 600 indicating the presence of rapamycin in the tissue of the dmPFC of the brain 110, it was determined that the rapamycin in the perfusate was able to cross the blood-brain barrier of the brain 110. In addition, based on the Raman spectroscopy data 600, the rate of uptake and metabolism of rapamycin by the brain 110 for the particular release profile of rapamycin provided by the perfusate system 100 was determined.

Referring back to FIG. 1, the perfusate system 100 also includes a drain line 143 fluidly coupled to a waste container 145 configured to receive perfusate from the venous circuit 108. The waste container 145 can be, for example, a rigid, liquid tight container formed of glass or plastic. Alternatively, the waste container 145 can be a plastic bag. A solenoid valve 147 is positioned along the drain line 143 upstream of the waste container 145 and is configured to control flow of used perfusate to the waste container 145. The drain line 143 and the waste container 145 can be used to drain used perfusate from the system 100 without sending the used perfusate back to the perfusate reservoir 104. To drain perfusate from the system 100, the solenoid valve 178 along the housing outlet line 176 between the brain housing 102 and the perfusate reservoir 104 is closed, the solenoid valve 139 along the housing outlet line 176 between the brain housing 102 and the Raman chamber 117 is opened, the solenoid valve 177 along the Raman sample line 123 upstream of the waste container 145 is closed, the solenoid valve 147 along the drain line 143 is opened, and the pump 111 is operated to pump used perfusate along the housing outlet line 175, the Raman sample line 123, and the drain line 143 into the waste container 145. The waste container 145 is positioned on a waste scale 157 configured to record the weight of perfusate contained in the waste container 145. In some implementations, the solenoid valve 177 along the Raman sample line 123 upstream of the waste container 145 and the solenoid valve 147 along the drain line 143 are controlled based on signals generated by the waste scale 157.

At the beginning of the perfusion process, an initial flush of the brain 110 with perfusate is typically performed in order to remove toxins and other unwanted chemical compounds that have built up in the brain 110 during the post-mortem period prior to perfusion During the initial flush of the brain 110, the used perfusate flowing out of the brain 110 is sent to the waste container 145 rather than back to the perfusate reservoir 104. In order to sufficiently remove toxins and other unwanted chemical compounds that have built up in the brain 110 during the post-mortem period prior to perfusion, the brain 110 is flushed with a predetermined amount of perfusate that is not recirculated through the perfusate reservoir 104. During the initial flush of the perfusate process, the solenoid valve 177 along the Raman sample line 123 upstream of the waste container 145 is closed and the solenoid valve 147 along the drain line 143 is open to direct used perfusate flowing out of the brain 110 along the housing outlet line 176 and the Raman sample line 123 to the waste container 145. Throughout the initial flush of the brain 110, the waste scale 157 measures the weight of used perfusate inside the waste container 145 in real-time. In response to the waste scale 157 detecting that a predetermined amount of used perfusate has been provided to the waste container 145 during the initial flush, the solenoid valve 177 along the Raman sample line 123 upstream of the waste container 145 and the solenoid valve 178 along the housing outlet line 176 between the brain housing 102 and the perfusate reservoir 104 are each opened and the solenoid valve 147 along the drain line 143 is closed, which directs used perfusate flowing along the housing outlet line 176 and the Raman sample line 123 back to the perfusate reservoir 104. In some implementations, the brain 110 is initially flushed with 500 mL of perfusate, as detected by the waste scale 157.

In some implementations, the drain line 143 and the waste container 145 are used to drain the venous circuit 108 at the end of a perfusion process. For example, at the end of the perfusion process, solenoid valve 177 along the Raman sample line 123 upstream of the waste container 145 is closed, the solenoid valve 147 along the drain line 143 is opened, and the pump 111 is operated to draw perfusate from the brain housing 102 and the perfusate reservoir 104 along the Raman sample line 123 into the waste container 145 to drain the brain housing 102, the perfusate reservoir 104, and the fluid lines of the venous circuit 108 of used perfusate.

Referring to FIG. 1, the perfusate system includes a computer system 188 that is communicably coupled to the electrical components of the perfusate system 100 including, but not limited to the pumps 111, 114, 190, 1002, 1906, the heat exchangers 115, 118, the oxygenator 116, the gas mixer 120, the electronic pressure regulators 162, 166, the sensor probes 128, the level sensor 125, the pressure sensors 140, 141, 164, 168, 195, 1008, the flow sensors 130, 142, the temperature sensors 113, 121, the resistance valves 152, 196, 1902, the syringe pump manifold 167, the scales 137, 157, 174, 199, 1910, the solenoid valves 129, 133, 139, 147, 149, 151, 158, 159, 171, 173, 177, 178, the Raman spectrometer 119, and the Raman spectroscopy probe 172. In some implementations, the computer system 188 can be in wireless or wired communication with the electronic components of the perfusate system 100. In some implementations, a display 189 of the computing device 188 is configured to display data generated by the perfusate system 100. For example, sensor data generated by the sensor probes 128 can be transmitted to the computer system 188 in real-time, and the display 189 can be configured to display sensor data received from the sensor probes 128. In some implementations, the data generated by the perfusate system 100 (e.g., the data sensor data generated by the sensor block 124 and Raman spectroscopy data generated by the Raman spectroscopy system 107 and the Raman spectroscopy probe 172) is transmitted in real-time to the computer system 188, and the computer system 188 is configured to transmit the data generated by the perfusate system 100 to a remote database for storage. The computer system 188 is also configured to communicably couple and controls the electronic components of the perfusate system 100 to perform the perfusion process as described herein. For example, the computer system 188 is configured to receive data from the pressure sensor 141 and the flow sensor 142, and based on the sensor data, control the second electronic pressure regulator 168 to adjust the pulsatile flow provided by the pulse generator 136 along the organ line 144.

An example process of calibrating the perfusion system 100 and performing perfusion of a brain 110 using the system 100 will now be described with reference to FIGS. 1-2D and 4.

Prior to performing a perfusion procedure, reusable components of the perfusion system 100 that come into contact with the perfusate during a perfusion process are sterilized (e.g., using autoclave) including, but not limited to, the pulse generator 136, the perfusate reservoir 104, the sensor block 124 and sensor probes, the brain housing 102, the Raman chamber 117, the oxygenator 116, the pressure sensor 140, 141, 194, 195, 1008, and the flow sensors 130, 142. After sterilization of the relevant system components is complete, each of the components of the system 100 is positioned inside a clean room that houses the perfusion system 100 throughout the perfusion process. In some implementations, the clean room that houses the perfusion system 100 is provided with a positive pressure system that forces positive pressure into the clean room to prevent contamination of the perfusion system. Once the reusable components of the perfusion system 100 have been sterilized and positioned in the clean room, the various fluid lines 112, 123, 131, 144, 143, 146, 148, 150, 156, 176, 183, 192, 193, 197, 179, 1908 are attached to the system 100 as depicted in FIG. 1 to form the arterial circuit 106, the venous circuit 108, the in-line Raman spectroscopy system 107, and the dialysis filtration system 109.

Once components of the perfusion system 100 are positioned in the clean room and fluidly coupled as depicted in FIG. 1 and prior to adding perfusate to the system, the air supply system 138 and the pressure sensors 140, 141 along the organ line 144 are calibrated. For example, the resistance valve 152 along the organ line 144 and the solenoid valves 158, 159 along the brain housing shunt line 156 and the organ line 144, respectively, are closed, and a flow of pressurized air is provided from the air source 160 to the first electronic pressure regulator 162. The first electronic pressure regulator 162 is operated, based on pressure signals generated by the first pressure sensor 164, to regulate the air flow to a pressurized air stream having a pressure of about 5 psi. The pressurized air stream is then provided from the first electronic pressure regulator 164 to the second electronic pressure regulator 166. As previously discussed, the second pressure regulator 166 has tighter tolerances compared to the first electronic pressure regulator 162 and is configured to provide a pressurized air stream to the air inlet 230 of the pulse generator 136 at a particular pressure (e.g., 5 psi). The smoothed, pressurized air stream flows from the second electronic pressure regulator 166, through the pulse generator 136, along the organ line 144, and to the brain housing 102. As the pressurized air stream flows from the second electronic pressure regulator 166 along the air supply line 161 and the organ line 144, the pressure of the air stream is measured by the second pressure sensor 168 along the air supply line 161 and the pressure sensors 140, 141 along the organ line 144. The pressure measured by the second pressure sensor 168 along the air supply line 161 is compared to the pressure measured by the pressure sensors 140, 141 along the organ line 144, and the pressure sensors 140, 141 along the organ line 144 are calibrated based on any differences between the pressure measured by the second pressure sensor 168 along the air supply line 161 and the pressure measured by the respective pressure sensor 140, 141 along the organ line 144.

In some implementations, the pressure sensor 141 downstream of the resistance valve 152 is further calibrated using air provided from the second pressure regulator 166 along the air calibration line 163. For example, pressurized air is provided from the second pressure regulator 166 to the organ line along the air calibration line 163 through stopcock 155. The stopcock 154 upstream of the pressure sensor 141 and the stopcock 155 downstream of the pressure sensor 141 are each closed to generate a stable air pressure along the organ line 144 between the stopcocks 154, 155 corresponding to the air pressure provided by the second pressure regulator 166. Once the stopcocks 154, 155 are closed, the pressure sensor 141 can be calibrated based on any difference in the pressure measured by the pressure sensor 141 can be compared to the pressure provided by the second pressure regulator 166, Once the air supply system 138 and the pressure sensors 140, 141 along the organ line 144 are calibrated, fresh perfusate is added to the perfusate reservoir 104. In some implementations, the perfusate is sterilized using ultraviolet irradiation prior to being provided to the perfusate reservoir 104. Once the perfusate reservoir 104 is filled with fresh perfusate, the system 100 is controlled to flood the fluid lines 112, 123, 131, 144, 146, 150, 156, 176, 183, 192, 193, 197, 179, 1908 of the arterial circuit 106, the venous circuit 108, the Raman spectroscopy system 107, and the dialysis filtration system 109 with fresh perfusate in order to remove any air contained within the fluid lines. In order to "flood" the system 100 with perfusate and purge air from the fluid lines of the system 100, the solenoid valves 133, 158, 159, 177, 129, 139 of the arterial circuit 106, the venous circuit 108, the Raman spectroscopy system 107 are opened, the solenoid valves 149, 151, 178 between the sensor block 124 and the brain housing 102 and the perfusate reservoir 104 are closed, and the flow pump 114, the dialysis pump 190, and the pump 111 of the Raman spectroscopy system 107 and the pulse generator 136 are each controlled to flow perfusate from the perfusate reservoir 104 through fluid lines 112, 123, 131, 144, 146, 150, 156, 176, 183, 192, 193, 197, 179, 1908 of the arterial circuit 106, the venous circuit 108, the Raman spectroscopy system 107, and the dialysis filtration system 109, as described in detail above. The perfusate flows through the fluid lines to the sensor block 124 and the brain housing 102. Once the level sensor 180 in the brain housing 102 detects that the brain housing 102 is filled to a desired level with perfusate, the solenoid valve 178 between the brain housing 102 and the perfusate reservoir 104 opens to allow perfusate to flow from the brain housing 102 to the perfusate reservoir 104. Similarly, once the level sensor 125 in the sensor block 124 detects that the sensor block 124 is filled to a desired level with perfusate, the solenoid valves 149, 151 between the sensor block 124 and the perfusate reservoir 104 open to allow perfusate to flow from the sensor block 124 to the perfusate reservoir 104. As the perfusate flows through the system 100, the air contained within the fluid lines 112, 123, 131, 144, 146, 150, 156, 176, 183, 192, 193, 197, 179, 1908 is vented out of the fluid lines into a head space at the top of the perfusate reservoir 104, a head space at the top of the sensor block 124, and a head space at the top of the brain housing 102. The pumps 114, 190, 111 and pulse generator 136 continue to operate to pump perfusate throughout the system 100 until all of the air is vented out of the fluid lines 112, 123, 131, 144, 146, 150, 156, 176, 183, 192, 193, 197, 179, 1908. In addition, the air supply system 138 is configured to provide a pulsatile stream of pressurized air to the pulse generator 136 sufficient to cause the pulse generator 136 to force any air contained in the central housing 202 of the pulse generator 136 downstream to the sensor block 124 or the brain housing 102.

Once the arterial circuit 106, the venous circuit 108, the Raman spectroscopy system 107, and the dialysis filtration system 109 have been flood with perfusate, the solenoid valves 133, 158 along the oxygenator shunt line 131 and the brain housing shunt line 156 are closed, and an initial sample of the perfusate is collected using one of the stopcocks 127, 132, 135, 153, 154, 155, 181, 182, 1912. The initial ("zero hour") sample of the perfusate can be tested using various techniques (e.g., spectroscopy, gene sequencing, cytokine analysis, anti-body analysis, genomic analysis, transcriptomic analysis, proteomic analysis, metabolomic analysis) in order to determine baseline measurements for the perfusate, including the chemical composition of the perfusate. For example, a user can use other laboratory equipment to test the initial perfusate sample collected from the system 100, for example, to perform gene sequencing, cytokine analysis, anti-body analysis, genomic analysis, transcriptomic analysis, proteomic analysis, metabolomic analysis. In addition, an initial sample of the perfusate can be tested e using the Raman spectroscopy system 107, as described herein.

Once the system 100 is flooded with perfusate, the sensor probes 128 in the sensor block 124 are controlled to take initial sensor readings, which are used to calibrate the sensor probes 128. In some implementations, the sensor probes 128 are calibrated using electronic calibration devices, such as the i-STAT analyzer device manufactured by Abbott.

Once the system 100 is flooded with perfusate and the sensor probes 128 have been calibrated, the initial conditions for the gas mixer 120 and heat exchanger 118 are set, and the oxygenator 116, heat exchanger 118, and gas mixer 120 are operated to optimize the temperature and gas composition of the perfusate for the initial stage of perfusion of a brain. As previously discussed, the heat exchanger 118 and gas mixer 120 are controlled based on signals generated by one or more sensor probes 128 in the sensor block 124. For example, the heat exchanger 118 is controlled to adjust the temperature of the perfusate to be within a predetermined range of temperature based on the temperature signals received from the sensor block 124. In addition, the gas mixer 120 is controlled to adjust the amount of oxygen, nitrogen, and/or carbon dioxide in the perfusate within the oxygenator 116 based on one or more signals generated by the sensor block 124 indicating the dissolved oxygen concentration of the perfusate within the sensor block 124, the dissolved nitrogen concentration of the perfusate within the sensor block 124, and the dissolved carbon dioxide concentration of the perfusate within the sensor block 124. In some implementations, the gas mixer 120 is configured to adjust the amount of oxygen, nitrogen, and/or carbon dioxide in the perfusate to be within a predetermined range, as detected by one or more sensor probes 128 in the sensor block.

Once the system 100 is flooded with perfusate and the temperature and gas composition of the perfusate have been adjusted to the correct initial settings, the system 100 enters a "zero flow stage" in which the pumps 114, 190, 111 are controlled to stop pumping the perfusate system 100 and the resistance valve 152 along the organ line 144 is closed for a predetermined amount of time. In some implementations, the system is controlled to be in the zero-flow stage for approximately 5 minutes. While the system is in the zero-flow stage, there is no flow through the flow sensors 130, 142 along the arterial circuit 106 and the flow sensors 130, 142 are calibrated.

Once the flow sensors 130, 142 along the arterial circuit 106 have been calibrated, the pumps 114, 190, 111 are controlled to resume pumping perfusate through the system 100 and the pulse generation system 1302 is controlled to achieve a target pressure and flow rate along the organ line 144, as described in detail above. While the pumps 114, 190, 111 and the pulse generator 136 are operated, initial measurements of one or more characteristics of perfusate can be performed before attaching the brain 110 to the system 100 in order to determine one or more baseline characteristics of the perfusate. These initial readings can include Raman spectroscopy analysis data generated by performing Raman spectroscopy on the perfusate using the Raman spectroscopy system 107, as described herein. In some implementations, samples of the perfusate 302, 304 are collected using one or more of the stopcocks 127, 132, 135, 153, 154, 155, 181, 182, 1912, and the samples of the perfusate 302, 304 can be tested manually to determine one or more characteristics of the perfusate. In some implementations, the stopcocks 127, 132, 135, 153, 154, 155, 181, 182, 1912 are manually operated by a user of the system 100 to collect perfusate samples. The initial readings of the perfusate can also include measurements performed by the sensor probes 128 of the sensor block 124.

Once the initial measurements of the perfusate characteristics have been performed, the system 100 is controlled to drain the perfusate from the brain housing 102. In order to drain the brain housing 102, the solenoid valve 177 along the Raman sample line 123 upstream of the waste container 145 is closed and the solenoid valve 147 along the drain line 143 is open to direct perfusate inside the brain housing 102 along the housing outlet line 176 and the Raman sample line 123 into the waste container 145. The waste scale 157 measures the weight of perfusate inside the waste container 145 in real-time as the brain housing 102 is drained. In response to the waste scale 157 detecting that a predetermined amount of perfusate has been provided to the waste container 145 from the brain housing 102 corresponding to the volume of the brain housing 102, the solenoid valve 177 along the Raman sample line 123 upstream of the waste container 145 is opened and the solenoid valve 147 along the drain line 143 is closed. Once the brain housing 102 is drained of perfusate, the brain housing scale is zeroed out to calibrate the brain housing scale 174. Once the brain housing 102 is drained and the brain housing scale 174 is calibrated, the flow pump 114 and pulse generator 136 are controlled to pulse perfusate along the organ line 144 to provide a small amount of perfusate to the brain housing 102 prior to connecting the brain 110 to the system.

The brain 110 is then positioned in the brain housing 102 and fluidly coupled to the system 100 using the brain interface 170. Prior to placing the brain 110 in the brain housing 102, each of the carotid arteries of the brain 110 is sutured to a respective fluid outlet of the brain interface 170. Once the carotid arteries of the brain 110 are sutured to the fluid outlets of the brain interface 170, the inlet line of the brain interface 170 is coupled to the organ line 144, and the brain 110 and the brain interface 170 are enclosed in the brain housing 102.

Once the brain 110 is positioned in the brain housing 102 and fluidly coupled to the arterial circuit 106 through the brain interface 170, the flow pump 114 is controlled to flow perfusate through the oxygenator 116 to the pulse generator 136, and the air supply system 138 and the pulse generator 136 are controlled to pump perfusate to the sensor block 124 and to provide pulsatile flow of perfusate to the brain 110 along the organ line 144.

Perfusate flows out of the oxygenator 116 along the arterial fluid line 112 to the pulse generator 136. As previously described, due to the relative positioning of the pulse generator 136, the brain housing 102, and the sensor block 124, and the structure of the pulse generator 136, all of the perfusate provided to the pulse generator 136 from the arterial fluid line 112 passively flows through the sensor block inlet line 146 when the diaphragm 214 of the pulse generator 136 is in an unflexed ("neutral") position. As perfusate passes through the sensor block 124, sensor probes 128 of the sensor block 124 measure one or more characteristic of the fresh perfusate inside the housing 126, including, but not limited to, pH, dissolved oxygen concentration, dissolved nitrogen concentration, dissolved carbon dioxide concentration, viscosity, and temperature. Based on the characteristics measured by the sensor probes 128, the oxygenator 116, heat exchanger 118, and gas mixer 120 are controlled in order to optimize the temperature, $O_2$ level, and gas composition of the perfusate.

As previously discussed, the heat exchanger 118 is configured to adjust the temperature of the perfusate flowing through the heat exchanger 118 based on the temperature of the perfusate detected by the sensor block 124. At the beginning of a perfusion procedure, the temperature of the perfusate is gradually increased by the heat exchanger 118 until a target temperature for the perfusate is reached, as detected based on the sensor probes 128 in the sensor block 124. In some implementations, the temperature of the perfusate is increased at a rate of 0.1° C./minute until a target temperature of the perfusate is reached, as detected by the sensor probes 128 of the sensor block 124. In some implementations, the target temperature is 36° C., and the heat exchanger 118 is controlled to increase the temperature of the perfusate from is 20° C. to is 36° C. over the course of a three hour period.

In addition, at the beginning of a perfusion procedure, the $O_2$ concentration of the perfusate is gradually increased by the gas mixer 120 until a target partial pressure of $O_2$ in the perfusate ($pO_2$) is reached, as detected based on the sensor probes 128 in the sensor block 124. In some implementations, the target partial pressure of $O_2$ in the perfusate is 450 mmHg. For example, at the beginning of the perfusion process, the partial pressure of $O_2$ in the perfusate is 200 mmHg and, based on data generated by the sensor probes 128, the gas mixer 120 and oxygenator 116 are controlled to gradually increase the concentration of the $O_2$ in the perfusate until the partial pressure of $O_2$ in the perfusate is 450 mmHg. In some implementations, the $O_2$ concentration for the perfusate is increased at a rate of 1% increase in $pO_2$ every thirty minutes for the first 12 hours of perfusions and increases to a rate of 2% increase in $pO_2$ every thirty minutes until the end of the perfusion process. By gradually increasing the temperature and the $O_2$ concentration of the perfusate provided to the brain 110 at the beginning of the perfusion procedure, the internal resistance of the brain 110 is decreased, which results in improved perfusion of the brain 110 with reduced risk of injury to the brain 110.

While the temperature and $O_2$ concentration of the perfusate are being ramped up by the heat exchanger 118 and the gas mixer 120, the pulse generation system 1302 is simultaneously controlled to progressively increase the pressure of the perfusate provided to the brain 110 along the organ line 144 until a target flow rate of perfusate along the organ line 144 is reached. For example, as previously discussed, due to the relative positioning of the pulse generator 136, the brain housing 102, and the sensor block 124, and the structure of the pulse generator 136, none of the perfusate provided to the pulse generator 136 passively flows through the organ line 144 to the brain 110 when the diaphragm 214 of the pulse generator 136 is in an unflexed ("neutral") position. Therefore, in order to provide pulsatile flow of perfusate to the brain 110 along the organ line 144, the air supply system 138 is controlled to provide pulsatile, pressurized air streams to the pulse generator 136 in order to cause the diaphragm 214 of the pulse generator 136 to flex downwards towards the fluid chamber 236, which causes the diaphragm 214 to cover the openings 210 in the fluid chamber 236 of the pulse generator 136 and increase the pressure within the interior 212 of the pulse generator 136. As result of the increased pressure caused by the flexing of the diaphragm 214, at least a portion of the fresh perfusate contained within the interior 212 of the pulse generator is forced through the organ line outlet 208 of the pulse generator 136 and along the organ line 144 to the brain 110.

At the beginning of the perfusion procedure, the pulse generation system 1302 is controlled to provide pulsatile flow of perfusate to the brain 110 along the organ line 144 at an initial pressure, as measured by the second pressure sensor 141 along the organ line 144. For example, as previously discussed, the second electronic pressure regulator 166 is controlled based on pressure signals generated by second pressure sensor 141 along the organ line to adjust the frequency and duration which the second electronic pressure regulator 166 provides pressurized air to the pulse generator 136 in order to adjust amplitude and/or base of the pulsatile flow of perfusate to the brain 110 until the initial pressure threshold along the organ line 144 is reached, as detected by the second pressure sensor 141. In some implementation, the initial pressure threshold along the organ line is 16 mmHg.

Once the initial pressure threshold along the organ line 144 has been maintained for a predetermined period, as determined based on the signals generated by the pressure sensor 141 along the organ line 144, the second electronic pressure regulator 166 is controlled to cause the pulse generator 136 to progressively increase the pulsatile flow along the organ line 144 until a particular target flow rate along the organ line 144 is detected by the flow sensor 142 along the organ line 144. In some implementations, the pulse generation system 1302 is controlled based on signals received from the pressure sensor 141 to increase the pressure along the organ line 144 at a rate of 0.0333 mmHg/minute. In some implementations, the pulse generation system 1302 is configured to increase the pressure in the organ line 144 from 16 mmHg to 20 mmHg, increasing the pressure along the organ line at a rate of 1 mmHg every 30 minutes. In some implementations, the pulse generation system 1302 in controlled to maintain a constant amplitude of pressure along the organ line 144. In some implementations, the pulse generation system 1302 in controlled to maintain a constant amplitude of 10 mmHg along the organ line 144.

Once the target flow rate is detected by the flow sensor 142, the pulse generation system 1302 is controlled based on signals generated by the flow sensor 142 in order to provide pulsatile flow along the organ line 144 sufficient to maintain the predetermined flow rate along the organ line 144 as detected by the flow sensor 142, while maintaining the pressure along the organ line 144 (as detected by pressure sensor 141) within a predetermined range of pressure. In some implementations, the target flow rate is 10 mL/minute. By gradually increasing the pressure and the flow rate of the perfusate provided to the brain 110, the internal resistance of the brain 110 is correspondingly gradually reduced, which enables the vasculature of the brain 110 to more effectively receive the perfusate while minimizing injury or other damage to the brain 110.

Perfusate flowing along the organ line 144 is provided to the brain 110 and perfuses the entire vasculature of the brain 110, including the penetrating arterioles, pre-capillary arterioles, and capillaries of the brain 110. After flowing through the vasculature of the brain 110, the used perfusate is collected in the basin 1022 of the brain housing 102 and exits the brain housing 102 along the housing outlet line 176.

As previously discussed, at the beginning of the perfusion of the brain 110, an initial "flush" of the brain 110 in order to removed toxins and other unwanted chemical compounds that have built up in the brain 110 during the post-mortem period prior to perfusion During the initial flush of the brain 110, the solenoid valve 177 along the Raman sample line 123 upstream of the waste container 145 is closed and the solenoid valve 147 along the drain line 143 is open to direct used perfusate flowing out of the brain 110 to the waste container 145. Once the waste scale 157 detects that a predetermined amount of used perfusate has been provided to the waste container 145 during the initial flush, the solenoid valve 177 along the Raman sample line 123 upstream of the waste container 145 and the solenoid valve 178 along the housing outlet line 176 between the brain housing 102 and the perfusate reservoir 104 are each controlled to open and the solenoid valve 147 along the drain line 143 is controlled to close, which directs used perfusate flowing along the housing outlet line 176 and the Raman sample line 123 back to the perfusate reservoir 104. In some implementations, the brain 110 is initially flushed with 500 mL of perfusate.

Once the initial flush of the brain 110 is complete and the solenoid valve 147 along the drain line 143 is closed, the perfusion system 100 is a closed-loop system and the brain 110 is perfused with perfusate from the perfusate reservoir 104 throughout the duration of the perfusion procedure. As the brain 110 is being perfused, the dialysis filtration system 109 can be operated to remove metabolic waste products or other unwanted substances from the perfusate, as previously described herein. In some implementations, the brain 110 is perfused using the perfusion system 100 for 24 hours or longer (e.g., 24-48, 48-72 hours, 48-96 hours, 96 hours or longer).

During the perfusion process, the automatic sampler system 105 is controlled to collect samples of the fresh perfusate 302 in the arterial circuit 106 and the used perfusate in the venous circuit 108 at predetermined intervals. For example, the automatic sampler system 105 can be controlled to collect samples of fresh perfusate 302 from the perfusate reservoir 104 and used perfusate from the brain housing 102 at the start of a perfusion process ("0 hour"), 6 hours after the start of a perfusion process, 12 hours after the start of a perfusion process, and 24 hours after the start of a perfusion process. In order to collect a sample of fresh perfusate from the arterial circuit 106, the solenoid valve 151 along the arterial sample line 150 between the sensor block 124 and the perfusate reservoir 104 is closed, the solenoid valve 171 along the arterial sample line 150 between the sensor block 124 and the automatic sampler system 105 is opened, and the pump 184 of the automatic sampler system 105 is operated to draw perfusate out of the sensor block 124 along the arterial sample line 150, and the solenoid manifold 185 is controlled to direct the perfusate through the sample collection line 186 and into a sample collection vessel. In order to collect samples of the used perfusate 304 from the venous circuit 108, the solenoid valve 173 along the venous sample line 183 is opened, and the pump 184 of the automatic sampler system 105 is operated to draw perfusate out of the brain housing 102 along the venous sample line 183, and the solenoid manifold 185 is controlled to direct the perfusate through the sample collection line 186 and into a sample collection vessel.

During the perfusion process, the syringe pump manifold 167 is controlled to introduce one or more pharmaceutical compounds into the perfusate reservoir 104, which are then provided to the brain 110 through the perfusate. The syringe pump manifold 167 is operated in conjunction with the dialysis filtration system 109 to introduce the pharmaceutical compound to the brain 110 in accordance with a particular predetermined release profile. For example, as previously described, the Raman spectroscopy system 107 can be used to determine the concentration of the pharmaceutical compound in the perfusate contained in the perfusate reservoir 104 in real-time throughout the perfusion procedure. Based on the concentration of the pharmaceutical compound in the fresh perfusate detected by the Raman spectroscopy system 107, the syringe pump manifold 167 can be controlled to increase, decrease, or maintain the rate the pharmaceutical compound is provided to the perfusate reservoir 104 in order to align the concentration of the pharmaceutical compound with the desired release profile. In addition, based on the concentration of the pharmaceutical compound detected in the fresh perfusate by the Raman spectroscopy system 107, the dialysis pump 190 can be controlled to pump perfusate from the perfusate reservoir 104 along the dialyzer inlet line 192 into the dialyzer 191, which removes at least a portion of the pharmaceutical compound from the perfusate. The perfusate with a reduced concentration of the pharmaceutical compound exits the dialyzer 191 is pumped back to the perfusate reservoir 104 along the dialyzer outlet line 193.

In addition, the Raman spectroscopy system 107 is controlled to perform Raman spectroscopy on the fresh perfusate in the perfusate reservoir 104 and on the used perfusate flowing out of the brain housing 102 at predetermined intervals throughout the perfusion process in order to determine one or more characteristics of the fresh perfusate and used perfusate in real-time throughout the perfusion process. As discussed above, the data generated by the Raman spectroscopy system 107 can be used to control the syringe pump manifold 167 and the dialysis filtration system 109 to produce a particular release profile of a pharmaceutical compound. In addition, the data generated by the Raman spectroscopy system 107 can be used to determine metabolic activity of the brain 110 and the health of the brain 110 in real-time during the perfusion process. For example, as previously discussed, the chemical composition of the fresh perfusate in the perfusate reservoir 104 and the chemical composition of the used perfusate flowing out of the brain 110 can each be determined using the spectroscopy system 107, and various metabolic processes performed by the brain 110 during perfusion can be determined based on any differences in chemical composition in the fresh perfusate and used perfusate. In addition, while a pharmaceutical compound is being provided to the brain 110 through the perfusate, the Raman spectroscopy system 107 is controlled to perform Raman spectroscopy on samples of the used perfusate 304 flowing out of the brain 110 in order to determine whether the pharmaceutical compound has crossed the blood-brain barrier of the brain 110, the reaction of the brain 110 to the pharmaceutical compound, the likely efficacy of the pharmaceutical compound on treating the targeted disease, and potential side effects that may result from the pharmaceutical compound.

The Raman spectroscopy probe 172 is controlled to perform Raman spectroscopy on the tissue of the brain 110 in real-time during the perfusion procedure. As previously discussed, the Raman spectroscopy data generated by the Raman spectroscopy probe 172 can be used to determine the effectiveness of the perfusion process, as well as predict the length the of time the brain 110 can be effectively perfused, for example, before the brain 110 undergoes significant swelling. In addition, the Raman spectroscopy probe 172 is controlled to perform Raman spectroscopy on the tissue of the brain 110 while a pharmaceutical compound is being provided to the brain 110 through the perfusate in order to determine whether the pharmaceutical compound has crossed the blood-brain barrier and to determine the effect of a pharmaceutical compound on the brain 110.

The Raman spectroscopy data generated by the Raman spectroscopy system 107 and the Raman spectroscopy probe 172 is stored in a database. In some implementations, the Raman spectroscopy data generated by the Raman spectroscopy system 107 and the Raman spectroscopy probe 172 is provided to the trained machine learning model to predict, e.g., a metabolic pathway of the pharmaceutical compound in the brain, an activation or deactivation of certain gene pathways in the brain, physiological changes to the brain (e.g., swelling, tissue damage, infection, etc.), relating to the administration of the pharmaceutical compound.

Once the perfusion process is complete, for example, because the predetermined length of perfusion has elapsed, the pumps 111, 114, 190, 1002, 1906 are each controlled to stop pumping the perfusate through the system 100, the brain 110 is removed from the brain housing 102, and the perfusate contained within the perfusate reservoir 104 and the brain housing 102 is disposed of in a waste container or directly to a drain. The fluid lines 112, 123, 131, 144, 143, 146, 148, 150, 156, 176, 183, 192, 193, 197, 179, 1908 of the arterial circuit 106, the venous circuit 108, the in-line Raman spectroscopy system 107, and the dialysis filtration system 109 are disconnected from respective components of the system 100 and are replaced with new fluid lines prior to the start of another perfusion procedure.

Figure 9:
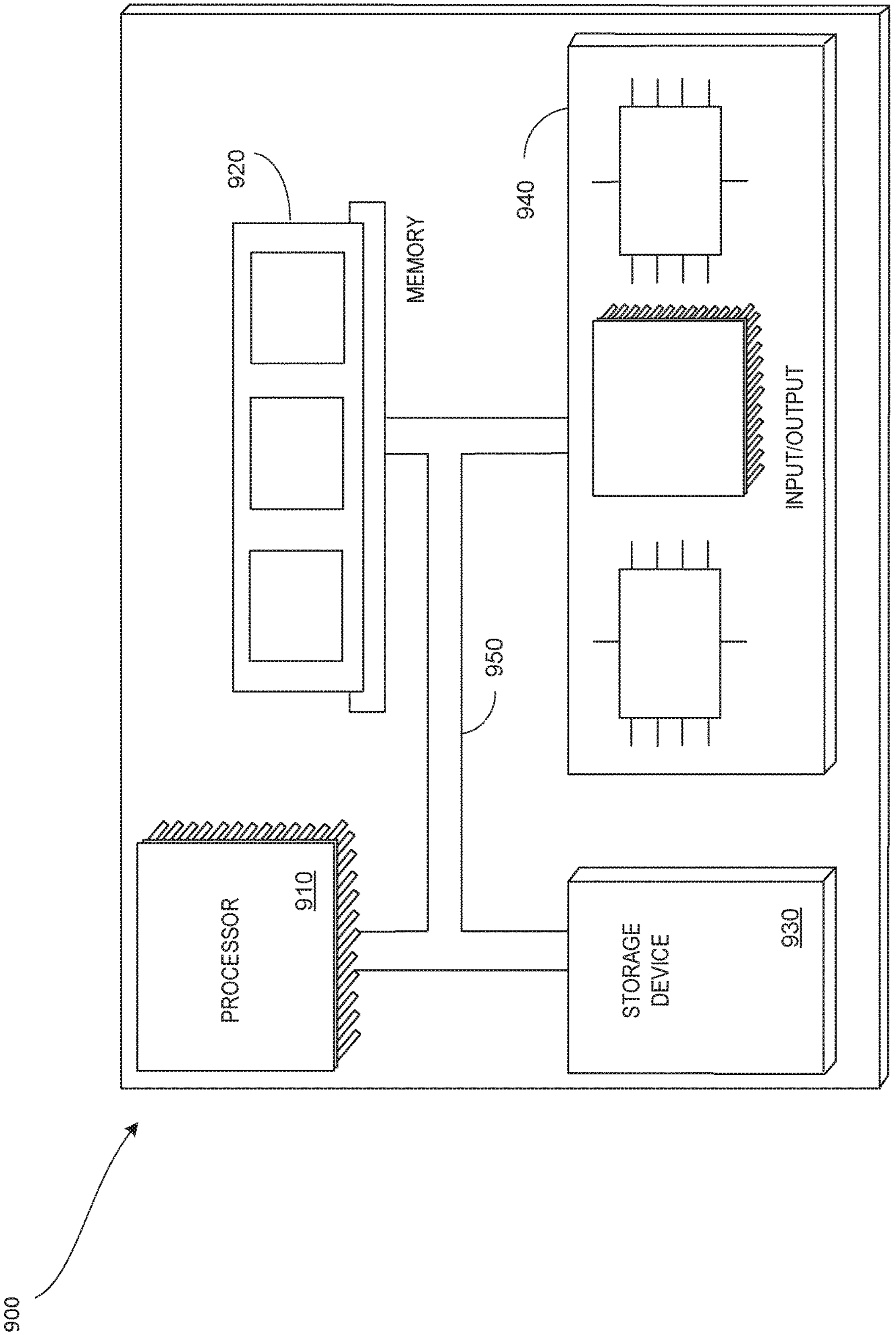
FIG. 9 is a block diagram of an example computer system by which a computer system of the perfusion system of FIG. 1 can be implemented.

FIG. 9 is a block diagram of an example computer system 900. For example, referring to FIG. 1, the computer system 188 of the perfusate system 100 could be an example of the system 900 described here. The system 900 includes a processor 910, a memory 920, a storage device 930, and an input/output interface 940. Each of the components 910, 920, 930, and 940 can be interconnected, for example, using a system bus 950. The processor 910 is capable of processing instructions for execution within the system 900. The processor 910 can be a single-threaded processor, a multithreaded processor, or a quantum computer. The processor 910 is capable of processing instructions stored in the memory 920 or on the storage device 930. The processor 910 may execute operations such as receiving signals from one or more sensors (e.g., the pressure sensors 140, 141, 164, 168, 195, 1008, the flow sensors 130, 142, and the temperature sensors 113, 121 shown in FIG. 1) and controlling or more elements of the system (e.g.,. the solenoid valves 129, 133, 139, 147, 149, 151, 158, 159, 171, 173, 177, 178 of FIG. 1) based on the received signals.

The memory 920 stores information within the system 900. In some implementations, the memory 920 is a computer-readable medium. The memory 920 can, for example, be a volatile memory unit or a non-volatile memory unit. In some implementations, the memory 920 stores a data structure. In some implementations, multiple data structures are used.

The storage device 930 is capable of providing mass storage for the system 900. In some implementations, the storage device 930 is a non-transitory computer-readable medium. The storage device 930 can include, for example, a hard disk device, an optical disk device, a solid-date drive, a flash drive, magnetic tape, or some other large capacity storage device. The storage device 930 may alternatively be a cloud storage device, e.g., a logical storage device including multiple physical storage devices distributed on a network and accessed using a network.

The input/output interface 940 provides input/output operations for the system 900. In some implementations, the input/output interface 940 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (e.g., display device 189 of FIG. 1). In some implementations, mobile computing devices, mobile communication devices, and other devices are used.

In some implementations, the system 900 is a microcontroller. A microcontroller is a device that contains multiple elements of a computer system in a single electronics package. For example, the single electronics package could contain the processor 910, the memory 920, the storage device 930, and input/output interfaces 940.

Although an example processing system has been described in FIG. 9, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the disclosure.

For example, while the perfusate system 100 has been described as including both a filter bag 101 inside the perfusate reservoir 104 and an in-line mechanical filtration system 1001 has been described as including a filter bag 101, in some implementations, the perfusate system 100 includes only the filter bag 101 inside the perfusate the reservoir 104 to filter the perfusate entering the reservoir 104 without the in-line mechanical filtration system 1001. In other implementations, the perfusate system 100 includes only the in-line mechanical filtration system 1001 to filter the perfusate entering the reservoir 104 without the filter bag 101 inside the perfusate the reservoir 104.

In addition, while the pumps 111, 114, 190, 1002, 1906 have been described as being peristaltic pumps, in some implementations, other types of pumps can be used. In some implementations, one or more of the pumps 111, 114, 190, 1002, 1906 are roller pumps or centrifugal pumps.

While the brain interface 170 has been described as including two fluid outlets with each of the carotid arteries of the brain 110 being sutured to a respective fluid outlet of the brain interface 170, in some implementations, the brain interface 170 includes other numbers of fluid outlets (e.g., 1, 3, 4, etc.). For example, the brain interface 170 can include a single fluid outlet and a single carotid artery of the brain 110 can be coupled to the fluid outlet of the brain interface 170.

In addition, while the brain interface 170 has been described as including two fluid inlets, in some implementations, the brain interface 170 includes a single fluid inlet that can be coupled to the organ line 144 and that is fluidly coupled to the two fluid outlets of the brain interface 170.

Further, in some implementations, the brain 110 is fluidly coupled to the organ line 144 without the use of a brain interface 170. For example, in some implementations, samples of pig vasculature are sutured to the carotid arteries and basilar artery of the human brain 110 at a first end and are fluidically connected to the organ line (e.g., through suturing) at a second end. Perfusate flowing through the organ line 144 flows through the pig vasculature sutured to the brain 110, through the carotid and basilar arteries of the brain 110, and perfuses the brain 110.

While the level sensors 125, 180 have been described as being infrared level sensor, other types of level sensors can be used to detect the level of perfusate in the sensor block 124 and the brain housing 102, respectively. For example, the level sensors 125, 180 are ultrasonic sensors, capacitance sensors, or other types of optical sensors.

While the sensor block inlet line 146 has been described as a y-splitter line with a single line flowing out of the pulse generator 136 that splits into two fluid lines flowing into the sensor block 124, in other implementations, the sensor block inlet line can be a single, unsplit line.

While the dialysis filtration system 109 has been described as filtering the perfusate without the use of an exchange solution, in some implementations, the dialysis filtration system 109 includes a source of exchange solution and the perfusate is filtered using the exchange solution. For example, in some implementations, the dialyzer 191 is a capillary dialyzer, and perfusate and exchange solution are pumped through the dialyzer 191 at the same time. The exchange solution flowing through the dialyzer 191 interacts with the perfusate flowing through the dialyzer 191 to remove waste products from the perfusate and add nutrients to the perfusate. For example, while the perfusate flows within porous microtubes of the dialyzer 191, the exchange solution can flow outside the porous microtubes such that waste products pass from the perfusate in the interior of the porous microtubes to the exchange solution surrounding the porous microtubes and such that nutrients pass from the exchange solution surrounding the porous microtubes into the persuade inside the microtubes. The filtered perfusate exits the dialyzer 191 and flows back to the perfusate reservoir 104 along the dialyzer outlet line 193, while the exchange solution exits the dialyzer 191 and flows to the waste fluid receptacle 198 via the spent exchange solution line 197. In some embodiments, the exchange solution is replaced or replenished over time to prevent the depletion of nutrients or the accumulation of toxins.

While the perfusion system 100 has been described as including a syringe pump manifold 167 with two or more syringes filled with a pharmaceutical compound, in some implementations, the perfusion system 100 includes a single syringe pump with a single syringe filled with a pharmaceutical compound.

While the lid 218, the central housing 202, and the base 220 of the pulse generator 136 have been described as being attached to one another using a set of bolts 224 and nuts 228, other types of mechanical fasteners can be used to couple the lid 218, central housing 202, and base 220. For example, in some implementations, the lid 218, the central housing 202, and the base 220 are attached to one another using one or more of bolts, rivets, pins, or adhesive.

While the drain line 143 of the perfusate system 100 has been described as being coupled to a waste container 145 to collect the perfusate drained from the system 100 along the drain line 143, in some implementations, the drain line 143 is directly coupled a drain and perfusate flowing along the drain line 143 is directed into the drain coupled to the drain line 143.

While the stopcocks 127, 132, 135, 153, 154, 155, 181, 182 of the system have been described as being manually operated by a user of the system 100 to collect perfusate samples, in some implementations, one or more of the stopcocks 127, 132, 135, 153, 154, 155, 181, 182, 1912 can be automatically controlled to collect samples of the perfusate. For example, one or more of the stopcocks 127, 132, 135, 153, 154, 155, 181, 182, 1912 can be automatically controlled to collect a sample of perfusate from the system 100 at one or more particular points during the perfusion process. For example, one or more of the stopcocks 127, 132, 135, 153, 154, 155, 181, 182 can be fluidly coupled to an autosampler or a sensor (e.g., pressure sensor) in order to automatically collect fluid sample or other data using the respective stopcocks 127, 132, 135, 153, 154, 155, 181, 182. In addition, the stopcocks 127, 132, 135, 153, 154, 155, 181, 182 have previously been described as automatically being controlled using servo-motor to control and change flow paths throughout the system 100. However, in some implementations, an operator can manually operate one or more of the stopcocks 127, 132, 135, 153, 154, 155, 181, 182 to alter the flow paths of the system.

While the computer system 188 has been depicted as including a single computing device, in some implementations, the computing system 188 includes multiple computing devices or processors (2, 3, 4, etc.) in communication with the various electronic components of the perfusion system 100 and configured to control operation of one or more electronic components of the perfusion system 100. Each of the computing devices of the computer system 188 may be in wired or wireless communication with one or more electronic components of the perfusion system 100. In addition, one or more of the computing devices of the computer system 188 can be a remote computing device that is located at a different, remote location from the perfusion system 188.

In addition, while the process of performing an initial flush of the brain 110 using the perfusate system 100 has been described as being stopped automatically in response to the waste scale 157 detecting that a threshold weight of perfusate has been received by the waste container 145, in some implementations, the initial flush procedure is manually stopped by a user. For example, in some implementations, the waste container 145 includes one or more markings indicating the volume of fluid inside the waste container 145, and as perfusate flows along the drain line 143 into the waste container 145, an operator of the system 100 monitors the volume of perfusate collected by the waste container 145. In response to the operator observing that the waste container 145 has received a threshold volume of perfusate, the operator closes the solenoid valve 147 along the drain line 143 and opens the solenoid valve 177 along the along the Raman sample line 123. In some implementations, the operator adjusts the solenoid valves 147, 177 to stop the initial flush of the brain 110 in response to observing that 500 mL of perfusate has been collected in the waste container 145. In some implementations, the operator of the system 100 adjusts the solenoid valves 147, 177 to stop the initial flush of the brain 110 based on a predetermined amount of time elapsing since the start of the initial flush procedure. In some implementations, for example, an operator of the system 100 manually stops the initial flush procedure 30 minutes to 1 hour after starting the flush procedure.

While the syringe pump manifold 167 and the dialysis filtration system 109 have been described as being controlled in order to provide concentrations of a drug according to a predetermined release profile, in some implementations, the uptake and metabolism of a particular drug is tracked in real time using the Raman spectroscopy system 107 and/or the Raman spectroscopy probe 172, as described above, and the syringe pump manifold 167 and dialysis filtration system 109 are dynamically controlled to increase or decrease the concentration of the drug in the perfusate based on the brain's uptake and metabolism of the drug, as detected using the Raman spectroscopy system 107 and/or the Raman spectroscopy probe 172. By dynamically adjusting the concentration of the drug in the perfusate using the syringe pump manifold 167 and the dialysis filtration system 109 in response to real-time Raman spectroscopy data indicating the uptake and metabolism of the drug by the brain, an optimized release profile for the drug that provides increased uptake and optimized metabolism of the drug by the brain can be determined.

While the perfusion system 100 has been described as having both an in-line Raman spectroscopy system 107 for performing Raman spectroscopy on perfusate and a Raman spectroscopy probe 172 for performing Raman spectroscopy on the tissue of the brain 110 in the brain housing 102, in some implementations, the perfusion system 100 does not include the Raman spectroscopy probe 172. In such implementations, the uptake and metabolism of drugs and other components of the perfusate by the brain 110 can be determined based on performing Raman spectroscopy of the used perfusate exiting the brain using the Raman spectroscopy system 107 alone.

While the spectroscopy system 107 and the spectroscopy probe 172 of the perfusion system 100 have been described as being configured to perform Raman spectroscopy, it should be understood that such spectroscopy can include surface-enhance Raman spectroscopy (SERS). In addition, while the spectroscopy system 107 and the spectroscopy probe 172 of the perfusion system 100 have been described as being configured to perform Raman spectroscopy, in some implementations, the spectroscopy system 107 and spectroscopy probe 172 can be configured to other types of spectroscopy. For example, one or both of the spectroscopy system 107 and the spectroscopy probe 172 can be configured to perform fluorescence spectroscopy, UV spectroscopy, or infrared spectroscopy.

Further, as an alternative to or in additional to using spectroscopy of the type described above, the perfusion systems described herein can use transcriptomics (including but not limited to qPCR, RNAseq, scRNAseq, snRNAseq, RNAscope, etc), proteomics, mass spectrometry, ELISA, histology, genotyping, etc. to analyze the perfusion fluid and/or brain tissue samples.

In addition, referring to FIG. 3, while the cellular and metabolic activity of the brain have been described as being determined based on performing Raman spectroscopy using the Raman spectroscopy system and/or the Raman spectroscopy probe 172, in some implementations, tissue samples 406 of the brain 110 and/or samples of the perfusate exiting the brain 110 are alternatively or additionally collected during and/or after perfusion of the brain 110 by the system 100, and one or more tests or assays are performed on the collected brain tissue samples 406 and/or collected perfusate samples to determine cellular and metabolic activity of the brain 110 during the perfusion procedures. Various testing procedures can be performed on the collected brain tissue samples 406 and the collected perfusate samples including, but limited to, spectroscopy, gene sequencing, cytokine analysis, anti-body analysis, genomic analysis, transcriptomic analysis, proteomic analysis, metabolomic analysis.

While the perfusion system 100 has been described as being used to determine the uptake and efficacy of a pharmaceutical compound, the perfusion system 100 can similarly be used to determine the uptake and efficacy of any of various other therapeutic agents, including, but not limited to, antibodies, biologics, viral vectors, lipid nanoparticles, peptides, etc.

In some examples, a particular gene therapy for treating a particular disease can be tested using the perfusion system 100. For example, a single vector or a collection of vectors carrying respective DNA segments can be added to the perfusate in the perfusate reservoir using similar procedures described herein for introducing a pharmaceutical compound to the perfusate, and the brain 110 can be perfused with the perfusate containing the vector(s). The used perfusate exiting the brain and the brain tissue can be tested using techniques described herein to determine whether the vector(s) have crossed the blood-brain barrier of the brain 110, to determine the vector transcytosis rates through the blood-brain barrier, and to determine an optimized release profile for the vector(s) to be most effectively taken up by the brain 110.

Figure 16:
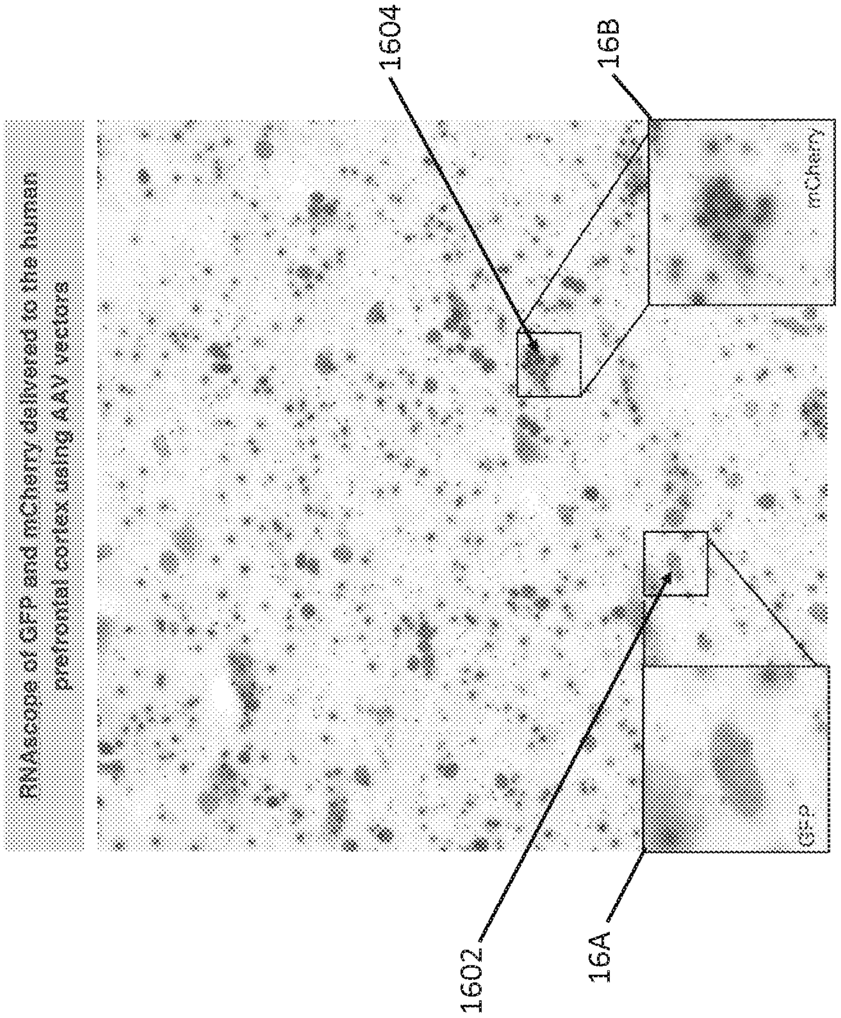
FIG. 16 is an RNAScope image showing GFP and mCherry expressed in the frontal cortex of a brain.

FIG. 16 is an RNAScope image showing that GFP and mCherry were successfully delivered to the frontal cortex of the brain using viral vectors, namely adeno-associated virus (AAV). Box 16A in FIG. 16 is an enlarged view of region 1602 showing evidence of GFP, while box 16B is an enlarged view of region 1604 showing evidence of mCherry. In this example, rather than introducing a chemical compound into the perfusate of the perfusion system 100, the viral vectors carrying the GFP and mCherry are introduced into the perfusate. The presence of the GFP and mCherry in the frontal cortex indicates that the viral vectors used were able to cross the blood-brain barrier and reach the frontal cortex of the brain.

While methods of using the perfusion system 100 to test whether therapeutic agents can cross the blood-brain barrier, in some cases, the perfusion system 100 is alternatively or additionally used to determine whether the blood-brain barrier of a brain is intact. In such cases, for example, one or more agents known to be incapable of crossing the blood-brain barrier (e.g., certain large and/or water soluble molecules) can be introduced into the perfusate and then any of the various testing techniques described herein can be used to determine whether the agent or agents has/have crossed into the brain. The presence of any of those agents in the brain would be evidence that the blood-brain barrier of the brain is no longer intact. This may help researchers to determine whether test data related other therapeutic agents tested on that brain (particularly test data showing whether those therapeutic agents were able to cross the blood-brain barrier) are reliable.

Figure 7:
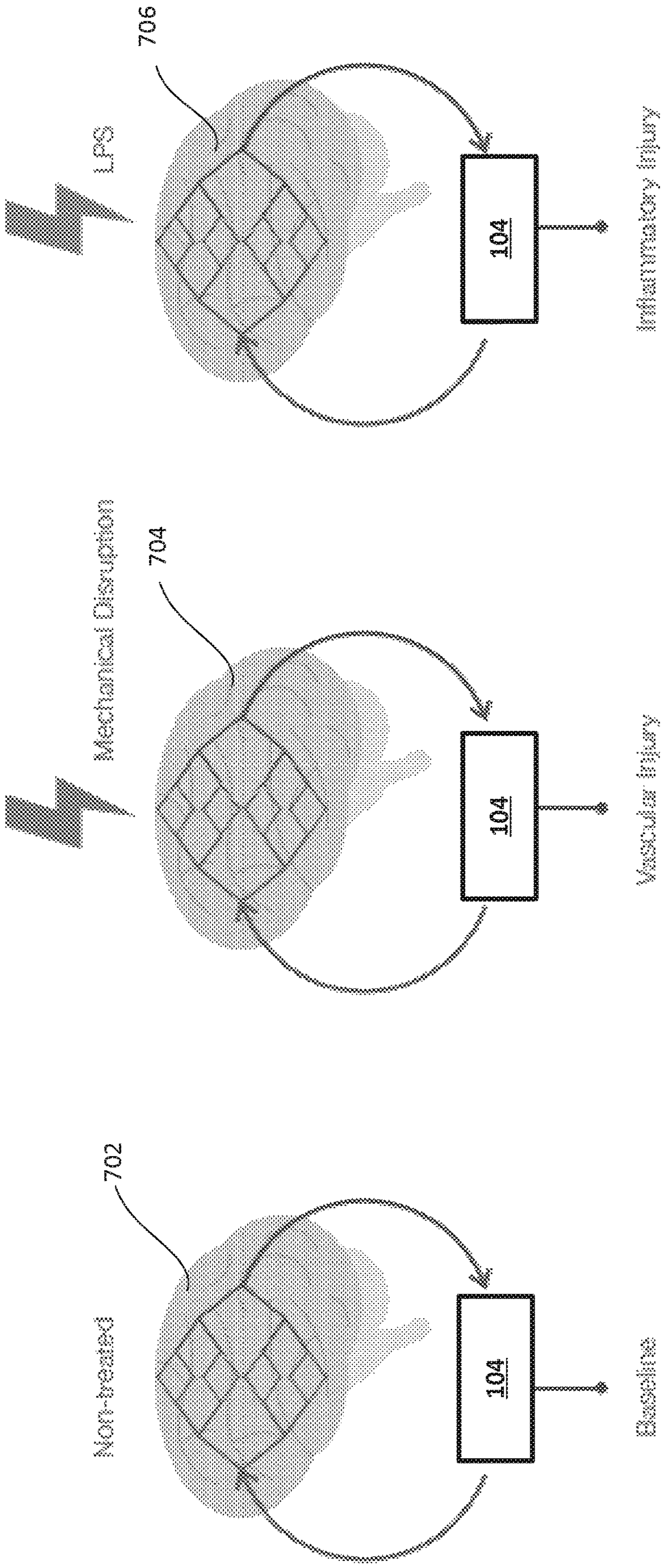
FIG. 7 depicts a schematic illustration of different mammalian brains perfused and tested using the system of FIG. 1.
Figure 8:
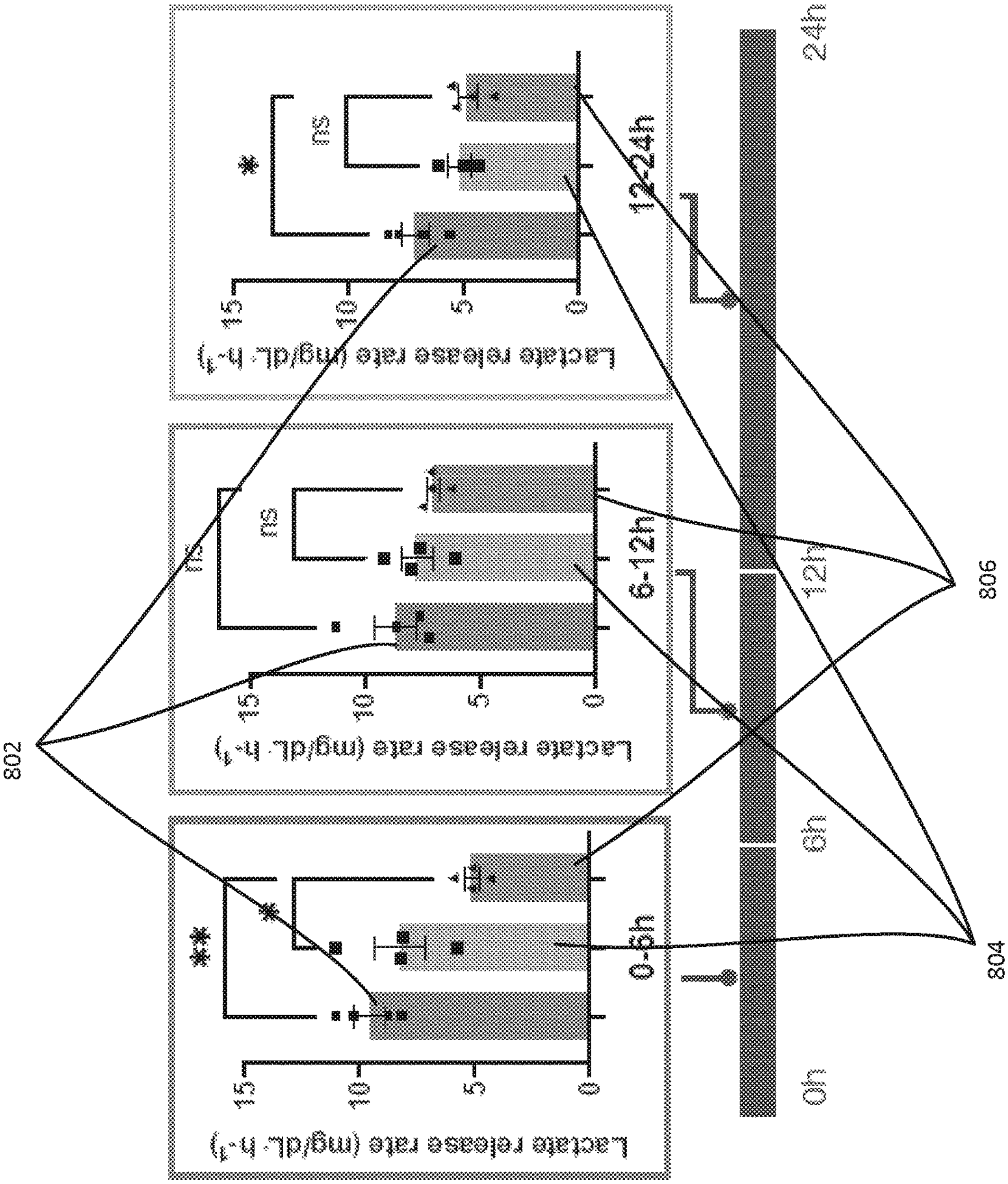
FIG. 8 depicts example rates of lactate released by the mammalian brains depicted in FIG. 7 during perfusion of the brains using the system of FIG. 1.

In addition, while the perfusion system 100 has been described as being used to perfuse and test brains that have not otherwise been mechanically or chemically altered, the perfusion system 100 can be used to perfuse and tests brains that have been mechanically or chemically altered (e.g., to simulate vascular and inflammatory injuries) prior to perfusing the brain with the system 100. For example, referring to FIGS. 7 and 8, an experiment was conducted in which three brains 702, 704, 706 were each perfused using the perfusion system 100 and the rate of lactate released by each of the brains 702, 704, 706 was monitored throughout the perfusion process. The first brain 702 ("baseline brain 702") was not mechanically or chemically altered prior to being perfused by the perfusion system 100. The second brain 704 was mechanically modified to mimic vascular disruptions prior to perfusion of the second brain 704 using the perfusion system 100, effectively replicating the impact of vascular injury on brain tissue. The third brain 706 was treated with lipopolysaccharide (LPS) during perfusion using the perfusion system 100 to mimic pathophysiological conditions associated with vascular impairments and inflammation in the brain. The rate of lactate release by each of the three brains 702, 704, 706 was tested throughout the 24 hour perfusion process (e.g., by performing Raman spectroscopy on the used perfusate exiting the brains 702, 704, 706 using the Raman spectroscopy system 107). As can be seen in FIG. 8, the rate of lactate release 802 for the untreated brain 702 was higher than both the rate of lactate release 804 for the mechanically altered brain 704 and the rate of lactate release 806 for the brain 706 perfused with lipopolysaccharide (LPS). By utilizing the perfusion system to perfuse and test brains that are mechanically or chemically altered to simulate vascular and inflammatory injuries, the perfusion system 100 can be used to effectively study mechanisms and potential treatments for brain injuries.

While the perfusate system 100 has been described as being used to perfuse a human brain 110, the perfusion system 100 can be used to perfuse other mammalian brains, such as pig brains. In some implementations, the perfusate used in the perfusate system 100 may be altered in order to more effectively perfuse non-human mammalian brains. In addition, an alternate brain housing 102 may be used to better accommodate and support a pig brain. For example, in some implementations, when the perfusion system 100 is being used to perfuse a pig brain, the brain housing 102 is replaced with a pig brain housing that is smaller than the brain housing 102 used to house the human brain 110.

FIGS. 11A-11D depict an example brain housing 1102 that can be used to support a pig brain during a perfusion process performed using the system 100 of FIG. 1. As can be seen in FIGS. 11A-11D, the brain housing 1102 includes a basin 1104 and lid 1106. The lid 1106 is configured to releasably couple to the basin 1104 and can be separated from the basin 1104 to allow a pig brain to be positioned inside the interior of the brain housing 1102.

Figure 11D:
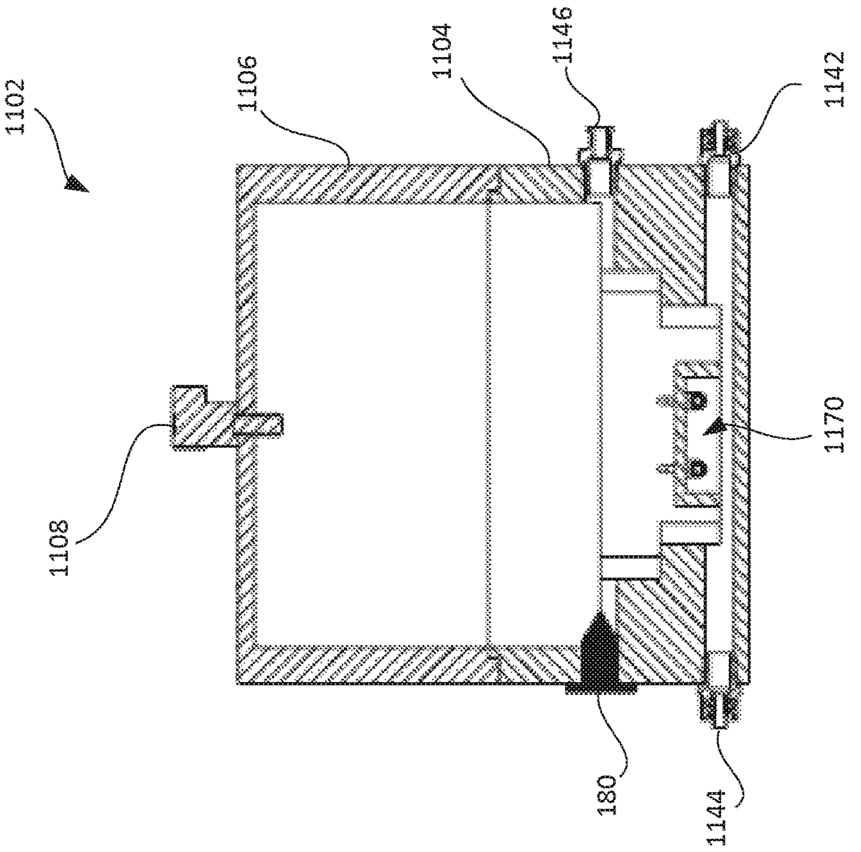
FIG. 11D is a cross-sectional view of the example brain housing of FIG. 11A.
Figure 11C:
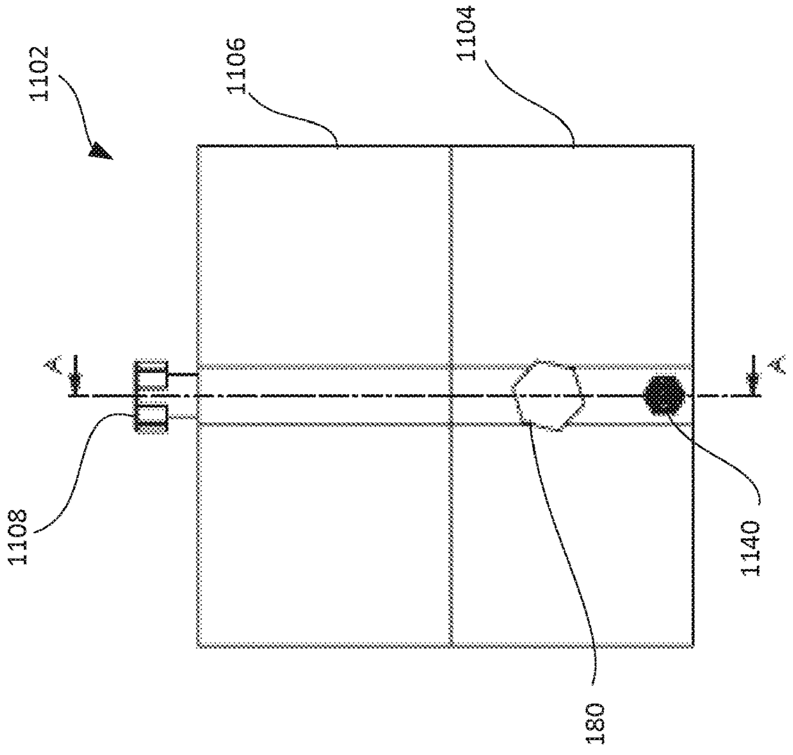
FIG. 11C is a side view of the example brain housing of FIG. 11A.

When the brain housing 1102 is fluidly connected to the system 100 of FIG. 1, the housing outlet line 176 extends from the brain housing 1102 and fluidly couples the brain housing 1102 to the perfusate reservoir 104. Referring to FIGS. 11A, 11B, and 11D, the brain housing 1102 includes a coupling 1142 connected to the side of the basin 1104. The coupling 1142 fluidly connects the interior of the basin 1104 of the brain chamber 1102 to the housing outlet line 176. In some implementations, the coupling 1142 is a quick-turn tube coupling. In some implementations, the brain housing 1102 includes a second coupling 1144 that can be coupled to the outlet line 176 or to another outlet line in order to increase the rate of drainage of fluid out of the brain housing 1102 to the perfusate reservoir 104.

The brain housing 1102 also includes a fluid coupling 1146 that fluidly connects the shunt line 156 to the interior of the brain chamber 1102. In some implementations, the coupling 1146 is a quick-turn tube coupling.

The brain housing 1102 also includes a three arm knob 1108 releasably coupled to the lid 1106 of the brain housing 1102. The knob 1108 serves as an ergonomic handle for opening the lid 1106 of the brain housing 1102.

The brain housing 1102 includes a level sensor 180 to detect the level of fluid (e.g., used perfusate) inside the basin 1104 of the brain housing 1102, and the solenoid valve 178 along the housing outlet line 176 is controlled to open or close based on signals generated by the level sensor 180. As depicted in FIG. 11D, the level sensor 180 is coupled to the basin 1104 of the brain chamber 1102. In some implementation, the level sensor 180 is coupled to the basin 1104 at the same or similar height along the basin 1104 as the fluid coupling 1146 that fluidly connects the shunt line 156 to the interior of the brain chamber 1102. In some implementations, the level sensor 180 is an optical level sensor, such as an infrared level sensor. For example, the solenoid valve 178 is controlled to remain in a closed state and prevent flow of used perfusate from the brain housing 1102 into the perfusate reservoir 104 until the level sensor 180 generates a signal indicating that the fluid level inside the brain housing 1102 has exceeded a threshold fluid level. In response to the level sensor 180 generating a signal indicating that the fluid level inside the brain housing 1102 has exceeded a threshold fluid level, the solenoid valve 178 is opened to allow used perfusate to flow from the brain housing 1102 along the housing outlet line 176 to the perfusate reservoir 104. Once the level sensor 180 detects that the fluid level inside the brain housing 1102 has fallen below the threshold level, the solenoid valve 178 is closed, which prevents fluid from flowing from the brain housing 1102 to the perfusate reservoir 104.

The brain housing 1102 is configured to maintain the pig brain under normothermic conditions. For example, when the basin 1104 and lid 1106 of the brain housing 1102 are securely coupled together, a warm, humid environment is maintained within the brain housing 1102. In some implementations, the brain housing 1102 includes temperature and humidity controls configured maintain a particular temperature and humidity level to prevent drying or other injury to the brain.

Figure 12A:
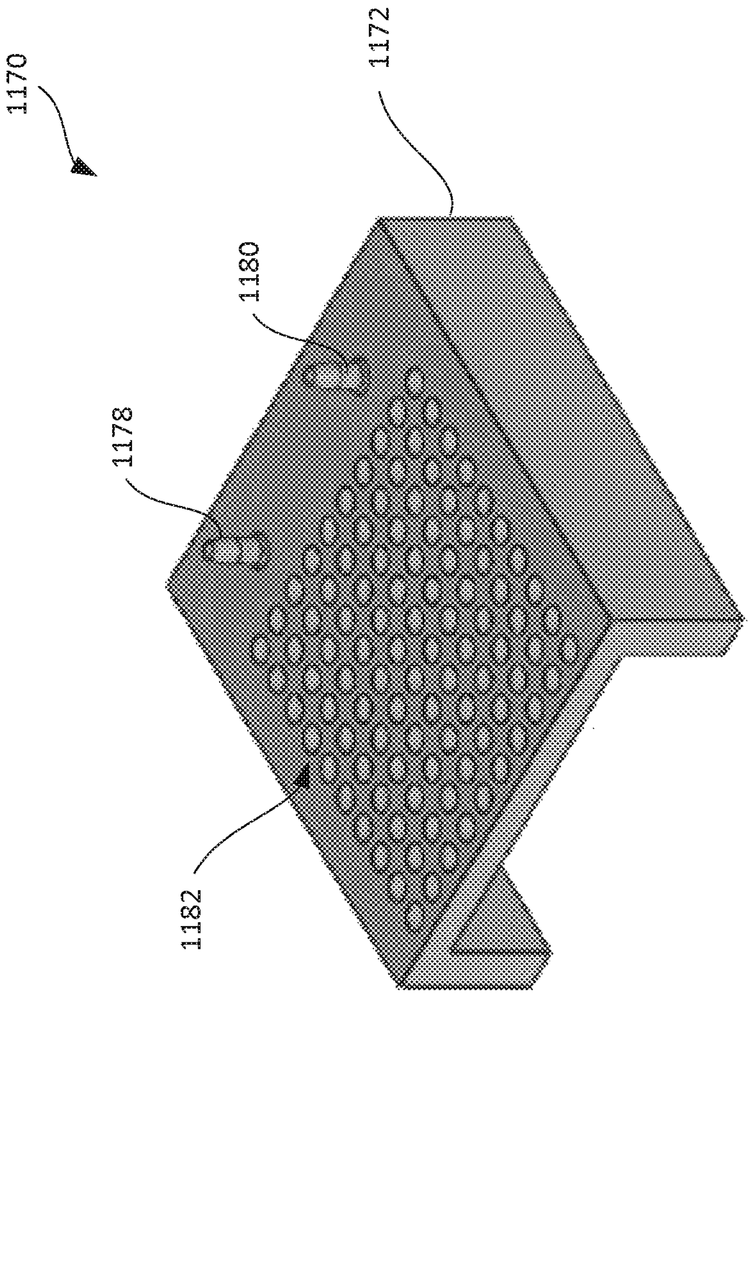
FIG. 12A is a perspective view of an example brain interface configured to fluidly couple a brain to an organ line of the system of FIG. 1.
Figure 12C:
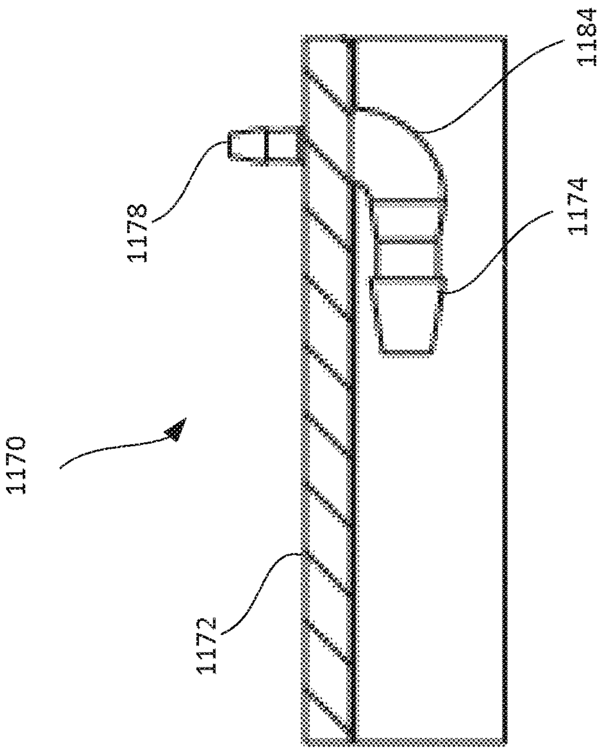
FIG. 12C is cross-sectional view of the example brain interface of FIG. 12A.
Figure 12B:
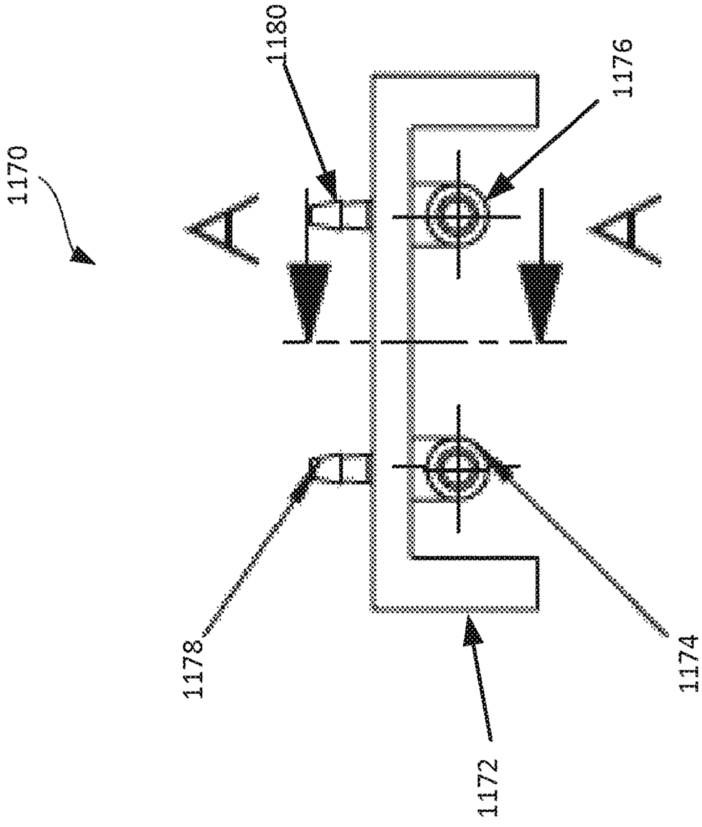
FIG. 12B is a side view of the example brain interface of FIG. 12A.

Prior to placement of the pig brain in the brain housing 1102 for perfusion, the pig brain is fluidly coupled to a brain interface 1170 that is configured to fluidly couple the vasculature of the pig brain to the organ line 144 of the system 100. FIGS. 12A-12C depict an example brain interface 1170 for fluidly coupling a pig brain to the organ line 144. The brain interface 1170 includes a base plate 1172, two fluid input ports 1174, 1176, and two fluid output ports 1178, 1180.

In some implementations, the base plate 1172 is formed of a titanium alloy. In some implementations, the base plate 1172 is formed through laser sintering a titanium alloy. In some implementations, the base plate 1172 is formed through 3D printing. Referring to FIG. 12A, the base plate 1172 defines a plurality of drain holes 1182 therethrough that allow perfusate flowing out of the pig brain to flow through the base plate 1172 into the basin 1104 of the brain housing 1102 such that the perfusate flowing out of the pig brain is collected in the basin 1104.

Each of the fluid inlet ports 1174, 1176 of the brain interface 1170 are fluidly coupled to the organ line 144 using a y-connector and each inlet port 1174, 1176 of the brain interface 1170 receives fresh perfusate flowing out of the organ line 144 into the brain interface 1170. Referring to FIG. 12C, the brain interface 1170 defines flow paths 1184 fluidly coupling each of the fluid inlets ports 1174, 1176 of the brain interface 170 to a respective outlet port 1178, 1180 of the brain interface 170.

Prior to placing a pig brain in the brain housing 1102 and beginning perfusion of the pig brain, each of the carotid arteries of the pig brain is sutured to a respective fluid outlet port 1178, 1180 of the brain interface 1170. Once the carotid arteries of the pig brain are sutured to the fluid outlet ports 1178, 1180 of the brain interface 1170 and the inlet ports 1174, 1176 of the brain interface 1170 are fluidly coupled to the organ line 144, the pig brain and the brain interface 1170 can be positioned within the basin 1104 of the brain housing 1102. The lid 1106 of the brain housing 1102 is coupled to the basin 1102 to enclose the pig brain and brain interface 1170 within the brain housing 1102 throughout the perfusion process. Referring to FIG. 11B, the basin 1104 of the brain housing 1102 defines a slot 1110 that allows a portion of the organ line 144 to enter the basin 1104 with minimal air gaps when the lid 1106 is coupled to the basin 1104.

As fresh perfusate flows along the organ line 144, the perfusate enters the fluid inlet ports 1174, 1176 of the brain interface 1170 and flows through the flow paths 1184 defined by the brain interface 1170, through the fluid outlet ports 1178, 1180 of the brain interface 1170, and into the carotid arteries of the pig brain coupled to the brain interface 1170. As previously discussed, the pressure and flow rate of the perfusate provided to the pig brain are controlled to enable the perfusate entering the carotid arteries of the brain to perfuse the entire vasculature of the brain, including the penetrating arterioles, pre-capillary arterioles, and capillaries of the brain.

While the brain interface 1170 has been depicted as having two fluid outputs, in some implementations, in order to perfuse a pig brain using the perfusion system 100, a brain interface having a single fluid output is provided, and a single artery of the pig brain is sutured to the single fluid output of the brain interface to fluidly couple the pig brain to the brain interface.

In addition, while the perfusion systems described herein have been described as being used to perfuse brains, in some implementations, the perfusion system can be used to perfuse other mammalian (e.g., human) organs. For example, the perfusion system can be used to perfuse kidneys, hearts, livers, lungs, pancreases, etc. In some implementations, an alternate interface is used to fluidly couple the non-brain mammalian organ to the perfusions system 100. Further, in some implementations, an alternate housing device is used to contain and collect perfusate expelled from the non-brain mammalian organ perfused by the system 100. In addition, the perfusate used in the perfusate system 100 may be altered in order to more effectively perfuse non-brain mammalian organs. For example, in some implementations, perfusate used to perfuse non-brain mammalian organs has a higher concentration of oncotically active particles compared to perfusate of brains in order to accommodate the higher capillary filtration rates that occur in non-brain tissue.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. An ex-vivo brain perfusion system for perfusion of a brain, the system comprising:
- a reservoir configured to receive perfusate;
- a housing configured to contain the brain;
- an arterial circuit configured to fluidly couple the reservoir to the brain;
- a venous circuit fluidly coupling the housing to the reservoir;
- an in-line spectroscopy system configured to perform spectroscopy on the perfusate in real-time during a perfusion process;
- a syringe pump manifold comprising:
  - one or more syringes each filled with a respective therapeutic agent, the one or more syringes each being fluidly coupled to the reservoir and configured to introduce the respective therapeutic agent into the perfusate; and
  - a stepper motor configured to control movement of a plunger of each syringe of the one or more syringes, wherein:
- the in-line spectroscopy system is in signal communication with the stepper motor and the stepper motor is controlled to introduce the respective therapeutic agent from the one or more syringes into the perfusate based at least partly on spectroscopy data received by the stepper motor from the in-line spectroscopy system, and
- the ex-vivo brain perfusion system is configured to perfuse the brain with the therapeutic agent to test at least one property of the therapeutic agent.

2. The system of claim 1, wherein the arterial circuit comprises:
- a fluid line fluidly coupling the reservoir to the brain;
- a pressure sensor configured to measure pressure along the fluid line;
- a flow sensor configured to measure a flow rate along the fluid line; and a pulse generation system configured to generate pulsatile flow of perfusate from the reservoir to the brain along the fluid line based on one or more signals generated by at least one of the pressure sensor or the flow sensor.

3. The system of claim 2, wherein the pulse generation system comprises:

a pulse generator comprising:

a housing;

a housing inlet; and a flexible diaphragm; and an air supply system fluidly coupled to the housing inlet of the pulse generator, wherein the air supply system is configured to provide pressurized air into the housing inlet of the pulse generator based on one or more signals generated by at least one of the pressure sensor or the flow sensor.

4. The system of claim 3, wherein the pulse generation system is controlled based on an internal resistance of the brain detected by the pressure sensor.

5. The system of claim 1, wherein the syringe pump manifold is configured to introduce the respective therapeutic agent from the one or more syringes into the reservoir according to a predefined release profile for the respective therapeutic agent.

6. The system of claim 1, further comprising a filtration system configured to filter the perfusate, wherein the filtration system comprises:

a dialyzer comprising an inlet port and an outlet port, the dialyzer configured to filter the perfusate;

an inlet line fluidly coupling the reservoir to the inlet port;

an outlet line fluidly coupling the outlet port to the reservoir; and a pump configured to pump perfusate from the reservoir through the dialyzer.

7. The system of claim 1, wherein the in-line spectroscopy system comprises:

a spectroscopy chamber configured to receive perfusate from the reservoir or the venous circuit;

a heat exchanger fluidly coupled to the spectroscopy chamber and configured to control a temperature of perfusate provided to the spectroscopy chamber; and a spectrometer configured to perform spectroscopy on perfusate in the spectroscopy chamber.

8. The system of claim 1, wherein:

the in-line spectroscopy system is configured to perform spectroscopy on one or more perfusate samples from the reservoir; and the syringe pump manifold is configured to introduce a therapeutic agent from a respective syringe of the one or more syringes into the perfusate according to a predefined release profile for the therapeutic agent based on spectroscopy data generated by performing spectroscopy on one or more perfusate samples from the reservoir using the in-line spectroscopy system.

9. The system of claim 1, wherein:

the system further comprises a filtration system configured to filter the therapeutic agent out of the perfusate; and the filtration system is configured to remove the therapeutic agent from the perfusate according to a predefined release profile for the therapeutic agent based on spectroscopy data generated by performing spectroscopy on one or more perfusate samples from the reservoir using the in-line spectroscopy system.

10. The system of claim 1, wherein the in-line spectroscopy system is configured to perform spectroscopy on one or more perfusate samples collected from the venous circuit to test the at least one property of the therapeutic agent.

11. The system of claim 10, wherein the at least one property of the therapeutic agent comprises whether the therapeutic agent passes through a blood-brain barrier of the brain.

12. The system of claim 1, wherein the in-line spectroscopy system is configured to perform Raman spectroscopy on the perfusate.

13. The system of claim 1, further comprising a spectroscopy probe coupled to the housing, wherein the spectroscopy probe is configured to perform spectroscopy on tissue of the brain in the housing.

14. The system of claim 13, wherein the at least one property of the therapeutic agent is determined based on spectroscopy data generated by performing spectroscopy on the brain using the spectroscopy probe.

15. The system of claim 13, wherein the spectroscopy probe is configured to perform Raman spectroscopy on the tissue of the brain.

16. The system of claim 1, wherein the at least one property of the therapeutic agent is a pharmacodynamic property of the therapeutic agent or a pharmacokinetic property of the therapeutic agent.

17. The system of claim 1, wherein the at least one property of the therapeutic agent is an ability of the therapeutic agent to pass through a blood-brain barrier of the brain.

18. The system of claim 1, wherein the one or more syringes are configured to introduce the respective therapeutic agent into perfusate contained in the reservoir.

19. The system of claim 1, wherein the therapeutic agent comprises at least one of a pharmaceutical compound, an antibody, a biologic, a viral vector, a lipid nanoparticle, or a peptide.

20. The system of claim 1, comprising:

a level sensor coupled to the housing and configured to detect a level of perfusate in the housing;

a housing outlet line fluidly coupled to the housing; and a valve positioned along the housing outlet line and configured to control flow of perfusate out of the housing along the housing outlet line, wherein the valve is controlled to open in response to the level sensor detecting that the level of perfusate in the housing exceeds a threshold level.

* * * * *